(12) United States Patent
Gu et al.

(10) Patent No.: US 10,000,568 B2
(45) Date of Patent: Jun. 19, 2018

(54) COMPOSITIONS AND METHODS FOR DETECTING EGFR IN CANCER

(75) Inventors: Ting-Lei Gu, Woburn, MA (US); Jiong Wu, Reading, MA (US); Susan Kane, Beverly, MA (US); Jian Yu, Hamilton, MA (US); Herbert Haack, South Hamilton, MA (US); James Wieler, Exeter, NH (US); Jun-Ming Cai, South Hamilton, MA (US); Victoria Rimkunas, Somerville, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 701 days.

(21) Appl. No.: 12/450,457

(22) PCT Filed: Apr. 10, 2009

(86) PCT No.: PCT/US2009/002247
§ 371 (c)(1),
(2), (4) Date: Sep. 16, 2011

(87) PCT Pub. No.: WO2009/126306
PCT Pub. Date: Oct. 15, 2009

(65) Prior Publication Data
US 2012/0093837 A1    Apr. 19, 2012

Related U.S. Application Data

(60) Provisional application No. 61/123,699, filed on Apr. 10, 2008, provisional application No. 61/190,597, filed on Aug. 29, 2008.

(51) Int. Cl.
| | | |
|---|---|---|
| C07K 16/00 | (2006.01) | |
| C07K 16/28 | (2006.01) | |
| C07K 14/47 | (2006.01) | |
| C07K 14/485 | (2006.01) | |
| G01N 33/574 | (2006.01) | |

(52) U.S. Cl.
CPC ...... *C07K 16/2863* (2013.01); *C07K 14/4703* (2013.01); *C07K 14/485* (2013.01); *G01N 33/57423* (2013.01); *G01N 33/57484* (2013.01); *C07K 2317/20* (2013.01); *C07K 2317/34* (2013.01); *C07K 2317/56* (2013.01); *C07K 2317/565* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,455,498 B1 | 9/2002 | Vogelstein et al. | 514/14 |
| 7,247,301 B2 | 7/2007 | Van De Winkel et al. | |
| 2005/0272083 A1* | 12/2005 | Seshagiri | 435/6 |
| 2006/0216293 A1 | 9/2006 | Couto et al. | |

FOREIGN PATENT DOCUMENTS

| | | | | |
|---|---|---|---|---|
| WO | WO 01/68711 | 9/2001 | ............. | C07K 16/28 |
| WO | WO 02/30984 | 4/2002 | ............. | C07K 16/00 |
| WO | WO 2007/106432 A2 | 9/2007 | | |

OTHER PUBLICATIONS

Bendig (1995) Methods: a companion methods in enzymology 8: 83-93.*
Paul (1993) Fundamental Immunology, 3rd edition, pp. 292-295.*
Mac Callum et al. (1996) J. Mol. Biol. 262: 732-745.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Wu, Nie, Huse, and Watkins. Humanization of a murine monoclonal antibody by simultaneous optimization of framework and CDR residues. Journal of Molecular Biology, 1999. vol. 294, pp. 151-162.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Skolnick and Fetrow. From genes to protein structure and function: novel applications of computational approaches in the genomic era. Trends in Biotechnology, 2000. vol. 18, pp. 34-39.*
Casset F, et al. A peptide mimetic of an anti-CD4 monoclonal antibody by rational design. Biochemical and Biophysical Research Communications, 2003, vol. 307, p. 198-205.*
Gazdar et al., "Mutations and addiction to EGFR: the Achilles 'heal' of lung cancers?," *Trends in Molecular Medicine*, vol. 10, No. 10, pp. 481-486 (2004).
Marchetti et al., "EGFR Mutations in Non-Small-Cell Lung Cancer: Analysis of a Large Series of Cases and Development of a Rapid and Sensitive Method for Diagnostic Screening With Potential Implications on Pharmacologic Treatment," J Clin. Oncol., vol. 23, No. 4, pp. 857-865 (2005).
Paez et al., "EGFR Mutations in Lung Cancer: Correlation with Clinical Response to Gefitinib Therapy," *Science*, vol. 304, No. 5676, pp. 1497-1500 (2004).
Takano et al., "Epidermal Growth Factor Receptor Gene Mutations and Increased Copy Numbers Predict Gefitinib Sensitivity in Patients With Recurrent Non-Small-Cell Lung Cancer," J Clin. Oncol., vol. 23, No. 28, pp. 6829-6837 (2005).
Yu et al., "Mutation-Specific Antibodies for the Detection of EGFR Mutations in Non-Small-Cell Lung Cancer," Clin. Cancer Res., vol. 15, No. 9, pp. 3023-3028 (2009).
European Patent Office, *Supplementary European Search Report*—International Application No. 09 72 9689, dated Oct. 17, 2011 (13 pages).

(Continued)

*Primary Examiner* — Michael Pak
(74) *Attorney, Agent, or Firm* — Scully Scott Murphy & Presser

(57) ABSTRACT

The invention discloses binding agents to the E746-A750 deletion and the L858R point mutations in the epidermal growth factor receptor (EGFR) molecule, and methods for use thereof, including methods for the diagnosis and treatment of cancer.

5 Claims, 5 Drawing Sheets
(4 of 5 Drawing Sheet(s) Filed in Color)

(56) References Cited

OTHER PUBLICATIONS

International Bureau of WIPO, *International Preliminary Report on Patentability*—International Application No. PCT/US2009/002247, dated Oct. 12, 2010 (7 pages).

Kumar et al. "Structure and Clinical Relevance of the Epidermal Growth Factor Receptor in Human Cancer". *J Clin Oncol.* Apr. 1, 2008. vol. 26 No. 10 pp. 1742-1751.

Yu et al. "Detecting EGFR mutations in NSCLC by immunohistochemistry". *ASCO-NCI-EORTC Annual Meeting on Molecular Markers in Cancer*. Oct. 28, 2008. Gen Poster Session B Abstract 64.

Pao et al. "EGF Recepter Gene Mutations are Common in Lung Cancers From "Never Smokers" And Are Associated With Sensitivity of Tumors to gefitinib and erlotinib". *Proc Nat Acad Sci (USA)* Sep. 7, 2004 vol. 101 No. 36. pp. 13306-13311.

International Search Report for PCT/US2009/02247.

Kawaishi M et al., "Development and characterization of an antibody specifically recognizing a mutant EGFR (L858R) protein expressed frequently in non-small cell lung cancer" Acta Med Kinki Univ (2006) pp. 67-74, vol. 31, No. 2.

Pao, W et al., "EGF receptor gene mutations are common in lung cancers from "never smokers " and are associated with sensitivity of tumors to gefitinib and erlotinib", PNAS, (Sep. 7, 2004), vol. 101, No. 36, pp. 13306-13311.

Xu, J. L., et al., "Diversity in the CDR3 Region of VH Is Sufficient for Most Antibody Specificities", Immunity, (Jul. 2000), vol. 13, pp. 37-45.

Zemlin, M. et al.; "Expressed Murine and Human CDR-H3 Intervals of Equal Length Exhibit Distinct Repertoires that Differ in their Amino Acid Composition and Predicted Range of Structures", J. Mol. Bio., (2003), vol. 334, pp. 733-749.

\* cited by examiner

SEQUENCE LISTING

<160> NUMBER OF SEQ ID NOS: 84

<210> SEQ ID NO 1
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atggagactg ggctgcgctg gcttctcctg gtcgctgtgc tcaaaggtgt ccattgtcag      60
tccttggagg agtccggggg aggcctggtc aagcctgggg catccctgac actcacctgc     120
acagcctctg gattctcctt cagtaacaac gactggatgt gctgggtccg ccaggctcca     180
gggaaggggc tggagtggat cgcatgcatt tatggtggta gtagtattgg cactaattac     240
gcggggtggg cgaaaggccg attcaccatc tccaggacct cgtcgaccac ggtggctctg     300
caaatgacca gtctgacagt cgcggacacg gccacctatt tctgtacgag agatcttgct     360
aacttgtggg gcccaggcac cctggtctcc gtctcctcag gcaacctaa  ggctccatca      420
gtcttcccac tggcccctg  ctgcggggac acacccagcc cacggtgac  cctgggctgc     480
ctggtcaaag gctacctccc ggagccagtg accgtgacct ggaactcggg caccctcacc     540
aatggggtac gcaccttccc gtccgtccgg cagtcctcag gcctctactc gctgagcagc     600
gtggtgagcg tgacctcaag cagccagccc gtcacctgca acgtggccca cccagccacc     660
aacaccaaag tggacaagac cgttgcgccc tcgacatgca gcaagcccat gtgcccaccc     720
cctgaactcc tggggggacc gtctgtcttc atcttccccc caaaacccaa ggacaccctc     780
atgatctcac gcaccccccga ggtcacatgc gtggtggtgg acgtgagcca ggatgaccc      840
gaggtgcagt tcacatggta cataaacaac gagcaggtgc gcaccgcccg gccgccgcta     900
cgggagcagc agttcaacag cacgatccgc gtggtcagca ccctccccat cgcgcaccag     960
gactggctga ggggcaagga gttcaagtgc aaagtccaca acaaggcact cccggccccc    1020
atcgagaaaa ccatctccaa agccagaggg cagccctgg  agccgaaggt ctacaccatg     1080
ggccctcccc gggaggagct gagcagcagg tcggtcagcc tgacctgcat gatcaacggc    1140
ttctaccctt ccgacatctc ggtggagtgg gagaagaacg gaaggcaga  ggacaactac    1200
aagaccacgc cgaccgtgct ggacagcgac ggctcctact tcctctacag caagctctca    1260
gtgcccacga gtgagtggca gcggggcgac gtcttcacct gctccgtgat gcacgaggcc    1320
ttgcacaacc actacacgca gaagtccatc tcccgctctc cgggtaaatg a              1371
```

<210> SEQ ID NO 2
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Glu Thr Gly Leu Arg Trp Leu Leu Leu Val Ala Val Leu Lys Gly
  1               5                  10                  15

Val His Cys Gln Ser Leu Glu Glu Ser Gly Gly Gly Leu Val Lys Pro
             20                  25                  30

Gly Ala Ser Leu Thr Leu Thr Cys Thr Ala Ser Gly Phe Ser Phe Ser
         35                  40                  45
```

-continued

```
Asn Asn Asp Trp Met Cys Trp Val Arg Gln Ala Pro Gly Lys Gly Leu
    50                  55                  60
Glu Trp Ile Ala Cys Ile Tyr Gly Gly Ser Ser Ile Gly Thr Asn Tyr
65                  70                  75                  80
Ala Gly Trp Ala Lys Gly Arg Phe Thr Ile Ser Arg Thr Ser Ser Thr
                85                  90                  95
Thr Val Ala Leu Gln Met Thr Ser Leu Thr Val Ala Asp Thr Ala Thr
                100                 105                 110
Tyr Phe Cys Thr Arg Asp Leu Ala Asn Leu Trp Gly Pro Gly Thr Leu
            115                 120                 125
Val Ser Val Ser Ser Gly Gln Pro Lys Ala Pro Ser Val Phe Pro Leu
130                 135                 140
Ala Pro Cys Cys Gly Asp Thr Pro Ser Ser Thr Val Thr Leu Gly Cys
145                 150                 155                 160
Leu Val Lys Gly Tyr Leu Pro Glu Pro Val Thr Val Thr Trp Asn Ser
                165                 170                 175
Gly Thr Leu Thr Asn Gly Val Arg Thr Phe Pro Ser Val Arg Gln Ser
            180                 185                 190
Ser Gly Leu Tyr Ser Leu Ser Ser Val Val Ser Val Thr Ser Ser Ser
        195                 200                 205
Gln Pro Val Thr Cys Asn Val Ala His Pro Ala Thr Asn Thr Lys Val
210                 215                 220
Asp Lys Thr Val Ala Pro Ser Thr Cys Ser Lys Pro Met Cys Pro Pro
225                 230                 235                 240
Pro Glu Leu Leu Gly Gly Pro Ser Val Phe Ile Phe Pro Pro Lys Pro
                245                 250                 255
Lys Asp Thr Leu Met Ile Ser Arg Thr Pro Glu Val Thr Cys Val Val
            260                 265                 270
Val Asp Val Ser Gln Asp Asp Pro Glu Val Gln Phe Thr Trp Tyr Ile
        275                 280                 285
Asn Asn Glu Gln Val Arg Thr Ala Arg Pro Pro Leu Arg Glu Gln Gln
    290                 295                 300
Phe Asn Ser Thr Ile Arg Val Val Ser Thr Leu Pro Ile Ala His Gln
305                 310                 315                 320
Asp Trp Leu Arg Gly Lys Glu Phe Lys Cys Lys Val His Asn Lys Ala
                325                 330                 335
Leu Pro Ala Pro Ile Glu Lys Thr Ile Ser Lys Ala Arg Gly Gln Pro
            340                 345                 350
Leu Glu Pro Lys Val Tyr Thr Met Gly Pro Pro Arg Glu Glu Leu Ser
        355                 360                 365
Ser Arg Ser Val Ser Leu Thr Cys Met Ile Asn Gly Phe Tyr Pro Ser
370                 375                 380
Asp Ile Ser Val Glu Trp Glu Lys Asn Gly Lys Ala Glu Asp Asn Tyr
385                 390                 395                 400
Lys Thr Thr Pro Thr Val Leu Asp Ser Asp Gly Ser Tyr Phe Leu Tyr
                405                 410                 415
Ser Lys Leu Ser Val Pro Thr Ser Glu Trp Gln Arg Gly Asp Val Phe
            420                 425                 430
Thr Cys Ser Val Met His Glu Ala Leu His Asn His Tyr Thr Gln Lys
        435                 440                 445
Ser Ile Ser Arg Ser Pro Gly Lys
450                 455
```

<210> SEQ ID NO 3
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
atggacatga gggcccccac tcagctgctg gggctcctgc tgctctggct cccaggtgcc    60
acatttgccc aagtgctgac ccagactcca tcctccgtgt ctgcagctgt gggaggcaca   120
gtcaccatca attgccagtc cagtcagagt gtttatagtg actggttatc ctggtatcag   180
cagaaaggag ggcagcctcc cagacaacta atctacgaag catccaaact ggcatctggg   240
gtcccatccc ggttcagtgg cagtggatct gggacacagt tcactctcac catcaacgac   300
gtgcagtgtg acgatgctgc cacttactac tgtctagcca gttatgattg tactagggct   360
gattgccttg ctttcggcgg agggaccgag gtggtggtca gaggtgatcc agttgcacct   420
actgtcctca tcttcccacc agctgctgat caggtggcaa ctggaacagt caccatcgtg   480
tgtgtggcga ataaatactt tcccgatgtc accgtcacct gggaggtgga tggcaccacc   540
caaacaactg gcatcgagaa cagtaaaaca ccgcagaatt ctgcagattg tacctacaac   600
ctcagcagca ctctgacact gaccagcaca cagtacaaca gccacaaaga gtacacctgc   660
aaggtgaccc agggcacgac ctcagtcgtc cagagcttca taggggtga ctgttag      717
```

<210> SEQ ID NO 4
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

Met Asp Met Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Gly Thr Val Thr Ile Asn Cys Gln Ser Ser
        35                  40                  45

Gln Ser Val Tyr Ser Asp Trp Leu Ser Trp Tyr Gln Gln Lys Gly Gly
    50                  55                  60

Gln Pro Pro Arg Gln Leu Ile Tyr Glu Ala Ser Lys Leu Ala Ser Gly
65                  70                  75                  80

Val Pro Ser Arg Phe Ser Gly Ser Gly Ser Gly Thr Gln Phe Thr Leu
                85                  90                  95

Thr Ile Asn Asp Val Gln Cys Asp Asp Ala Ala Thr Tyr Tyr Cys Leu
            100                 105                 110

Ala Ser Tyr Asp Cys Thr Arg Ala Asp Cys Leu Ala Phe Gly Gly Gly
        115                 120                 125

Thr Glu Val Val Val Arg Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln

```
                    180                 185                 190
Asn Ser Ala Asp Cys Thr Tyr Asn Leu Ser Ser Thr Leu Thr Leu Thr
            195                 200                 205

Ser Thr Gln Tyr Asn Ser His Lys Glu Tyr Thr Cys Lys Val Thr Gln
            210                 215                 220

Gly Thr Thr Ser Val Val Gln Ser Phe Asn Arg Gly Asp Cys
225                 230                 235
```

<210> SEQ ID NO 5
<211> LENGTH: 1357
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 5

```
atggagactg ggctgcgctg gcttctcctg gtcgctgtgc tcaaaggtgt ccagtgtcag      60
tcggtggagg agtccggggg tcgcctggtc acgcctggga cccccctaac actcacctgc     120
acagtctctg gattctcccct caataccctat ggagtgagct gggtccgcca ggctccaggg    180
aagggactgg agtggatcgg atacattttt actgatggtc aaacatatta cgcgagctgg     240
gcgaaaggcc gattcaccat ctccaaaacc tcgtcgacca cggtggatct gaaaatcacc     300
agtccgacaa ccgaggacac ggccacctat ttctgtgcca gtagacat ctggggccca       360
ggcaccccgg tcaccgtctc ctcagggcaa cctaaggctc atcagtctt cccactggcc      420
ccctgctgcg ggacacacc cagctccacg gtgaccctgg ctgcctggt caaaggctac       480
ctcccggagc cagtgaccgt gacctggaac tcgggcaccc tcaccaatgg ggtacgcacc     540
ttcccgtccg tccggcagtc ctcaggcctc tactcgctga gcagcgtggt gagcgtgacc     600
tcaagcagcc agcccgtcac ctgcaacgtg gcccacccag ccaccaacac caaagtggac     660
aagaccgttg cgccctcgac atgcagcaag cccacgtgcc cacccctga actcctgggg      720
ggaccgtctg tcttcatctt cccccaaaa cccaaggaca ccctcatgat ctcacgcacc      780
cccgaggtca catgcgtggt ggtggacgtg agccaggatg accccgaggt gcagttcaca     840
tggtacataa caacgagca ggtgcgcacc gcccggccgc gctacgggga gcagcagttc      900
aacagcacga tccgcgtggt cagcaccctc cccatcgcgc accaggactg ctgaggggc      960
aaggagttca gtgcaaagt ccacaacaag gcactccgg cccccatcga gaaaaccatc      1020
tccaaagcca gagggcagcc cctggagccg aaggtctaca ccatgggccc tccccgggag    1080
gagctgagca gcaggtcggt cagcctgacc tgcatgatca cggcttcta cccttccgac     1140
atctcggtgg agtgggagaa gaacgggaag gcagaggaca actacaagac cacgccggcc    1200
gtgctggaca cgacggctc ctacttcctc tacagcaagc tctcagtgcc cacgagtgag     1260
tggcagcggg cgacgtctt cacctgctcc gtgatgcacg aggccttgca caaccactac    1320
acgcagaagt ccatctcccg ctctccggt aaatgat                               1357
```

<210> SEQ ID NO 6
<211> LENGTH: 451
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 6

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Asn
            35                  40                  45

Thr Tyr Gly Val Ser Trp Val Arg Gln Ala Pro Gly Lys Gly Leu Glu
        50                  55                  60

Trp Ile Gly Tyr Ile Phe Thr Asp Gly Gln Thr Tyr Tyr Ala Ser Trp
65                  70                  75                  80

Ala Lys Gly Arg Phe Thr Ile Ser Lys Thr Ser Ser Thr Thr Val Asp
                85                  90                  95

Leu Lys Ile Thr Ser Pro Thr Thr Glu Asp Thr Ala Thr Tyr Phe Cys
            100                 105                 110

Ala Ser Val Asp Ile Trp Gly Pro Gly Thr Pro Val Thr Val Ser Ser
            115                 120                 125

Gly Gln Pro Lys Ala Pro Ser Val Phe Pro Leu Ala Pro Cys Cys Gly
        130                 135                 140

Asp Thr Pro Ser Ser Thr Val Thr Leu Gly Cys Leu Val Lys Gly Tyr
145                 150                 155                 160

Leu Pro Glu Pro Val Thr Val Thr Trp Asn Ser Gly Thr Leu Thr Asn
                165                 170                 175

Gly Val Arg Thr Phe Pro Ser Val Arg Gln Ser Ser Gly Leu Tyr Ser
            180                 185                 190

Leu Ser Ser Val Val Ser Val Thr Ser Ser Ser Gln Pro Val Thr Cys
        195                 200                 205

Asn Val Ala His Pro Ala Thr Asn Thr Lys Val Asp Lys Thr Val Ala
210                 215                 220

Pro Ser Thr Cys Ser Lys Pro Thr Cys Pro Pro Pro Glu Leu Leu Gly
225                 230                 235                 240

Gly Pro Ser Val Phe Ile Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Asp Asp Pro Glu Val Gln Phe Thr Trp Tyr Ile Asn Asn Glu Gln Val
        275                 280                 285

Arg Thr Ala Arg Pro Pro Leu Arg Glu Gln Gln Phe Asn Ser Thr Ile
290                 295                 300

Arg Val Val Ser Thr Leu Pro Ile Ala His Gln Asp Trp Leu Arg Gly
305                 310                 315                 320

Lys Glu Phe Lys Cys Lys Val His Asn Lys Ala Leu Pro Ala Pro Ile
                325                 330                 335

Glu Lys Thr Ile Ser Lys Ala Arg Gly Gln Pro Leu Glu Pro Lys Val
            340                 345                 350

Tyr Thr Met Gly Pro Pro Arg Glu Glu Leu Ser Ser Arg Ser Val Ser
        355                 360                 365

Leu Thr Cys Met Ile Asn Gly Phe Tyr Pro Ser Asp Ile Ser Val Glu
370                 375                 380

Trp Glu Lys Asn Gly Lys Ala Glu Asp Asn Tyr Lys Thr Thr Pro Ala
385                 390                 395                 400

Val Leu Asp Ser Asp Gly Ser Tyr Phe Leu Tyr Ser Lys Leu Ser Val
                405                 410                 415

Pro Thr Ser Glu Trp Gln Arg Gly Asp Val Phe Thr Cys Ser Val Met
```

420                 425                 430
His Glu Ala Leu His Asn His Tyr Thr Gln Lys Ser Ile Ser Arg Ser
            435                 440                 445
Pro Gly Lys
    450

<210> SEQ ID NO 7
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atggacatga gggcccccac tcagctgctg gggctcctgc tgctctggct cccaggtgcc    60
acatttgccc aagtgctgac ccagactcca tcgcccgtgt ctgcagctgt gggaagcaca   120
gtcaccatca gtgccagtc cagtccgagt gtttatagta actacttatc ctggtatcag   180
cagaaatcag gcagcctcc caaacaactg atctatgatg catcccatct ggcatctggg   240
gtcccatcgc ggttcagcgg cagtggatct gggacacagt tcactctcac catcagcggc   300
gtgcagtgtg acgatgctgc cacttactac tgtctaggca gttatgattg tagtagtgtt   360
gattgtcatg ctttcggcgg agggaccgag gtggtggtca aggtgatcc agttgcacct   420 actgtcctca tcttcccacc agctgctgat caggtggcaa ctggaacagt caccatcgtg   480
tgtgtggcga taaatacttt tcccgatgtc accgtcacct gggaggtgga tggcaccacc   540
caaacaactg gcatcgagaa cagtaaaaca ccgcagaatt ctgcagattg tacctacaac   600
ctcagcagca ctctgacact gaccagcaca cagtacaaca gccacaaaga gtacacctgc   660
aaggtgaccc agggcacgac ctcagtcgtc cagagcttca tagggggtga ctgttag     717

<210> SEQ ID NO 8
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Asp Met Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Ser Thr Val Thr Ile Lys Cys Gln Ser Ser
        35                  40                  45

Pro Ser Val Tyr Ser Asn Tyr Leu Ser Trp Tyr Gln Gln Lys Ser Gly
    50                  55                  60

Gln Pro Pro Lys Gln Leu Ile Tyr Asp Ala Ser His Leu Ala Ser Gly
65                  70                  75                  80

Val Pro Ser Arg Phe Ser Gly Ser Gly Ser Gly Thr Gln Phe Thr Leu
                85                  90                  95

Thr Ile Ser Gly Val Gln Cys Asp Asp Ala Ala Thr Tyr Tyr Cys Leu
            100                 105                 110

Gly Ser Tyr Asp Cys Ser Ser Val Asp Cys His Ala Phe Gly Gly Gly
        115                 120                 125

Thr Glu Val Val Val Lys Gly Asp Pro Val Ala Pro Thr Val Leu Ile

```
            130                 135                 140
Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235

<210> SEQ ID NO 9
<211> LENGTH: 10
<212> TYPE: PRT
<213> ORGANISM: Unknown
<220> FEATURE:
<223> OTHER INFORMATION: Description of Unknown: Unknown rabbit peptide

<400> SEQUENCE: 9

Phe Ser Phe Ser Asn Asn Asp Trp Met Cys
1               5                   10

<210> SEQ ID NO 10
<211> LENGTH: 18
<212> TYPE: PRT
<213> ORGANISM: Unknown
<220> FEATURE:
<223> OTHER INFORMATION: Description of Unknown: Unknown rabbit peptide

<400> SEQUENCE: 10

Cys Ile Tyr Gly Gly Ser Ser Ile Gly Thr Asn Tyr Ala Gly Trp Ala
1               5                   10                  15

Lys Gly

<210> SEQ ID NO 11
<211> LENGTH: 5
<212> TYPE: PRT
<213> ORGANISM: Unknown
<220> FEATURE:
<223> OTHER INFORMATION: Description of Unknown: Unknown rabbit peptide

<400> SEQUENCE: 11

Asp Leu Ala Asn Leu
1               5

<210> SEQ ID NO 12
<211> LENGTH: 27
<212> TYPE: PRT
<213> ORGANISM: Unknown
<220> FEATURE:
<223> OTHER INFORMATION: Description of Unknown: Unknown rabbit peptide

<400> SEQUENCE: 12

His Cys Gln Ser Leu Glu Glu Ser Gly Gly Gly Leu Val Lys Pro Gly
1               5                   10                  15

Ala Ser Leu Thr Leu Thr Cys Thr Ala Ser Gly
            20                  25

<210> SEQ ID NO 13
```

```
<211> LENGTH: 14
<212> TYPE: PRT
<213> ORGANISM: Unknown
<220> FEATURE:
<223> OTHER INFORMATION: Description of Unknown: Unknown rabbit peptide

<400> SEQUENCE: 13

Trp Val Arg Gln Ala Pro Gly Lys Gly Leu Glu Trp Ile Ala
1               5                   10

<210> SEQ ID NO 14
<211> LENGTH: 31
<212> TYPE: PRT
<213> ORGANISM: Unknown
<220> FEATURE:
<223> OTHER INFORMATION: Description of Unknown: Unknown rabbit
      polypeptide

<400> SEQUENCE: 14

Arg Phe Thr Ile Ser Arg Thr Ser Ser Thr Thr Val Ala Leu Gln Met
1               5                   10                  15

Thr Ser Leu Thr Val Ala Asp Thr Ala Thr Tyr Phe Cys Thr Arg
            20                  25                  30

<210> SEQ ID NO 15
<211> LENGTH: 11
<212> TYPE: PRT
<213> ORGANISM: Unknown
<220> FEATURE:
<223> OTHER INFORMATION: Description of Unknown: Unknown rabbit peptide

<400> SEQUENCE: 15

Trp Gly Pro Gly Thr Leu Val Ser Val Ser Ser
1               5                   10

<210> SEQ ID NO 16
<211> LENGTH: 12
<212> TYPE: PRT
<213> ORGANISM: Unknown
<220> FEATURE:
<223> OTHER INFORMATION: Description of Unknown: Unknown rabbit peptide

<400> SEQUENCE: 16

Gln Ser Ser Gln Ser Val Tyr Ser Asp Trp Leu Ser
1               5                   10

<210> SEQ ID NO 17
<211> LENGTH: 7
<212> TYPE: PRT
<213> ORGANISM: Unknown
<220> FEATURE:
<223> OTHER INFORMATION: Description of Unknown: Unknown rabbit peptide

<400> SEQUENCE: 17

Glu Ala Ser Lys Leu Ala Ser
1               5

<210> SEQ ID NO 18
<211> LENGTH: 13
<212> TYPE: PRT
<213> ORGANISM: Unknown
<220> FEATURE:
<223> OTHER INFORMATION: Description of Unknown: Unknown rabbit peptide

<400> SEQUENCE: 18

Leu Ala Ser Tyr Asp Cys Thr Arg Ala Asp Cys Leu Ala
1               5                   10
```

```
<210> SEQ ID NO 19
<211> LENGTH: 23
<212> TYPE: PRT
<213> ORGANISM: Unknown
<220> FEATURE:
<223> OTHER INFORMATION: Description of Unknown: Unknown rabbit peptide

<400> SEQUENCE: 19

Ala Gln Val Leu Thr Gln Thr Pro Ser Ser Val Ser Ala Ala Val Gly
1               5                   10                  15

Gly Thr Val Thr Ile Asn Cys
            20

<210> SEQ ID NO 20
<211> LENGTH: 15
<212> TYPE: PRT
<213> ORGANISM: Unknown
<220> FEATURE:
<223> OTHER INFORMATION: Description of Unknown: Unknown rabbit peptide

<400> SEQUENCE: 20

Trp Tyr Gln Gln Lys Gly Gly Gln Pro Pro Arg Gln Leu Ile Tyr
1               5                   10                  15

<210> SEQ ID NO 21
<211> LENGTH: 32
<212> TYPE: PRT
<213> ORGANISM: Unknown
<220> FEATURE:
<223> OTHER INFORMATION: Description of Unknown: Unknown rabbit
      polypeptide

<400> SEQUENCE: 21

Gly Val Pro Ser Arg Phe Ser Gly Ser Gly Ser Gly Thr Gln Phe Thr
1               5                   10                  15

Leu Thr Ile Asn Asp Val Gln Cys Asp Asp Ala Ala Thr Tyr Tyr Cys
            20                  25                  30

<210> SEQ ID NO 22
<211> LENGTH: 10
<212> TYPE: PRT
<213> ORGANISM: Unknown
<220> FEATURE:
<223> OTHER INFORMATION: Description of Unknown: Unknown rabbit peptide

<400> SEQUENCE: 22

Phe Gly Gly Gly Thr Glu Val Val Val Arg
1               5                   10

<210> SEQ ID NO 23
<211> LENGTH: 9
<212> TYPE: PRT
<213> ORGANISM: Unknown
<220> FEATURE:
<223> OTHER INFORMATION: Description of Unknown: Unknown rabbit peptide

<400> SEQUENCE: 23

Phe Ser Leu Asn Thr Tyr Gly Val Ser
1               5

<210> SEQ ID NO 24
<211> LENGTH: 16
<212> TYPE: PRT
<213> ORGANISM: Unknown
<220> FEATURE:
```

<223> OTHER INFORMATION: Description of Unknown: Unknown rabbit peptide

<400> SEQUENCE: 24

Tyr Ile Phe Thr Asp Gly Gln Thr Tyr Tyr Ala Ser Trp Ala Lys Gly
1               5                   10                  15

<210> SEQ ID NO 25
<211> LENGTH: 3
<212> TYPE: PRT
<213> ORGANISM: Unknown
<220> FEATURE:
<223> OTHER INFORMATION: Description of Unknown: Unknown rabbit peptide

<400> SEQUENCE: 25

Val Asp Ile
1

<210> SEQ ID NO 26
<211> LENGTH: 27
<212> TYPE: PRT
<213> ORGANISM: Unknown
<220> FEATURE:
<223> OTHER INFORMATION: Description of Unknown: Unknown rabbit peptide

<400> SEQUENCE: 26

Gln Cys Gln Ser Val Glu Glu Ser Gly Gly Arg Leu Val Thr Pro Gly
1               5                   10                  15

Thr Pro Leu Thr Leu Thr Cys Thr Val Ser Gly
            20                  25

<210> SEQ ID NO 27
<211> LENGTH: 14
<212> TYPE: PRT
<213> ORGANISM: Unknown
<220> FEATURE:
<223> OTHER INFORMATION: Description of Unknown: Unknown rabbit peptide

<400> SEQUENCE: 27

Trp Val Arg Gln Ala Pro Gly Lys Gly Leu Glu Trp Ile Gly
1               5                   10

<210> SEQ ID NO 28
<211> LENGTH: 31
<212> TYPE: PRT
<213> ORGANISM: Unknown
<220> FEATURE:
<223> OTHER INFORMATION: Description of Unknown: Unknown rabbit
      polypeptide

<400> SEQUENCE: 28

Arg Phe Thr Ile Ser Lys Thr Ser Ser Thr Thr Val Asp Leu Lys Ile
1               5                   10                  15

Thr Ser Pro Thr Thr Glu Asp Thr Ala Thr Tyr Phe Cys Ala Ser
            20                  25                  30

<210> SEQ ID NO 29
<211> LENGTH: 11
<212> TYPE: PRT
<213> ORGANISM: Unknown
<220> FEATURE:
<223> OTHER INFORMATION: Description of Unknown: Unknown rabbit peptide

<400> SEQUENCE: 29

Trp Gly Pro Gly Thr Pro Val Thr Val Ser Ser
1               5                   10

```
<210> SEQ ID NO 30
<211> LENGTH: 12
<212> TYPE: PRT
<213> ORGANISM: Unknown
<220> FEATURE:
<223> OTHER INFORMATION: Description of Unknown: Unknown rabbit peptide

<400> SEQUENCE: 30

Gln Ser Ser Pro Ser Val Tyr Ser Asn Tyr Leu Ser
1               5                   10

<210> SEQ ID NO 31
<211> LENGTH: 7
<212> TYPE: PRT
<213> ORGANISM: Unknown
<220> FEATURE:
<223> OTHER INFORMATION: Description of Unknown: Unknown rabbit peptide

<400> SEQUENCE: 31

Asp Ala Ser His Leu Ala Ser
1               5

<210> SEQ ID NO 32
<211> LENGTH: 13
<212> TYPE: PRT
<213> ORGANISM: Unknown
<220> FEATURE:
<223> OTHER INFORMATION: Description of Unknown: Unknown rabbit peptide

<400> SEQUENCE: 32

Leu Gly Ser Tyr Asp Cys Ser Ser Val Asp Cys His Ala
1               5                   10

<210> SEQ ID NO 33
<211> LENGTH: 23
<212> TYPE: PRT
<213> ORGANISM: Unknown
<220> FEATURE:
<223> OTHER INFORMATION: Description of Unknown: Unknown rabbit peptide

<400> SEQUENCE: 33

Ala Gln Val Leu Thr Gln Thr Pro Ser Pro Val Ser Ala Ala Val Gly
1               5                   10                  15

Ser Thr Val Thr Ile Lys Cys
            20

<210> SEQ ID NO 34
<211> LENGTH: 15
<212> TYPE: PRT
<213> ORGANISM: Unknown
<220> FEATURE:
<223> OTHER INFORMATION: Description of Unknown: Unknown rabbit peptide

<400> SEQUENCE: 34

Trp Tyr Gln Gln Lys Ser Gly Gln Pro Pro Lys Gln Leu Ile Tyr
1               5                   10                  15

<210> SEQ ID NO 35
<211> LENGTH: 32
<212> TYPE: PRT
<213> ORGANISM: Unknown
<220> FEATURE:
<223> OTHER INFORMATION: Description of Unknown: Unknown rabbit peptide

<400> SEQUENCE: 35

Gly Val Pro Ser Arg Phe Ser Gly Ser Gly Ser Gly Thr Gln Phe Thr
```

```
                1               5                   10                  15
Leu Thr Ile Ser Gly Val Gln Cys Asp Asp Ala Ala Thr Tyr Tyr Cys
                20                  25                  30
```

<210> SEQ ID NO 36
<211> LENGTH: 10
<212> TYPE: PRT
<213> ORGANISM: Unknown
<220> FEATURE:
<223> OTHER INFORMATION: Description of Unknown: Unknown rabbit peptide

<400> SEQUENCE: 36

```
Phe Gly Gly Gly Thr Glu Val Val Val Lys
1               5                   10
```

<210> SEQ ID NO 37
<211> LENGTH: 99
<212> TYPE: PRT
<213> ORGANISM: Unknown
<220> FEATURE:
<223> OTHER INFORMATION: Description of Unknown: Unknown rabbit
      polypeptide

<400> SEQUENCE: 37

```
His Cys Gln Ser Leu Glu Glu Ser Gly Gly Gly Leu Val Lys Pro Gly
1               5                   10                  15
Ala Ser Leu Thr Leu Thr Cys Thr Ala Ser Gly Phe Ser Phe Ser Asn
                20                  25                  30
Asn Asp Trp Met Cys Trp Val Arg Gln Ala Pro Gly Lys Gly Leu Glu
            35                  40                  45
Trp Ile Cys Ile Tyr Gly Gly Ser Ser Ile Gly Thr Asn Tyr Ala Gly
        50                  55                  60
Trp Ala Lys Gly Arg Phe Thr Ile Ser Arg Thr Ser Ser Thr Thr Val
65                  70                  75                  80
Ala Leu Gln Met Thr Ser Leu Thr Val Ala Asp Thr Ala Thr Tyr Phe
                85                  90                  95
Cys Thr Arg
```

<210> SEQ ID NO 38
<211> LENGTH: 3
<212> TYPE: PRT
<213> ORGANISM: Unknown
<220> FEATURE:
<223> OTHER INFORMATION: Description of Unknown: Unknown rabbit peptide

<400> SEQUENCE: 38

```
Asp Leu Ala
1
```

<210> SEQ ID NO 39
<211> LENGTH: 13
<212> TYPE: PRT
<213> ORGANISM: Unknown
<220> FEATURE:
<223> OTHER INFORMATION: Description of Unknown: Unknown rabbit peptide

<400> SEQUENCE: 39

```
Asn Leu Trp Gly Pro Gly Thr Leu Val Ser Val Ser Ser
1               5                   10
```

<210> SEQ ID NO 40
<211> LENGTH: 123
<212> TYPE: PRT

```
<213> ORGANISM: Unknown
<220> FEATURE:
<223> OTHER INFORMATION: Description of Unknown: Unknown rabbit
      polypeptide

<400> SEQUENCE: 40

Met Asp Met Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Gly Thr Val Thr Ile Asn Cys Gln Ser Ser
        35                  40                  45

Gln Ser Val Tyr Ser Asp Trp Leu Ser Trp Tyr Gln Gln Lys Gly Gly
    50                  55                  60

Gln Pro Pro Arg Gln Leu Ile Tyr Glu Ala Ser Lys Leu Ala Ser Gly
65                  70                  75                  80

Val Pro Ser Arg Phe Ser Gly Ser Gly Ser Gly Thr Gln Phe Thr Leu
                85                  90                  95

Thr Ile Asn Asp Val Gln Cys Asp Asp Ala Ala Thr Tyr Tyr Cys Leu
            100                 105                 110

Ala Ser Tyr Asp Cys Thr Arg Ala Asp Cys Leu
        115                 120

<210> SEQ ID NO 41
<211> LENGTH: 11
<212> TYPE: PRT
<213> ORGANISM: Unknown
<220> FEATURE:
<223> OTHER INFORMATION: Description of Unknown: Unknown rabbit peptide

<400> SEQUENCE: 41

Ala Phe Gly Gly Gly Thr Glu Val Val Val Arg
1               5                   10

<210> SEQ ID NO 42
<211> LENGTH: 97
<212> TYPE: PRT
<213> ORGANISM: Unknown
<220> FEATURE:
<223> OTHER INFORMATION: Description of Unknown: Unknown rabbit
      polypeptide

<400> SEQUENCE: 42

Gln Cys Gln Ser Val Glu Glu Ser Gly Gly Arg Leu Val Thr Pro Gly
1               5                   10                  15

Thr Pro Leu Thr Leu Thr Cys Thr Val Ser Gly Phe Ser Leu Asn Thr
            20                  25                  30

Tyr Gly Val Ser Trp Val Arg Gln Ala Pro Gly Lys Gly Leu Glu Trp
        35                  40                  45

Ile Gly Tyr Ile Phe Thr Asp Gly Gln Thr Tyr Tyr Ala Ser Trp Ala
    50                  55                  60

Lys Gly Arg Phe Thr Ile Ser Lys Thr Ser Ser Thr Thr Val Asp Leu
65                  70                  75                  80

Lys Ile Thr Ser Pro Thr Thr Glu Asp Thr Ala Thr Tyr Phe Cys Ala
                85                  90                  95

Ser

<210> SEQ ID NO 43
<211> LENGTH: 3
<212> TYPE: PRT
```

```
<213> ORGANISM: Unknown
<220> FEATURE:
<223> OTHER INFORMATION: Description of Unknown: Unknown rabbit peptide

<400> SEQUENCE: 43

Val Asp Ile
1

<210> SEQ ID NO 44
<211> LENGTH: 11
<212> TYPE: PRT
<213> ORGANISM: Unknown
<220> FEATURE:
<223> OTHER INFORMATION: Description of Unknown: Unknown rabbit peptide

<400> SEQUENCE: 44

Trp Gly Pro Gly Thr Pro Val Thr Val Ser Ser
1               5                   10

<210> SEQ ID NO 45
<211> LENGTH: 123
<212> TYPE: PRT
<213> ORGANISM: Unknown
<220> FEATURE:
<223> OTHER INFORMATION: Description of Unknown: Unknown rabbit
      polypeptide

<400> SEQUENCE: 45

Met Asp Met Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Ser Thr Val Thr Ile Lys Cys Gln Ser Ser
        35                  40                  45

Pro Ser Val Tyr Ser Asn Tyr Leu Ser Trp Tyr Gln Gln Lys Ser Gly
    50                  55                  60

Gln Pro Pro Lys Gln Leu Ile Tyr Asp Ala Ser His Leu Ala Ser Gly
65                  70                  75                  80

Val Pro Ser Arg Phe Ser Gly Ser Gly Ser Gly Thr Gln Phe Thr Leu
                85                  90                  95

Thr Ile Ser Gly Val Gln Cys Asp Asp Ala Ala Thr Tyr Tyr Cys Leu
            100                 105                 110

Gly Ser Tyr Asp Cys Ser Ser Val Asp Cys His
        115                 120

<210> SEQ ID NO 46
<211> LENGTH: 11
<212> TYPE: PRT
<213> ORGANISM: Unknown
<220> FEATURE:
<223> OTHER INFORMATION: Description of Unknown: Unknown rabbit peptide

<400> SEQUENCE: 46

Ala Phe Gly Gly Gly Thr Glu Val Val Val Lys
1               5                   10

<210> SEQ ID NO 47
<211> LENGTH: 1210
<212> TYPE: PRT
<213> ORGANISM: Homo sapiens

<400> SEQUENCE: 47

Met Arg Pro Ser Gly Thr Ala Gly Ala Ala Leu Leu Ala Leu Leu Ala
```

-continued

```
1               5                   10                  15
Ala Leu Cys Pro Ala Ser Arg Ala Leu Glu Glu Lys Lys Val Cys Gln
                20                  25                  30
Gly Thr Ser Asn Lys Leu Thr Gln Leu Gly Thr Phe Glu Asp His Phe
                35                  40                  45
Leu Ser Leu Gln Arg Met Phe Asn Asn Cys Glu Val Val Leu Gly Asn
50                              55                  60
Leu Glu Ile Thr Tyr Val Gln Arg Asn Tyr Asp Leu Ser Phe Leu Lys
65                  70                  75                  80
Thr Ile Gln Glu Val Ala Gly Tyr Val Leu Ile Ala Leu Asn Thr Val
                85                  90                  95
Glu Arg Ile Pro Leu Glu Asn Leu Gln Ile Ile Arg Gly Asn Met Tyr
                100                 105                 110
Tyr Glu Asn Ser Tyr Ala Leu Ala Val Leu Ser Asn Tyr Asp Ala Asn
                115                 120                 125
Lys Thr Gly Leu Lys Glu Leu Pro Met Arg Asn Leu Gln Glu Ile Leu
                130                 135                 140
His Gly Ala Val Arg Phe Ser Asn Asn Pro Ala Leu Cys Asn Val Glu
145                 150                 155                 160
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
                180                 185                 190
Ser Cys Pro Asn Gly Ser Cys Trp Gly Ala Gly Glu Glu Asn Cys Gln
                195                 200                 205
Lys Leu Thr Lys Ile Ile Cys Ala Gln Gln Cys Ser Gly Arg Cys Arg
                210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
                260                 265                 270
Thr Thr Tyr Gln Met Asp Val Asn Pro Glu Gly Lys Tyr Ser Phe Gly
                275                 280                 285
Ala Thr Cys Val Lys Lys Cys Pro Arg Asn Tyr Val Val Thr Asp His
                290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
                340                 345                 350
Ala Thr Asn Ile Lys His Phe Lys Asn Cys Thr Ser Ile Ser Gly Asp
                355                 360                 365
Leu His Ile Leu Pro Val Ala Phe Arg Gly Asp Ser Phe Thr His Thr
                370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
                420                 425                 430
```

```
His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
        835                 840                 845
```

```
Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
            930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
                995                1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 48
<211> LENGTH: 1186
<212> TYPE: PRT
<213> ORGANISM: Homo sapiens

<400> SEQUENCE: 48
```

```
Leu Glu Glu Lys Lys Val Cys Gln Gly Thr Ser Asn Lys Leu Thr Gln
  1               5                  10                 15

Leu Gly Thr Phe Glu Asp His Phe Leu Ser Leu Gln Arg Met Phe Asn
             20                  25                  30

Asn Cys Glu Val Val Leu Gly Asn Leu Glu Ile Thr Tyr Val Gln Arg
         35                  40                  45

Asn Tyr Asp Leu Ser Phe Leu Lys Thr Ile Gln Glu Val Ala Gly Tyr
     50                  55                  60

Val Leu Ile Ala Leu Asn Thr Val Glu Arg Ile Pro Leu Glu Asn Leu
 65                  70                  75                  80

Gln Ile Ile Arg Gly Asn Met Tyr Tyr Glu Asn Ser Tyr Ala Leu Ala
                 85                  90                  95

Val Leu Ser Asn Tyr Asp Ala Asn Lys Thr Gly Leu Lys Glu Leu Pro
             100                 105                 110

Met Arg Asn Leu Gln Glu Ile Leu His Gly Ala Val Arg Phe Ser Asn
         115                 120                 125

Asn Pro Ala Leu Cys Asn Val Glu Ser Ile Gln Trp Arg Asp Ile Val
     130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                 165                 170                 175

Gly Ala Gly Glu Glu Asn Cys Gln Lys Leu Thr Lys Ile Ile Cys Ala
             180                 185                 190

Gln Gln Cys Ser Gly Arg Cys Arg Gly Lys Ser Pro Ser Asp Cys Cys
         195                 200                 205

His Asn Gln Cys Ala Ala Gly Cys Thr Gly Pro Arg Glu Ser Asp Cys
     210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                 245                 250                 255

Pro Glu Gly Lys Tyr Ser Phe Gly Ala Thr Cys Val Lys Lys Cys Pro
             260                 265                 270

Arg Asn Tyr Val Val Thr Asp His Gly Ser Cys Val Arg Ala Cys Gly
         275                 280                 285

Ala Asp Ser Tyr Glu Met Glu Glu Asp Gly Val Arg Lys Cys Lys Lys
     290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                 325                 330                 335

Asn Cys Thr Ser Ile Ser Gly Asp Leu His Ile Leu Pro Val Ala Phe
             340                 345                 350

Arg Gly Asp Ser Phe Thr His Thr Pro Pro Leu Asp Pro Gln Glu Leu
         355                 360                 365

Asp Ile Leu Lys Thr Val Lys Glu Ile Thr Gly Phe Leu Leu Ile Gln
     370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                 405                 410                 415
```

```
Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
            435                 440                 445

Asn Thr Ile Asn Trp Lys Lys Leu Phe Gly Thr Ser Gly Gln Lys Thr
            450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
            515                 520                 525

Ser Glu Cys Ile Gln Cys His Pro Glu Cys Leu Pro Gln Ala Met Asn
            530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
            595                 600                 605

Leu Glu Gly Cys Pro Thr Asn Gly Pro Lys Ile Pro Ser Ile Ala Thr
610                 615                 620

Gly Met Val Gly Ala Leu Leu Leu Leu Leu Val Val Ala Leu Gly Ile
625                 630                 635                 640

Gly Leu Phe Met Arg Arg His Ile Val Arg Lys Arg Thr Leu Arg
                645                 650                 655

Arg Leu Leu Gln Glu Arg Glu Leu Val Glu Pro Leu Thr Pro Ser Gly
            660                 665                 670

Glu Ala Pro Asn Gln Ala Leu Leu Arg Ile Leu Lys Glu Thr Glu Phe
            675                 680                 685

Lys Lys Ile Lys Val Leu Gly Ser Gly Ala Phe Gly Thr Val Tyr Lys
690                 695                 700

Gly Leu Trp Ile Pro Glu Gly Glu Lys Val Lys Ile Pro Val Ala Ile
705                 710                 715                 720

Lys Glu Leu Arg Glu Ala Thr Ser Pro Lys Ala Asn Lys Glu Ile Leu
            725                 730                 735

Asp Glu Ala Tyr Val Met Ala Ser Val Asp Asn Pro His Val Cys Arg
            740                 745                 750

Leu Leu Gly Ile Cys Leu Thr Ser Thr Val Gln Leu Ile Thr Gln Leu
            755                 760                 765

Met Pro Phe Gly Cys Leu Leu Asp Tyr Val Arg Glu His Lys Asp Asn
            770                 775                 780

Ile Gly Ser Gln Tyr Leu Leu Asn Trp Cys Val Gln Ile Ala Lys Gly
785                 790                 795                 800

Met Asn Tyr Leu Glu Asp Arg Arg Leu Val His Arg Asp Leu Ala Ala
                805                 810                 815

Arg Asn Val Leu Val Lys Thr Pro Gln His Val Lys Ile Thr Asp Phe
            820                 825                 830

Gly Leu Ala Lys Leu Leu Gly Ala Glu Glu Lys Glu Tyr His Ala Glu
```

Gly Gly Lys Val Pro Ile Lys Trp Met Ala Leu Glu Ser Ile Leu His
            850                 855                 860

Arg Ile Tyr Thr His Gln Ser Asp Val Trp Ser Tyr Gly Val Thr Val
865                 870                 875                 880

Trp Glu Leu Met Thr Phe Gly Ser Lys Pro Tyr Asp Gly Ile Pro Ala
            885                 890                 895

Ser Glu Ile Ser Ser Ile Leu Glu Lys Gly Glu Arg Leu Pro Gln Pro
            900                 905                 910

Pro Ile Cys Thr Ile Asp Val Tyr Met Ile Met Val Lys Cys Trp Met
            915                 920                 925

Ile Asp Ala Asp Ser Arg Pro Lys Phe Arg Glu Leu Ile Ile Glu Phe
930                 935                 940

Ser Lys Met Ala Arg Asp Pro Gln Arg Tyr Leu Val Ile Gln Gly Asp
945                 950                 955                 960

Glu Arg Met His Leu Pro Ser Pro Thr Asp Ser Asn Phe Tyr Arg Ala
            965                 970                 975

Leu Met Asp Glu Glu Asp Met Asp Asp Val Val Asp Ala Asp Glu Tyr
            980                 985                 990

Leu Ile Pro Gln Gln Gly Phe Phe Ser Ser Pro Ser Thr Ser Arg Thr
            995                 1000                1005

Pro Leu Leu Ser Ser Leu Ser Ala Thr Ser Asn Asn Ser Thr Val
        1010                1015                1020

Ala Cys Ile Asp Arg Asn Gly Leu Gln Ser Cys Pro Ile Lys Glu
        1025                1030                1035

Asp Ser Phe Leu Gln Arg Tyr Ser Ser Asp Pro Thr Gly Ala Leu
        1040                1045                1050

Thr Glu Asp Ser Ile Asp Asp Thr Phe Leu Pro Val Pro Glu Tyr
        1055                1060                1065

Ile Asn Gln Ser Val Pro Lys Arg Pro Ala Gly Ser Val Gln Asn
        1070                1075                1080

Pro Val Tyr His Asn Gln Pro Leu Asn Pro Ala Pro Ser Arg Asp
        1085                1090                1095

Pro His Tyr Gln Asp Pro His Ser Thr Ala Val Gly Asn Pro Glu
        1100                1105                1110

Tyr Leu Asn Thr Val Gln Pro Thr Cys Val Asn Ser Thr Phe Asp
        1115                1120                1125

Ser Pro Ala His Trp Ala Gln Lys Gly Ser His Gln Ile Ser Leu
        1130                1135                1140

Asp Asn Pro Asp Tyr Gln Gln Asp Phe Phe Pro Lys Glu Ala Lys
        1145                1150                1155

Pro Asn Gly Ile Phe Lys Gly Ser Thr Ala Glu Asn Ala Glu Tyr
        1160                1165                1170

Leu Arg Val Ala Pro Gln Ser Ser Glu Phe Ile Gly Ala
        1175                1180                1185

<210> SEQ ID NO 49
<211> LENGTH: 1205
<212> TYPE: PRT
<213> ORGANISM: Homo sapiens

<400> SEQUENCE: 49

Met Arg Pro Ser Gly Thr Ala Gly Ala Ala Leu Leu Ala Leu Leu Ala
1               5                   10                  15

-continued

```
Ala Leu Cys Pro Ala Ser Arg Ala Leu Glu Lys Lys Val Cys Gln
         20                  25                  30

Gly Thr Ser Asn Lys Leu Thr Gln Leu Gly Thr Phe Glu Asp His Phe
     35                  40                  45

Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
             100                 105                 110

Tyr Glu Asn Ser Tyr Ala Leu Ala Val Leu Ser Asn Tyr Asp Ala Asn
             115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
```

```
                435                 440                 445
Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
                515                 520                 525

Val Ser Arg Gly Arg Glu Cys Val Asp Lys Cys Asn Leu Leu Glu Gly
                530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
                595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
                675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Thr Ser Pro Lys Ala Asn Lys
                740                 745                 750

Glu Ile Leu Asp Glu Ala Tyr Val Met Ala Ser Val Asp Asn Pro His
                755                 760                 765

Val Cys Arg Leu Leu Gly Ile Cys Leu Thr Ser Thr Val Gln Leu Ile
                770                 775                 780

Thr Gln Leu Met Pro Phe Gly Cys Leu Leu Asp Tyr Val Arg Glu His
785                 790                 795                 800

Lys Asp Asn Ile Gly Ser Gln Tyr Leu Leu Asn Trp Cys Val Gln Ile
                805                 810                 815

Ala Lys Gly Met Asn Tyr Leu Glu Asp Arg Arg Leu Val His Arg Asp
                820                 825                 830

Leu Ala Ala Arg Asn Val Leu Val Lys Thr Pro Gln His Val Lys Ile
                835                 840                 845

Thr Asp Phe Gly Leu Ala Lys Leu Leu Gly Ala Glu Glu Lys Glu Tyr
                850                 855                 860
```

His Ala Glu Gly Gly Lys Val Pro Ile Lys Trp Met Ala Leu Glu Ser
865                 870                 875                 880

Ile Leu His Arg Ile Tyr Thr His Gln Ser Asp Val Trp Ser Tyr Gly
                885                 890                 895

Val Thr Val Trp Glu Leu Met Thr Phe Gly Ser Lys Pro Tyr Asp Gly
        900                 905                 910

Ile Pro Ala Ser Glu Ile Ser Ser Ile Leu Glu Lys Gly Glu Arg Leu
            915                 920                 925

Pro Gln Pro Pro Ile Cys Thr Ile Asp Val Tyr Met Ile Met Val Lys
930                 935                 940

Cys Trp Met Ile Asp Ala Asp Ser Arg Pro Lys Phe Arg Glu Leu Ile
945                 950                 955                 960

Ile Glu Phe Ser Lys Met Ala Arg Asp Pro Gln Arg Tyr Leu Val Ile
                965                 970                 975

Gln Gly Asp Glu Arg Met His Leu Pro Ser Pro Thr Asp Ser Asn Phe
            980                 985                 990

Tyr Arg Ala Leu Met Asp Glu Glu Asp Met Asp Asp Val Val Asp Ala
        995                 1000                1005

Asp Glu Tyr Leu Ile Pro Gln Gln Gly Phe Phe Ser Ser Pro Ser
    1010                1015                1020

Thr Ser Arg Thr Pro Leu Leu Ser Ser Leu Ser Ala Thr Ser Asn
    1025                1030                1035

Asn Ser Thr Val Ala Cys Ile Asp Arg Asn Gly Leu Gln Ser Cys
    1040                1045                1050

Pro Ile Lys Glu Asp Ser Phe Leu Gln Arg Tyr Ser Ser Asp Pro
    1055                1060                1065

Thr Gly Ala Leu Thr Glu Asp Ser Ile Asp Asp Thr Phe Leu Pro
    1070                1075                1080

Val Pro Glu Tyr Ile Asn Gln Ser Val Pro Lys Arg Pro Ala Gly
    1085                1090                1095

Ser Val Gln Asn Pro Val Tyr His Asn Gln Pro Leu Asn Pro Ala
    1100                1105                1110

Pro Ser Arg Asp Pro His Tyr Gln Asp Pro His Ser Thr Ala Val
    1115                1120                1125

Gly Asn Pro Glu Tyr Leu Asn Thr Val Gln Pro Thr Cys Val Asn
    1130                1135                1140

Ser Thr Phe Asp Ser Pro Ala His Trp Ala Gln Lys Gly Ser His
    1145                1150                1155

Gln Ile Ser Leu Asp Asn Pro Asp Tyr Gln Gln Asp Phe Phe Pro
    1160                1165                1170

Lys Glu Ala Lys Pro Asn Gly Ile Phe Lys Gly Ser Thr Ala Glu
    1175                1180                1185

Asn Ala Glu Tyr Leu Arg Val Ala Pro Gln Ser Ser Glu Phe Ile
    1190                1195                1200

Gly Ala
1205

<210> SEQ ID NO 50
<211> LENGTH: 1181
<212> TYPE: PRT
<213> ORGANISM: Homo sapiens

<400> SEQUENCE: 50

Leu Glu Glu Lys Lys Val Cys Gln Gly Thr Ser Asn Lys Leu Thr Gln

-continued

```
1               5                   10                  15
Leu Gly Thr Phe Glu Asp His Phe Leu Ser Leu Gln Arg Met Phe Asn
                20                  25                  30

Asn Cys Glu Val Val Leu Gly Asn Leu Glu Ile Thr Tyr Val Gln Arg
                35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
                100                 105                 110

Met Arg Asn Leu Gln Glu Ile Leu His Gly Ala Val Arg Phe Ser Asn
                115                 120                 125

Asn Pro Ala Leu Cys Asn Val Glu Ser Ile Gln Trp Arg Asp Ile Val
130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
                180                 185                 190

Gln Gln Cys Ser Gly Arg Cys Arg Gly Lys Ser Pro Ser Asp Cys Cys
                195                 200                 205

His Asn Gln Cys Ala Ala Gly Cys Thr Gly Pro Arg Glu Ser Asp Cys
                210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
                260                 265                 270

Arg Asn Tyr Val Val Thr Asp His Gly Ser Cys Val Arg Ala Cys Gly
                275                 280                 285

Ala Asp Ser Tyr Glu Met Glu Glu Asp Gly Val Arg Lys Cys Lys Lys
                290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
                340                 345                 350

Arg Gly Asp Ser Phe Thr His Thr Pro Pro Leu Asp Pro Gln Glu Leu
                355                 360                 365

Asp Ile Leu Lys Thr Val Lys Glu Ile Thr Gly Phe Leu Leu Ile Gln
                370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
                420                 425                 430
```

-continued

```
Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
                500                 505                 510

Asp Lys Cys Asn Leu Leu Glu Gly Glu Pro Arg Glu Phe Val Glu Asn
            515                 520                 525

Ser Glu Cys Ile Gln Cys His Pro Glu Cys Leu Pro Gln Ala Met Asn
        530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605

Leu Glu Gly Cys Pro Thr Asn Gly Pro Lys Ile Pro Ser Ile Ala Thr
    610                 615                 620

Gly Met Val Gly Ala Leu Leu Leu Leu Leu Val Ala Leu Gly Ile
625                 630                 635                 640

Gly Leu Phe Met Arg Arg Arg His Ile Val Arg Lys Arg Thr Leu Arg
                645                 650                 655

Arg Leu Leu Gln Glu Arg Glu Leu Val Glu Pro Leu Thr Pro Ser Gly
            660                 665                 670

Glu Ala Pro Asn Gln Ala Leu Leu Arg Ile Leu Lys Glu Thr Glu Phe
        675                 680                 685

Lys Lys Ile Lys Val Leu Gly Ser Gly Ala Phe Gly Thr Val Tyr Lys
    690                 695                 700

Gly Leu Trp Ile Pro Glu Gly Glu Lys Val Lys Ile Pro Val Ala Ile
705                 710                 715                 720

Lys Thr Ser Pro Lys Ala Asn Lys Glu Ile Leu Asp Glu Ala Tyr Val
                725                 730                 735

Met Ala Ser Val Asp Asn Pro His Val Cys Arg Leu Leu Gly Ile Cys
            740                 745                 750

Leu Thr Ser Thr Val Gln Leu Ile Thr Gln Leu Met Pro Phe Gly Cys
        755                 760                 765

Leu Leu Asp Tyr Val Arg Glu His Lys Asp Asn Ile Gly Ser Gln Tyr
    770                 775                 780

Leu Leu Asn Trp Cys Val Gln Ile Ala Lys Gly Met Asn Tyr Leu Glu
785                 790                 795                 800

Asp Arg Arg Leu Val His Arg Asp Leu Ala Ala Arg Asn Val Leu Val
                805                 810                 815

Lys Thr Pro Gln His Val Lys Ile Thr Asp Phe Gly Leu Ala Lys Leu
            820                 825                 830

Leu Gly Ala Glu Glu Lys Glu Tyr His Ala Glu Gly Gly Lys Val Pro
        835                 840                 845
```

Ile Lys Trp Met Ala Leu Glu Ser Ile Leu His Arg Ile Tyr Thr His
850                 855                 860

Gln Ser Asp Val Trp Ser Tyr Gly Val Thr Val Trp Glu Leu Met Thr
865                 870                 875                 880

Phe Gly Ser Lys Pro Tyr Asp Gly Ile Pro Ala Ser Glu Ile Ser Ser
            885                 890                 895

Ile Leu Glu Lys Gly Glu Arg Leu Pro Gln Pro Pro Ile Cys Thr Ile
            900                 905                 910

Asp Val Tyr Met Ile Met Val Lys Cys Trp Met Ile Asp Ala Asp Ser
            915                 920                 925

Arg Pro Lys Phe Arg Glu Leu Ile Ile Glu Phe Ser Lys Met Ala Arg
930                 935                 940

Asp Pro Gln Arg Tyr Leu Val Ile Gln Gly Asp Glu Arg Met His Leu
945                 950                 955                 960

Pro Ser Pro Thr Asp Ser Asn Phe Tyr Arg Ala Leu Met Asp Glu Glu
                965                 970                 975

Asp Met Asp Asp Val Val Asp Ala Asp Glu Tyr Leu Ile Pro Gln Gln
            980                 985                 990

Gly Phe Phe Ser Ser Pro Ser Thr Ser Arg Thr Pro Leu Leu Ser Ser
            995                 1000                1005

Leu Ser Ala Thr Ser Asn Asn Ser Thr Val Ala Cys Ile Asp Arg
    1010                1015                1020

Asn Gly Leu Gln Ser Cys Pro Ile Lys Glu Asp Ser Phe Leu Gln
    1025                1030                1035

Arg Tyr Ser Ser Asp Pro Thr Gly Ala Leu Thr Glu Asp Ser Ile
    1040                1045                1050

Asp Asp Thr Phe Leu Pro Val Pro Glu Tyr Ile Asn Gln Ser Val
    1055                1060                1065

Pro Lys Arg Pro Ala Gly Ser Val Gln Asn Pro Val Tyr His Asn
    1070                1075                1080

Gln Pro Leu Asn Pro Ala Pro Ser Arg Asp Pro His Tyr Gln Asp
    1085                1090                1095

Pro His Ser Thr Ala Val Gly Asn Pro Glu Tyr Leu Asn Thr Val
    1100                1105                1110

Gln Pro Thr Cys Val Asn Ser Thr Phe Asp Ser Pro Ala His Trp
    1115                1120                1125

Ala Gln Lys Gly Ser His Gln Ile Ser Leu Asp Asn Pro Asp Tyr
    1130                1135                1140

Gln Gln Asp Phe Phe Pro Lys Glu Ala Lys Pro Asn Gly Ile Phe
    1145                1150                1155

Lys Gly Ser Thr Ala Glu Asn Ala Glu Tyr Leu Arg Val Ala Pro
    1160                1165                1170

Gln Ser Ser Glu Phe Ile Gly Ala
    1175                1180

<210> SEQ ID NO 51
<211> LENGTH: 1210
<212> TYPE: PRT
<213> ORGANISM: Homo sapiens

<400> SEQUENCE: 51

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

-continued

```
Gly Thr Ser Asn Lys Leu Thr Gln Leu Gly Thr Phe Glu Asp His Phe
         35                  40                  45

Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
             115                 120                 125

Lys Thr Gly Leu Lys Glu Leu Pro Met Arg Asn Leu Gln Glu Ile Leu
 130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
             180                 185                 190

Ser Cys Pro Asn Gly Ser Cys Trp Gly Ala Gly Glu Glu Asn Cys Gln
 195                 200                 205

Lys Leu Thr Lys Ile Ile Cys Ala Gln Gln Cys Ser Gly Arg Cys Arg
 210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
             260                 265                 270

Thr Thr Tyr Gln Met Asp Val Asn Pro Glu Gly Lys Tyr Ser Phe Gly
         275                 280                 285

Ala Thr Cys Val Lys Lys Cys Pro Arg Asn Tyr Val Val Thr Asp His
     290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
             340                 345                 350

Ala Thr Asn Ile Lys His Phe Lys Asn Cys Thr Ser Ile Ser Gly Asp
         355                 360                 365

Leu His Ile Leu Pro Val Ala Phe Arg Gly Asp Ser Phe Thr His Thr
     370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
             420                 425                 430

His Gly Gln Phe Ser Leu Ala Val Val Ser Leu Asn Ile Thr Ser Leu
         435                 440                 445
```

```
Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
                515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
            690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
            835                 840                 845

Gln His Val Lys Ile Thr Asp Phe Gly Arg Ala Lys Leu Leu Gly Ala
850                 855                 860

Glu Glu Lys Glu Tyr His Ala Glu Gly Gly Lys Val Pro Ile Lys Trp
```

```
                865                 870                 875                 880
Met Ala Leu Glu Ser Ile Leu His Arg Ile Tyr Thr His Gln Ser Asp
                    885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
        930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 52
<211> LENGTH: 1186
<212> TYPE: PRT
<213> ORGANISM: Homo sapiens

<400> SEQUENCE: 52

Leu Glu Glu Lys Lys Val Cys Gln Gly Thr Ser Asn Lys Leu Thr Gln
1               5                   10                  15
```

-continued

```
Leu Gly Thr Phe Glu Asp His Phe Leu Ser Leu Gln Arg Met Phe Asn
            20                  25                  30
Asn Cys Glu Val Val Leu Gly Asn Leu Glu Ile Thr Tyr Val Gln Arg
        35                  40                  45
Asn Tyr Asp Leu Ser Phe Leu Lys Thr Ile Gln Glu Val Ala Gly Tyr
    50                  55                  60
Val Leu Ile Ala Leu Asn Thr Val Glu Arg Ile Pro Leu Glu Asn Leu
65                  70                  75                  80
Gln Ile Ile Arg Gly Asn Met Tyr Tyr Glu Asn Ser Tyr Ala Leu Ala
                85                  90                  95
Val Leu Ser Asn Tyr Asp Ala Asn Lys Thr Gly Leu Lys Glu Leu Pro
            100                 105                 110
Met Arg Asn Leu Gln Glu Ile Leu His Gly Ala Val Arg Phe Ser Asn
        115                 120                 125
Asn Pro Ala Leu Cys Asn Val Glu Ser Ile Gln Trp Arg Asp Ile Val
    130                 135                 140
Ser Ser Asp Phe Leu Ser Asn Met Ser Met Asp Phe Gln Asn His Leu
145                 150                 155                 160
Gly Ser Cys Gln Lys Cys Asp Pro Ser Cys Pro Asn Gly Ser Cys Trp
                165                 170                 175
Gly Ala Gly Glu Glu Asn Cys Gln Lys Leu Thr Lys Ile Ile Cys Ala
            180                 185                 190
Gln Gln Cys Ser Gly Arg Cys Arg Gly Lys Ser Pro Ser Asp Cys Cys
        195                 200                 205
His Asn Gln Cys Ala Ala Gly Cys Thr Gly Pro Arg Glu Ser Asp Cys
    210                 215                 220
Leu Val Cys Arg Lys Phe Arg Asp Glu Ala Thr Cys Lys Asp Thr Cys
225                 230                 235                 240
Pro Pro Leu Met Leu Tyr Asn Pro Thr Thr Tyr Gln Met Asp Val Asn
                245                 250                 255
Pro Glu Gly Lys Tyr Ser Phe Gly Ala Thr Cys Val Lys Lys Cys Pro
            260                 265                 270
Arg Asn Tyr Val Val Thr Asp His Gly Ser Cys Val Arg Ala Cys Gly
        275                 280                 285
Ala Asp Ser Tyr Glu Met Glu Glu Asp Gly Val Arg Lys Cys Lys Lys
    290                 295                 300
Cys Glu Gly Pro Cys Arg Lys Val Cys Asn Gly Ile Gly Ile Gly Glu
305                 310                 315                 320
Phe Lys Asp Ser Leu Ser Ile Asn Ala Thr Asn Ile Lys His Phe Lys
                325                 330                 335
Asn Cys Thr Ser Ile Ser Gly Asp Leu His Ile Leu Pro Val Ala Phe
            340                 345                 350
Arg Gly Asp Ser Phe Thr His Thr Pro Pro Leu Asp Pro Gln Glu Leu
        355                 360                 365
Asp Ile Leu Lys Thr Val Lys Glu Ile Thr Gly Phe Leu Leu Ile Gln
    370                 375                 380
Ala Trp Pro Glu Asn Arg Thr Asp Leu His Ala Phe Glu Asn Leu Glu
385                 390                 395                 400
Ile Ile Arg Gly Arg Thr Lys Gln His Gly Gln Phe Ser Leu Ala Val
                405                 410                 415
Val Ser Leu Asn Ile Thr Ser Leu Gly Leu Arg Ser Leu Lys Glu Ile
            420                 425                 430
Ser Asp Gly Asp Val Ile Ile Ser Gly Asn Lys Asn Leu Cys Tyr Ala
```

```
                435                 440                 445
Asn Thr Ile Asn Trp Lys Lys Leu Phe Gly Thr Ser Gly Gln Lys Thr
450                 455                 460
Lys Ile Ile Ser Asn Arg Gly Glu Asn Ser Cys Lys Ala Thr Gly Gln
465                 470                 475                 480
Val Cys His Ala Leu Cys Ser Pro Glu Gly Cys Trp Gly Pro Glu Pro
                485                 490                 495
Arg Asp Cys Val Ser Cys Arg Asn Val Ser Arg Gly Arg Glu Cys Val
                500                 505                 510
Asp Lys Cys Asn Leu Leu Glu Gly Glu Pro Arg Glu Phe Val Glu Asn
                515                 520                 525
Ser Glu Cys Ile Gln Cys His Pro Glu Cys Leu Pro Gln Ala Met Asn
530                 535                 540
Ile Thr Cys Thr Gly Arg Gly Pro Asp Asn Cys Ile Gln Cys Ala His
545                 550                 555                 560
Tyr Ile Asp Gly Pro His Cys Val Lys Thr Cys Pro Ala Gly Val Met
                565                 570                 575
Gly Glu Asn Asn Thr Leu Val Trp Lys Tyr Ala Asp Ala Gly His Val
                580                 585                 590
Cys His Leu Cys His Pro Asn Cys Thr Tyr Gly Cys Thr Gly Pro Gly
                595                 600                 605
Leu Glu Gly Cys Pro Thr Asn Gly Pro Lys Ile Pro Ser Ile Ala Thr
610                 615                 620
Gly Met Val Gly Ala Leu Leu Leu Leu Val Val Ala Leu Gly Ile
625                 630                 635                 640
Gly Leu Phe Met Arg Arg Arg His Ile Val Arg Lys Arg Thr Leu Arg
                645                 650                 655
Arg Leu Leu Gln Glu Arg Glu Leu Val Glu Pro Leu Thr Pro Ser Gly
                660                 665                 670
Glu Ala Pro Asn Gln Ala Leu Leu Arg Ile Leu Lys Glu Thr Glu Phe
                675                 680                 685
Lys Lys Ile Lys Val Leu Gly Ser Gly Ala Phe Gly Thr Val Tyr Lys
                690                 695                 700
Gly Leu Trp Ile Pro Glu Gly Glu Lys Val Lys Ile Pro Val Ala Ile
705                 710                 715                 720
Lys Glu Leu Arg Glu Ala Thr Ser Pro Lys Ala Asn Lys Glu Ile Leu
                725                 730                 735
Asp Glu Ala Tyr Val Met Ala Ser Val Asp Asn Pro His Val Cys Arg
                740                 745                 750
Leu Leu Gly Ile Cys Leu Thr Ser Thr Val Gln Leu Ile Thr Gln Leu
                755                 760                 765
Met Pro Phe Gly Cys Leu Leu Asp Tyr Val Arg Glu His Lys Asp Asn
770                 775                 780
Ile Gly Ser Gln Tyr Leu Leu Asn Trp Cys Val Gln Ile Ala Lys Gly
785                 790                 795                 800
Met Asn Tyr Leu Glu Asp Arg Arg Leu Val His Arg Asp Leu Ala Ala
                805                 810                 815
Arg Asn Val Leu Val Lys Thr Pro Gln His Val Lys Ile Thr Asp Phe
                820                 825                 830
Gly Arg Ala Lys Leu Leu Gly Ala Glu Glu Lys Glu Tyr His Ala Glu
                835                 840                 845
Gly Gly Lys Val Pro Ile Lys Trp Met Ala Leu Glu Ser Ile Leu His
850                 855                 860
```

```
Arg Ile Tyr Thr His Gln Ser Asp Val Trp Ser Tyr Gly Val Thr Val
865                 870                 875                 880

Trp Glu Leu Met Thr Phe Gly Ser Lys Pro Tyr Asp Gly Ile Pro Ala
                885                 890                 895

Ser Glu Ile Ser Ser Ile Leu Glu Lys Gly Glu Arg Leu Pro Gln Pro
            900                 905                 910

Pro Ile Cys Thr Ile Asp Val Tyr Met Ile Met Val Lys Cys Trp Met
        915                 920                 925

Ile Asp Ala Asp Ser Arg Pro Lys Phe Arg Glu Leu Ile Ile Glu Phe
    930                 935                 940

Ser Lys Met Ala Arg Asp Pro Gln Arg Tyr Leu Val Ile Gln Gly Asp
945                 950                 955                 960

Glu Arg Met His Leu Pro Ser Pro Thr Asp Ser Asn Phe Tyr Arg Ala
                965                 970                 975

Leu Met Asp Glu Glu Asp Met Asp Asp Val Val Asp Ala Asp Glu Tyr
            980                 985                 990

Leu Ile Pro Gln Gln Gly Phe Phe Ser Ser Pro Ser Thr Ser Arg Thr
        995                 1000                1005

Pro Leu Leu Ser Ser Leu Ser Ala Thr Ser Asn Asn Ser Thr Val
    1010                1015                1020

Ala Cys Ile Asp Arg Asn Gly Leu Gln Ser Cys Pro Ile Lys Glu
    1025                1030                1035

Asp Ser Phe Leu Gln Arg Tyr Ser Ser Asp Pro Thr Gly Ala Leu
    1040                1045                1050

Thr Glu Asp Ser Ile Asp Asp Thr Phe Leu Pro Val Pro Glu Tyr
    1055                1060                1065

Ile Asn Gln Ser Val Pro Lys Arg Pro Ala Gly Ser Val Gln Asn
    1070                1075                1080

Pro Val Tyr His Asn Gln Pro Leu Asn Pro Ala Pro Ser Arg Asp
    1085                1090                1095

Pro His Tyr Gln Asp Pro His Ser Thr Ala Val Gly Asn Pro Glu
    1100                1105                1110

Tyr Leu Asn Thr Val Gln Pro Thr Cys Val Asn Ser Thr Phe Asp
    1115                1120                1125

Ser Pro Ala His Trp Ala Gln Lys Gly Ser His Gln Ile Ser Leu
    1130                1135                1140

Asp Asn Pro Asp Tyr Gln Gln Asp Phe Phe Pro Lys Glu Ala Lys
    1145                1150                1155

Pro Asn Gly Ile Phe Lys Gly Ser Thr Ala Glu Asn Ala Glu Tyr
    1160                1165                1170

Leu Arg Val Ala Pro Gln Ser Ser Glu Phe Ile Gly Ala
    1175                1180                1185

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Lys Ile Pro Val Ala Ile Lys Thr Ser Pro Lys Ala Asn Lys Glu
1               5                   10                  15
```

```
<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Cys Lys Ile Thr Asp Phe Gly Arg Ala Lys Leu Leu Gly Ala Glu
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Ile Pro Val Ala Ile Lys Thr Ser Pro Lys Ala Asn Lys Glu
1               5                   10                  15

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Ile Thr Asp Phe Gly Arg Ala Lys Leu Leu Gly Ala Glu
1               5                   10

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 57

Thr Asp Xaa Gly Arg
1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 58

His His His His His His
1               5

<210> SEQ ID NO 59
<211> LENGTH: 12
<212> TYPE: PRT
<213> ORGANISM: Unknown
<220> FEATURE:
```

<223> OTHER INFORMATION: Description of Unknown: Unknown rabbit peptide

<400> SEQUENCE: 59

His Lys Met His Ser His Pro Arg Leu Thr Ser Pro
1               5                   10

<210> SEQ ID NO 60
<211> LENGTH: 12
<212> TYPE: PRT
<213> ORGANISM: Unknown
<220> FEATURE:
<223> OTHER INFORMATION: Description of Unknown: Unknown rabbit peptide

<400> SEQUENCE: 60

His Thr Ser Tyr Tyr Thr Asn Thr Asp Trp Gly Arg
1               5                   10

<210> SEQ ID NO 61
<211> LENGTH: 12
<212> TYPE: PRT
<213> ORGANISM: Unknown
<220> FEATURE:
<223> OTHER INFORMATION: Description of Unknown: Unknown rabbit peptide
<220> FEATURE:
<221> NAME/KEY: MOD_RES
<222> LOCATION: (11)..(11)
<223> OTHER INFORMATION: Any amino acid

<400> SEQUENCE: 61

His Trp Gly His His Ser Lys Ser His Pro Xaa Arg
1               5                   10

<210> SEQ ID NO 62
<211> LENGTH: 12
<212> TYPE: PRT
<213> ORGANISM: Unknown
<220> FEATURE:
<223> OTHER INFORMATION: Description of Unknown: Unknown rabbit peptide

<400> SEQUENCE: 62

His Trp Gly Asn His Ser Lys Ser His Pro Gln Arg
1               5                   10

<210> SEQ ID NO 63
<211> LENGTH: 12
<212> TYPE: PRT
<213> ORGANISM: Unknown
<220> FEATURE:
<223> OTHER INFORMATION: Description of Unknown: Unknown rabbit peptide

<400> SEQUENCE: 63

His Arg Gly His His Ser Gln Ser Gln Thr His Arg
1               5                   10

<210> SEQ ID NO 64
<211> LENGTH: 12
<212> TYPE: PRT
<213> ORGANISM: Unknown
<220> FEATURE:
<223> OTHER INFORMATION: Description of Unknown: Unknown rabbit peptide

<400> SEQUENCE: 64

His Leu Lys His His Pro Pro Tyr Lys Asp Ala Thr
1               5                   10

<210> SEQ ID NO 65
<211> LENGTH: 7

```
<212> TYPE: PRT
<213> ORGANISM: Unknown
<220> FEATURE:
<223> OTHER INFORMATION: Description of Unknown: Unknown rabbit peptide

<400> SEQUENCE: 65

Gly Pro Thr Ala Asp Thr Asn
1               5

<210> SEQ ID NO 66
<211> LENGTH: 7
<212> TYPE: PRT
<213> ORGANISM: Unknown
<220> FEATURE:
<223> OTHER INFORMATION: Description of Unknown: Unknown rabbit peptide

<400> SEQUENCE: 66

Ser Ala Phe Tyr Gln Leu Asn
1               5

<210> SEQ ID NO 67
<211> LENGTH: 7
<212> TYPE: PRT
<213> ORGANISM: Unknown
<220> FEATURE:
<223> OTHER INFORMATION: Description of Unknown: Unknown rabbit peptide

<400> SEQUENCE: 67

Arg Pro Ser Thr Ser Pro Leu
1               5

<210> SEQ ID NO 68
<211> LENGTH: 7
<212> TYPE: PRT
<213> ORGANISM: Unknown
<220> FEATURE:
<223> OTHER INFORMATION: Description of Unknown: Unknown rabbit peptide

<400> SEQUENCE: 68

Gln Leu Phe Thr Ser Ala Ser
1               5

<210> SEQ ID NO 69
<211> LENGTH: 7
<212> TYPE: PRT
<213> ORGANISM: Unknown
<220> FEATURE:
<223> OTHER INFORMATION: Description of Unknown: Unknown rabbit peptide

<400> SEQUENCE: 69

Met Pro Asn Arg Asn Arg Ser
1               5

<210> SEQ ID NO 70
<211> LENGTH: 7
<212> TYPE: PRT
<213> ORGANISM: Unknown
<220> FEATURE:
<223> OTHER INFORMATION: Description of Unknown: Unknown rabbit peptide

<400> SEQUENCE: 70

Gly Asp Gly Pro Leu Arg Arg
1               5

<210> SEQ ID NO 71
<211> LENGTH: 7
<212> TYPE: PRT
```

```
<213> ORGANISM: Unknown
<220> FEATURE:
<223> OTHER INFORMATION: Description of Unknown: Unknown rabbit peptide

<400> SEQUENCE: 71

Lys His Pro Thr Tyr Arg Gln
1               5

<210> SEQ ID NO 72
<211> LENGTH: 7
<212> TYPE: PRT
<213> ORGANISM: Unknown
<220> FEATURE:
<223> OTHER INFORMATION: Description of Unknown: Unknown rabbit peptide

<400> SEQUENCE: 72

Lys Leu His Gln Met Arg Thr
1               5

<210> SEQ ID NO 73
<211> LENGTH: 7
<212> TYPE: PRT
<213> ORGANISM: Unknown
<220> FEATURE:
<223> OTHER INFORMATION: Description of Unknown: Unknown rabbit peptide

<400> SEQUENCE: 73

Lys Val Ser Arg Thr Gly Arg
1               5

<210> SEQ ID NO 74
<211> LENGTH: 7
<212> TYPE: PRT
<213> ORGANISM: Unknown
<220> FEATURE:
<223> OTHER INFORMATION: Description of Unknown: Unknown rabbit peptide

<400> SEQUENCE: 74

Val Pro Arg Ala Ile Tyr His
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Thr Asp Phe Gly Arg Ala Lys Leu
1               5

<210> SEQ ID NO 76
<211> LENGTH: 12
<212> TYPE: PRT
<213> ORGANISM: Unknown
<220> FEATURE:
<223> OTHER INFORMATION: Description of Unknown: Unknown rabbit peptide

<400> SEQUENCE: 76

Met Glu Ile Ile Thr Asp Leu Gly Arg Pro Met Leu
1               5                   10

<210> SEQ ID NO 77
<211> LENGTH: 12
<212> TYPE: PRT
```

-continued

```
<213> ORGANISM: Unknown
<220> FEATURE:
<223> OTHER INFORMATION: Description of Unknown: Unknown rabbit peptide

<400> SEQUENCE: 77

Ala Lys Ser Ser Thr Asp Phe Gly Arg Ala Gln Val
1               5                   10

<210> SEQ ID NO 78
<211> LENGTH: 12
<212> TYPE: PRT
<213> ORGANISM: Unknown
<220> FEATURE:
<223> OTHER INFORMATION: Description of Unknown: Unknown rabbit peptide

<400> SEQUENCE: 78

Tyr Pro Pro Ala Pro Leu Gly Arg Thr Thr Asp Phe
1               5                   10

<210> SEQ ID NO 79
<211> LENGTH: 12
<212> TYPE: PRT
<213> ORGANISM: Unknown
<220> FEATURE:
<223> OTHER INFORMATION: Description of Unknown: Unknown rabbit peptide

<400> SEQUENCE: 79

Lys Arg Gln Ile Pro Ser Pro Pro Gln Trp Asp Pro
1               5                   10

<210> SEQ ID NO 80
<211> LENGTH: 12
<212> TYPE: PRT
<213> ORGANISM: Unknown
<220> FEATURE:
<223> OTHER INFORMATION: Description of Unknown: Unknown rabbit peptide

<400> SEQUENCE: 80

Thr Phe His Asn Lys Leu Leu Leu His Asp Trp Arg
1               5                   10

<210> SEQ ID NO 81
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 81

His Cys Gln Ser Leu Glu Glu Ser Gly Gly Gly Leu Val Lys Pro Gly
1               5                   10                  15

Ala Ser Leu Thr Leu Thr Cys Thr Ala Ser Gly Phe Ser Phe Ser Asn
                20                  25                  30

Asn Asp Trp Met Cys Trp Val Arg Gln Ala Pro Gly Lys Gly Leu Glu
            35                  40                  45

Trp Ile Ala Cys Ile Tyr Gly Gly Ser Ser Ile Gly Thr Asn Tyr Ala
        50                  55                  60

Gly Trp Ala Lys Gly Arg Phe Thr Ile Ser Arg Thr Ser Ser Thr Thr
65                  70                  75                  80

Val Ala Leu Gln Met Thr Ser Leu Thr Val Ala Asp Thr Ala Thr Tyr
                85                  90                  95

Phe Cys Thr Arg Asp Leu Ala Asn Leu Trp Gly Pro Gly Thr Leu Val
            100                 105                 110
```

Ser Val Ser Ser
        115

<210> SEQ ID NO 82
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 82

Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Ser Asp
            20                  25                  30

Trp Leu Ser Trp Tyr Gln Gln Lys Gly Gly Gln Pro Pro Arg Gln Leu
        35                  40                  45

Ile Tyr Glu Ala Ser Lys Leu Ala Ser Gly Val Pro Ser Arg Phe Ser
    50                  55                  60

Gly Ser Gly Ser Gly Thr Gln Phe Thr Leu Thr Ile Asn Asp Val Gln
65                  70                  75                  80

Cys Asp Asp Ala Ala Thr Tyr Tyr Cys Leu Ala Ser Tyr Asp Cys Thr
                85                  90                  95

Arg Ala Asp Cys Leu Ala Phe Gly Gly Gly Thr Glu Val Val Val Arg
            100                 105                 110

<210> SEQ ID NO 83
<211> LENGTH: 111
<212> TYPE: PRT
<213> ORGANISM: Artificial Sequence
<220> FEATURE:
<223> OTHER INFORMATION: Synthetic Peptide

<400> SEQUENCE: 83

Gln Cys Gln Ser Val Glu Glu Ser Gly Gly Arg Leu Val Thr Pro Gly
1               5                   10                  15

Thr Pro Leu Thr Leu Thr Cys Thr Val Ser Gly Phe Ser Leu Asn Thr
            20                  25                  30

Tyr Gly Val Ser Trp Val Arg Gln Ala Pro Gly Lys Gly Leu Glu Trp
        35                  40                  45

Ile Gly Tyr Ile Phe Thr Asp Gly Gln Thr Tyr Tyr Ala Ser Trp Ala
    50                  55                  60

Lys Gly Arg Phe Thr Ile Ser Lys Thr Ser Thr Thr Val Asp Leu
65                  70                  75                  80

Lys Ile Thr Ser Pro Thr Thr Glu Asp Thr Ala Thr Tyr Phe Cys Ala
                85                  90                  95

Ser Val Asp Ile Trp Gly Pro Gly Thr Pro Val Thr Val Ser Ser
            100                 105                 110

<210> SEQ ID NO 84
<211> LENGTH: 112
<212> TYPE: PRT
<213> ORGANISM: Artificial Sequence
<220> FEATURE:
<223> OTHER INFORMATION: Synthetic Peptide

<400> SEQUENCE: 84

Ala Gln Val Leu Thr Gln Thr Pro Ser Pro Val Ser Ala Ala Val Gly
1               5                   10                  15

Ser Thr Val Thr Ile Lys Cys Gln Ser Ser Pro Ser Val Tyr Ser Asn

-continued

```
                    20                  25                  30
Tyr Leu Ser Trp Tyr Gln Gln Lys Ser Gly Gln Pro Pro Lys Gln Leu
            35                  40                  45

Ile Tyr Asp Ala Ser His Leu Ala Ser Gly Val Pro Ser Arg Phe Ser
        50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Leu Gly Ser Tyr Asp Cys Ser
                85                  90                  95

Ser Val Asp Cys His Ala Phe Gly Gly Gly Thr Glu Val Val Val Lys
                100                 105                 110
```

COMPOSITIONS AND METHODS FOR DETECTING EGFR IN CANCER

RELATED APPLICATIONS

This application is a National Stage Entry Application of PCT/US2009/002247, filed Apr. 10, 2009, which itself claims the benefit of and priority to U.S. provisional patent application U.S. Ser. No. 61/123,699, filed Apr. 10, 2008, and U.S. provisional patent application U.S. Ser. No. 61/190,597, filed Aug. 29, 2008, both of which are hereby incorporated by reference herein in their entirety.

BACKGROUND OF THE INVENTION

The invention relates generally to the field of mutant proteins and genes involved in cancer, and to the detection, diagnosis and treatment of cancer.

Cancer is major cause of death in humans. Lung cancer is a major cause of cancer-related mortality worldwide and is expected to remain a major health problem for the foreseeable future. It is broadly divided into small cell lung cancer (SCLC, 20% of lung cancers), and non-small cell lung cancer (NSCLC, 80% of lung cancers). Somatic mutations in the epidermal growth factor receptor (EGFR) gene are found in a subset of lung adenocarcinomas and are associated with sensitivity to the EGFR tyrosine kinase inhibitors (TKI) Gefitinib [Lynch, T. J., et al., N Engl J Med, 2004. 350(21): p. 2129-39, and Paez, J. G., et al., Science, 2004. 304(5676): p. 1497-500] and Erlotinib [Pao, W., et al., Proc Natl Acad Sci USA, 2004. 101(36): p. 13306-11]. Many types of EGFR mutations have been reported, but the most common non-small cell lung cancer (NSCLC)-associated EGFR mutations are the 15-bp nucleotide in-frame deletion in exon 19 (E746-A750del) and the point mutation replacing leucine with arginine at codon 858 in exon 21 (L858R) [Pao, W., et al., Proc Natl Acad Sci USA, 2004. 101(36): p. 13306-11; Riely, G. J., et al., Clin Cancer Res, 2006. 12(24): p. 7232-41; and Kosaka, T., et al., Cancer Res, 2004. 64(24): p. 8919-23. These two mutations represent 85-90% of EGFR mutations in NSCLC patients. Importantly, patients with these mutations have been shown to respond well to EGFR inhibitors including Gefitinib and Erlotinib [Riely, G. J., et al., Clin Cancer Res, 2006. 12(24): p. 7232-41; Inoue, A., et al., J Clin Oncol, 2006. 24(21): p. 3340-6; Marchetti, A., et al., J Clin Oncol, 2005. 23(4): p. 857-65; and Mitsudomi, T., et al., J Clin Oncol, 2005. 23(11): p. 2513-20.]. Therefore detection of these mutations is an important method to improve treatment of lung cancer patients.

Since EGFR mutational analysis in lung adenocarcinoma can guide treatment decisions and to enroll patients on specific arms of clinical trials, direct DNA sequencing of PCR amplified products has been developed to detect EGFR mutation in patient tumor tissue. However, these tests have not been widely adopted due the high costs of the equipment and reagents, the difficulty of performing the assay and the length of time required for completion of the test. In addition, DNA sequencing has a limited sensitivity for the detection of tumor cells containing an EGFR mutation within a background of nonmutant normal cells. A minimum of 50% tumor cells is required to ensure the accuracy of the EGFR sequencing assay. Recently, other DNA based methods have been developed to improve the detection of EGFR mutation in lung cancer specimens, including TaqMan PCR, Scorpions ARMS, MALDI TOF MS-based genotyping, dHPLC, and single molecule sequencing. However, these methods are not routine procedures in clinical labs and remain expensive and time-consuming. Also they do not identify mutation-status on a cellular basis. Therefore, their sensitivity is dependent on the percentage tumor cells contained in the sample used to produce the homogenate, and samples obtained from standard biopsy are usually not sufficient for DNA sequencing. On the other hand, Immunohistochemistry (IHC) is a well-established method of solid tumor analysis routinely performed in all clinical laboratories. This method is a more accessible technique in clinical diagnosis and the interpretation is less affected by the percentage of the cancer cells in the tumor specimens or the amount of tumor tissue available for analysis. The method also allows for the simultaneous analysis of other proteins or protein modifications. However, total expression level of EGFR by IHC has not been shown to predict response to tyrosine kinase inhibitor therapy in NSCLC [Meert, A. P., et al., Eur Respir J, 2002. 20(4): p. 975-81]. Thus, development of antibodies that specifically detect mutant EGFR protein and that may be used in IHC will be a valuable addition to the clinical diagnosis and treatment of lung cancer.

A related challenge facing diagnostic analysis of solid tumor samples including lung cancer tumors is access to the tissue sample. Repeated biopsies are not clinically feasible for almost all tumor types. Therefore, alternative sources of cancer cells must be obtained. This is especially important in the context of targeted therapeutics in which repeated tumor analysis may be used to guide the drug therapy. A number of cancer cell sources are available in some tumor types including circulating cancer cells (CTCs), ascites, bronchial swabs, ductal adenocarincoma is of a cancer tissue type selected from the group consisting of lung cancer, colon cancer, breast cancer, cervical cancer, pancreatic cancer, prostate cancer, stomach cancer, and esophageal cancer. circulating proteins may be detected by standard protein assays such as an ELISA assay. In this example, the mutation EGFR protein would be captured and detected with a pair of antibodies including an antibody against the total protein and an antibody to the mutation. Such an assay would enable routine and repeated analysis of treated patients to best match the choice of drug and drug regime to the direct affect the therapy was having on the patient's tumor.

SUMMARY OF THE INVENTION

The invention provides binding agents, such as rabbit monoclonal antibodies, that specifically bind to an EGFR molecule with an E746-A750 deletion and an EGFR molecule with a L858R point mutation.

Accordingly, in a first aspect, the invention provides a binding agent that specifically binds an epidermal growth factor receptor (EGFR) molecule comprising a deletion at position E746-A750. In some embodiments, the epidermal growth factor receptor (EGFR) molecule is from a human. In some embodiments, the binding agent comprises at least one complementary determining region (CDR), wherein the CDR comprises a sequence selected from the group consisting of SEQ ID NO: 9, SEQ ID NO: 10, SEQ ID NO: 11, SEQ ID NO: 16, SEQ ID NO 17, and SEQ ID NO: 18. In some embodiments, the binding agent specifically binds to an epitope comprising an amino acid sequence comprising a threonine-serine-proline sequence. In some embodiments, where the binding agent is an antibody, the antibody is produced by the clone deposited with the ATCC and given the designation number ATCC No. PTA-9151.

In another aspect, the invention provides a binding agent that specifically binds to an epidermal growth factor receptor (EGFR) molecule comprising a point mutation substituting leucine with arginine at position 858. In some embodiments, the epidermal growth factor receptor (EGFR) molecule is from a human. In some embodiments, the binding agent comprises at least one complementary determining region (CDR), wherein the CDR comprises an amino acid sequence selected from the group consisting of SEQ ID NO: 23, SEQ ID NO: 24, SEQ ID NO: 25, SEQ ID NO: 30, SEQ ID NO 31, and SEQ ID NO: 32. In some embodiments, the binding agent specifically binds to an epitope comprising an amino acid sequence comprising a threonine-aspartic acid-X-glycine-arginine sequence, where X is any amino acid residue. In some embodiments, where the binding agent is an antibody, the antibody is produced by the clone deposited with the ATCC and given the designation number ATCC No. PTA-9152.

In a further aspect, the invention provides a polynucleotide (e.g., a purified polynucleotide) encoding a binding agent that specifically binds to an epidermal growth factor receptor (EGFR) molecule comprising a deletion at position E746-A750. In a further aspect, the invention provides a polynucleotide (e.g., a purified polynucleotide) encoding a binding agent that specifically binds to an epidermal growth factor receptor (EGFR) molecule comprising a point mutation substituting leucine with arginine at position 858. In further aspects, the invention provides vectors (e.g., expression vectors) comprising the polynucleotides.

In another aspect, the invention provides methods for identifying a cancer that will respond favorably to a therapy targeting aberrant expression of an EGFR molecule. The methods comprise comprising (a) contacting a biological sample from the cancer with the binding agent that specifically binds to an epidermal growth factor receptor (EGFR) molecule comprising a deletion at position E746-A750 to obtain an amount of binding and (b) comparing the result of step (a) with an amount of binding obtained by contacting a biological sample from a healthy individual with the binding agent, wherein a change in the amount of binding from the cancer as compared to the amount of binding from the healthy individual indicates the cancer will respond favorably to the therapy. In various embodiments, the biological sample from the cancer and the biological sample from the healthy individual are of the same tissue type. In some embodiments, the cancer is from a human patient. In some embodiments, the cancer is a non-small-cell lung cancer (NSCLC). In some embodiments, the cancer is an adenocarcinoma or a squamous cell carcinoma. In some embodiments, the cancer is of a tissue type selected from the group consisting of lung cancer, colon cancer, breast cancer, cervical cancer, pancreatic cancer, prostate cancer, stomach cancer, and esophageal cancer.

In another aspect, the invention provides methods for identifying a cancer that will respond favorably to a therapy targeting aberrant expression of an EGFR molecule. The methods comprise comprising (a) contacting a biological sample from the cancer with the binding agent that specifically binds to an epidermal growth factor receptor (EGFR) molecule comprising a point mutation substituting leucine with arginine at position 858 to obtain an amount of binding and (b) comparing the result of step (a) with an amount of binding obtained by contacting a biological sample from a healthy individual with the binding agent, wherein a change in the amount of binding from the cancer as compared to the amount of binding from the healthy individual indicates the cancer will respond favorably to the therapy. In various embodiments, the biological sample from the cancer and the biological sample from the healthy individual are of the same tissue type. In some embodiments, the cancer is from a human patient. In some embodiments, the cancer is a non-small-cell lung cancer (NSCLC). In some embodiments, the cancer is an adenocarcinoma. In some embodiments, the adenocarincoma is of a cancer tissue type selected from the group consisting of lung cancer, colon cancer, breast cancer, cervical cancer, pancreatic cancer, prostate cancer, stomach cancer, and esophageal cancer.

In various embodiments, the amount of binding is determined using an assay method selected from the group consisting of Western blot, immunofluorescence, ELISA, IHC, flow cytometry, immunoprecipitation, autoradiography, scintillation counting, and chromatography.

In further aspects, the invention also provides a composition comprising a binding agent specifically binds to an epidermal growth factor receptor (EGFR) molecule comprising a point mutation substituting leucine with arginine at position 858, a binding agent that specifically binds to an epidermal growth factor receptor (EGFR) molecule comprising a deletion at position E746-A750, or both binding agents. In some embodiments, the composition further comprises a pharmaceutically acceptable carrier. The invention also provides a composition comprising a polynucleotide encoding a binding agent specifically binds to an epidermal growth factor receptor (EGFR) molecule comprising a point mutation substituting leucine with arginine at position 858, a polynucleotide encoding a binding agent that specifically binds to an epidermal growth factor receptor (EGFR) molecule comprising a deletion at position E746-A750, or both polynucleotides. In some embodiments, the composition further comprises a pharmaceutically acceptable carrier.

In further aspects, the invention provides a method for treating a patient having or suspected of having a cancer that will respond favorably to a therapy targeting aberrant expression of an EGFR molecule. The method includes administering to the patient an effective amount of a composition of the invention.

Another aspect of the invention discloses method for identifying the L858R point mutation and/or E746-A750 deletion in EGFR status in a patient, said method comprising the steps of: a) obtaining a biological sample from a patient; b) screening the sample with a binding agent that specifically binds the L858R point mutation and/or E746-A750 deletion in EGFR; and c) determining the presence or absence of the E746-A750 deletions and/or the L8585R point mutation in EGFR in the sample. In some embodiments, the method includes screening the sample with a wildtype EGFR-specific antibody. In some embodiments, the method includes screening the sample with a pan-keratin antibody (e.g., a pan-cytokeratin antibody).

Another aspect of the invention describes kits for the detection of E746-A750 deletion or L858R point mutations in EGFR in a sample, said kit comprising (a) a binding agent that specifically binds to the E746-A750 deletion in EGFR and/or a binding agent that specifically binds to the L858R point mutations in EGFR; and b) instructions for detecting E746-A750 deletion or L858R point mutations in EGFR in a sample.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Figure 1:
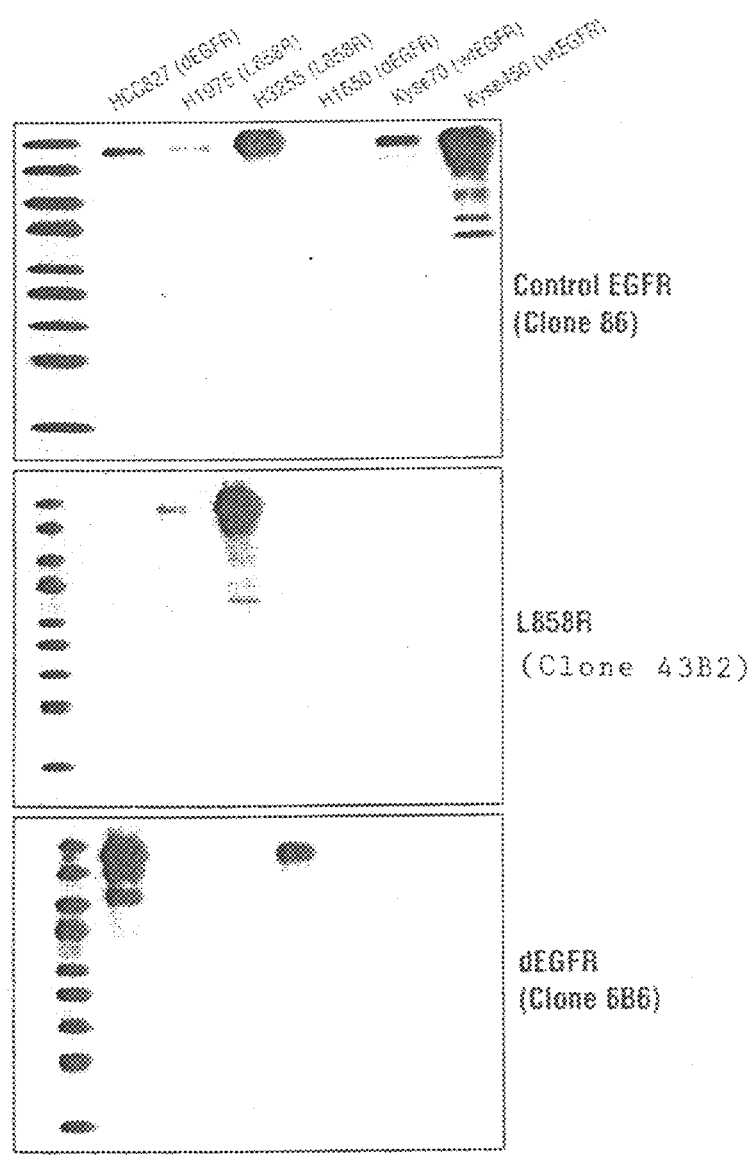
FIG. 1 is a representative Western blotting depicting the reactivity of the antibodies of the invention for EGFR and mutants thereof in the indicated cell lines. The control wildtype (wt) EGFR-specific antibody clone 86 (top panel) binds to (i.e., is reactive to) lysates prepared from all indicated cell lines, although the reactivity is somewhat reduced in the cells expressing mutant EGFR (i.e., HCC827, H1975, H3255, and H1650 cells). The EGFR L858R-specific antibody (clone 6B6) is reactive only to H175 and H3255 cells (middle panel), while the dEGFR (i.e., EGFR del746-A750)-specific antibody (clone 43B2) is reactive only to HCC827 and H1650 cells.

The invention relates generally to mutant proteins and genes involved in cancer, and to the detection, diagnosis and treatment of cancer utilizing the antibodies of the invention disclosed herein.

Higher EGFR protein expression determined by immunohistochemistry is observed in the majority of squamous cell carcinomas, a small percentage of large cell carcinomas, adenocarcinomas, and bronchial pre-neoplastic lesions, implicating its significance in lung carcinogenesis [Selvaggi, G., et al., Ann Oncol, 2004. 15(1): p. 28-32]. There are conflicting data about the prognostic importance of EGFR protein levels in NSCLC. A meta-analysis of these studies failed to show a significant correlation between EGFR levels and survival [Meert, A. P., et al., Eur Respir J, 2002. 20(4): p. 975-81]. Retrospective evaluations of the relationship between EGFR positive by immunohistochemistry and response showed that EGFR immunohistochemistry results were not predictive of response in the original trial of Gefitinib and later research data [Clark, G. M., et al., J Thorac Oncol, 2006. 1(8): p. 837-46; Tsao, M. S., et al., N Engl J Med, 2005. 353(2): p. 133-44; Dziadziuszko, R., et al., Ann Oncol, 2007. 18(3): p. 447-52; and Cappuzzo, F., et al., J Natl Cancer Inst, 2005. 97(9): p. 643-55]. Since the presence of certain EGFR mutation correlates with clinical response to either gefitinib or erlotinib, there is a huge demand for the identification of such EGFR mutations in NSCLC patients.

Accordingly, the invention provides rabbit mAbs that were generated, as described herein, with selective reactivity for EGFR protein with E746-A750del and L858R point mutation. Western blots and immunofluorescence showed the antibodies were specific to E746-A750del and L858R mutant EGFR proteins. These antibodies were further analyzed by IHC in xenograft tumors, cell pellets and molecularly pre-typed samples of NSCLC and compared with anti-wtEGFR mAb. The RmAbs were selected to detect either E746-A750del or L858R point mutant EGFR proteins, not wtEGFR or other types of EGFR mutations. On the other hand, the anti-wtEGFR Ab was widely reactive with a higher proportion of NSCLC. Thus, the binding agents described herein specifically recognize either E746-A750del or L858R mutant EGFR protein.

The invention provides binding agents (such as antibodies) that specifically bind to the EGFR L858R mutation and the EGFR E746-A750del mutation. The EGFR mutation-specific antibodies are extremely valuable in the clinical management (e.g., the treatment and diagnosis) of cancer patients, particularly patients who have or are suspected of having NSCLC or other cancer characterized by aberrant EGFR.

As used in this specification, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, unless specifically indicated otherwise, the word "or" is used in the "inclusive" sense of "and/or" and not the "exclusive" sense of "either/or." In the specification and the appended claims, the singular forms include plural referents unless the context clearly dictates otherwise.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Any suitable materials and/or methods known to those of skill can be utilized in carrying out the present invention. However, preferred materials and methods are described. Materials, reagents and the like to which reference is made in the following description and examples are obtainable from commercial sources, unless otherwise noted.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

The epidermal growth factor receptor (EGFR; also known as ErbB-1 and HER1 in humans) is the cell-surface receptor for members of the epidermal growth factor family (EGF-family) of extracellular protein ligands. The amino acid sequence of wild-type human EGFR (including the signal sequence) is provided herein as SEQ ID NO: 47; the amino acid sequence of wild-type human EGFR (minus the signal sequence) is provided herein as SEQ ID NO: 48. Patients of non-small cell lung cancer (NSCLC) carrying the somatic mutation of epidermal growth factor receptor (EGFR) have been shown to be hyperresponsive to the EGFR tyrosine kinase inhibitor Gefitinib [Lynch, T. J., et al., N Engl J Med, 2004. 350(21): p. 2129-39, and Paez, J. G., et al., Science, 2004. 304(5676): p. 1497-500] and Erlotinib [Pao, W., et al., Proc Natl Acad Sci USA, 2004. 101(36): p. 13306-11].

Mutations are known to arise in the EGFR molecule. As used herein, the term "mutant" or "mutation" refers to a molecule (e.g., a polypeptide or a polynucleotide) that has a different structure than the wild-type molecule. That difference in structure from the wild-type molecule includes, without limitation, a different sequence (e.g., a different amino acid or nucleotide sequence), additional sequences, missing sequences (i.e., a portion of the sequence is missing), changes in modification (e.g., methylation, phosphorylation, etc.), and/or fusion of all or part of the wild-type molecule with another molecule. By "wild-type" is meant that form of the molecule that naturally occurs in the majority of individuals of the species from which the mutant molecule is derived, and/or the form of the molecule that naturally occurs in an healthy individual (e.g., non-cancerous) individual of a species from which the mutant molecule is derived. The sequence of the wild-type molecule is that typically provided in the GenBank database. For example, the amino acid sequence of wild-type human EGFR is provided in SEQ ID NO: 47 (without the 24 amino acid long signal sequence) and SEQ ID NO: 48 (with the signal sequence).

As used herein, an "EGFR mutant" includes any type of mutation (i.e., change) in an EGFR molecule that renders the EGFR mutant different than wildtype EGFR. The most common NSCLC-associated EGFR mutations are the 15-bp nucleotide in-frame deletion in exon 19 (E746-A750del; amino acid sequence (including the signal sequence) provided in SEQ ID NO: 49 and without the signal sequence provided in SEQ ID NO: 50) and the point mutation replacing leucine with arginine at codon 858 in exon 21 (L858R; amino acid sequence (including the signal sequence) provided in SEQ ID NO: 51 and without the signal sequence provided in SEQ ID NO: 52). These two EGFR mutants account for 85-90% EGFR mutations [Riely, G. J., et al., Clin Cancer Res, 2006. 12(24): p. 7232-41]. The ability to detect mutated gene products in cancer cells can identify patients most likely benefit from such therapies, and make clinical trials more efficient and informative.

Thus, in a first aspect, the invention provides a binding agent that specifically binds an epidermal growth factor receptor (EGFR) molecule comprising a deletion at position E746-A750. In some embodiments, the epidermal growth factor receptor (EGFR) molecule is from a human. In some embodiments, the binding agent comprises at least one complementary determining region (CDR), wherein the CDR comprises a sequence selected from the group consisting of SEQ ID NO: 9, SEQ ID NO: 10, SEQ ID NO: 11, SEQ ID NO: 16, SEQ ID NO 17, and SEQ ID NO: 18. In some embodiments, the binding agent specifically binds to an epitope comprising an amino acid sequence comprising a threonine-serine-proline sequence.

In another aspect, the invention provides a binding agent that specifically binds to an epidermal growth factor receptor (EGFR) molecule comprising a point mutation substituting leucine with arginine at position 858. In some embodiments, the epidermal growth factor receptor (EGFR) molecule is from a human. In some embodiments, the binding agent comprises at least one complementary determining region (CDR), wherein the CDR comprises an amino acid sequence selected from the group consisting of SEQ ID NO: SEQ ID NO: 23, SEQ ID NO: 24, SEQ ID NO: 25, SEQ ID NO: 30, SEQ ID NO 31, and SEQ ID NO: 32. In some embodiments, the binding agent specifically binds to an epitope comprising an amino acid sequence comprising a threonine-aspartic acid-X-glycine-arginine sequence, where X is any amino acid residue.

As used herein, by "binding agent" is meant a molecule including, without limitation, an organic molecule such as a polypeptide (e.g., an antibody, as defined herein) or a polynucleotide, or an inorganic molecule such as a small chemical molecule or a synthetic polymer, that is capable of binding to a reference target molecule (which may also be referred to as an antigen). In some embodiments, the binding agent specifically binds to the reference target molecule. As used herein, by "specifically binding" or "specifically binds" means that a binding agent of the invention (e.g., an antibody) interacts with its target molecule (e.g., a EGFR E746-A750 deletion mutant), where the interaction is interaction is dependent upon the presence of a particular structure (i.e., the antigenic determinant or epitope) on the target molecule; in other words, the binding agent is recognizing and binding to a specific structure rather than to all molecules in general. A binding agent that specifically binds to the target molecule may be referred to as a target-specific binding agent. For example, an antibody that specifically binds to an EGFR L858R polypeptide may be referred to as an EGFR L858R-specific antibody (or an EGFR L858R mutant-specific antibody).

In some embodiments, the binding agents of the invention are purified.

By "purified" (or "isolated") refers to a molecule such as a nucleic acid sequence (e.g., a polynucleotide) or an amino acid sequence (e.g., a polypeptide) that is removed or separated from other components present in its natural environment. For example, an isolated antibody is one that is separated from other components of a eukaryotic cell (e.g., the endoplasmic reticulum or cytoplasmic proteins and RNA). An isolated antibody-encoding polynucleotide is one that is separated from other nuclear components (e.g., histones) and/or from upstream or downstream nucleic acid sequences (e.g., an isolated antibody-encoding polynucleotide may be separated from the endogenous heavy chain or light chain promoter). An isolated nucleic acid sequence or amino acid sequence of the invention may be at least 60% free, or at least 75% free, or at least 90% free, or at least 95% free from other components present in natural environment of the indicated nucleic acid sequence or amino acid sequence.

In various embodiments of the invention, the reference target molecule to which the binding agent specifically binds is an EGFR L858R mutant polypeptide (also referred to as a mutation) or an EGFR E746-A750del mutant polypeptide. In some embodiments, the EGFR L858R polypeptide has the amino acid sequence set forth in SEQ ID NO: 51 or SEQ ID NO: 52. In some embodiments, the EGFR E746-A750del polypeptide has the amino acid sequence set forth in SEQ ID NO: 49 or SEQ ID NO: 50.

As used herein, the terms "polypeptide", "peptide" and "protein" are used interchangeably herein to refer to polymers of amino acids of any length. The polymer may be linear or branched, and it may comprise modified amino acids. Where the amino acid sequence is provided, unless otherwise specified, the sequence is in an N' terminal to C' terminal orientation (e.g., a TSP sequence is N' threonine-serine-proline C'). In some embodiments, the polymer may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

In some embodiments, a binding agent of the invention has a $K_D$ for its target molecule (e.g., a EGFR L858R polypeptide) of $1 \times 10^{-6}$ M or less. In some embodiments, a binding agent of the invention binds to its target molecule with a $K_D$ of $1 \times 10^{-7}$ M or less, or a $K_D$ of $1 \times 10^{-8}$ M or less, or a $K_D$ of $1 \times 10^{-9}$ M or less, or a $K_D$ of $1 \times 10^{-10}$ M or less, of a $K_D$ of $1 \times 10^{-11}$ M or less, of a $K_D$ of $1 \times 10^{-12}$ M or less. In certain embodiments, the $K_D$ of a binding agent of the invention for its target molecule is 1 pM to 500 pM, or between 500 pM to 1 μM, or between 1 μM to 100 nM, or between 100 mM to 10 nM. As used herein, by the term "$K_D$", is intended to refer to the dissociation constant of an interaction between two molecules (e.g., the dissociation constant between a binding agent (e.g., an antibody) and its specific target molecule.

In some embodiments, the binding molecule is an antibody.

Naturally occurring antibodies (also called immunoglobulins) are made up of two classes of polypeptide chains, light chains and heavy chains. A non-limiting antibody of the invention can be an intact, four immunoglobulin chain antibody comprising two heavy chains and two light chains. The heavy chain of the antibody can be of any isotype including IgM, IgG, IgE, IgG, IgA or IgD or sub-isotype including IgG1, IgG2, IgG3, IgG4, IgE1, IgE2, etc. The light chain can be a kappa light chain or a lambda light chain. A single naturally occurring antibody comprises two identical copies of a light chain and two identical copies of a heavy chain. The heavy chains, which each contain one variable domain ($V_H$) and multiple constant domains, bind to one another via disulfide bonding within their constant domains to form the "stem" of the antibody. The light chains, which each contain one variable domain ($V_L$) and one constant domain, each bind to one heavy chain via disulfide binding. The variable domain of each light chain is aligned with the variable domain of the heavy chain to which it is bound. The variable regions of both the light chains and heavy chains contain three hypervariable regions sandwiched between four more conserved framework regions (FR). These hypervariable regions, known as the complementary determining regions (CDRs), form loops that comprise the principle antigen binding surface of the antibody (see Kabat, E. A. et al., Sequences of Proteins of Immunological Interest, National Institutes of Health, Bethesda, Md., (1987)). The four framework regions largely adopt a beta-sheet conformation and the CDRs form loops connecting, and in some cases forming part of, the beta-sheet structure. The CDRs in each chain are held in close proximity by the framework regions and, with the CDRs from the other chain, contribute to the formation of the antigen binding domain.

Also within the invention are antibody molecules with fewer than 4 chains, including single chain antibodies, Camelid antibodies and the like and components of the antibody, including a heavy chain or a light chain.

Thus, as used herein, the term "antibody" is meant to include intact immunoglobulin molecules of any isotype or sub-isotype (e.g., IgG, IgG1, IgG2a, IgG2b, IgG3, IgG4, IgM, IgD, IgE, IgE1, IgE2, or IgA) from any species (e.g., human, rodent, camelid), as well as antigen binding domain fragments thereof, such as Fab, Fab', F(ab')$_2$; variants thereof such as scFv, Fv, Fd, dAb, bispecific scFvs, diabodies, linear antibodies (see U.S. Pat. No. 5,641,870, Zapata et al., Protein Eng 8 (10): 1057-1062 [1995]); single-chain antibody molecules; and multispecific antibodies formed from antibody fragments; and any polypeptide comprising a binding domain which is, or is homologous to, an antibody binding domain. By "antigen binding domain" is meant any portion of an antibody that retains specific binding activity of the intact antibody (i.e., any portion of an antibody that is capable of specific binding to an epitope on the intact antibody's target molecule). As used herein, the term "epitope" refers to the smallest portion of a target molecule capable of being specifically bond by the antigen binding domain of a binding agent (e.g., of an antibody). The minimal size of an epitope may be about five or six to seven amino acids. Non-limiting antigen binding domains include portions of the heavy chain and/or light chain CDRs of an intact antibody, the heavy and/or light chain variable regions of an intact antibody, full length heavy or light chains of an intact antibody, or an individual CDR from either the heavy chain or the light chain of an intact antibody.

Antibodies of the invention include but are not limited to polyclonal, monoclonal, monospecific, polyspecific antibodies and fragments thereof and chimeric antibodies comprising an immunoglobulin binding domain fused to another polypeptide.

The term "does not bind," when appeared in context of a binding agent, means that the binding agent (e.g., an antibody) does not substantially react with the indicated molecule. One of skill in the art will appreciate that the expression may be applicable in those instances when the binding agent (e.g., a EGFR L858R mutation-specific antibody) either does not apparently bind to another target (e.g., wild-type EGFR) as ascertained in commonly used experimental detection systems (Western blotting, IHC, Immunofluorescence, etc.) and compared to a non-specific control antibody (i.e., an antibody that is does not specifically bind any molecule or binds to another target molecule, such as the pan-cytokeratin-specific antibody described below). A control antibody preparation might be, for instance, purified immunoglobulin from a pre-immune animal of the same species, an isotype- and species-matched antibody of the invention. Tests using control antibodies to demonstrate specificity are recognized by one of skill in the art as appropriate and definitive.

In some embodiments of the invention, an antibody that specifically binds to a target molecule provides a detection signal at least 5-, 10-, or 20-fold higher than a detection signal provided with other proteins when used in an immunochemical assay. In some embodiments, antibodies that specifically bind to a target molecule do not detect other proteins in immunochemical assays and can immunoprecipitate the target molecule from solution.

In some embodiments an immunoglobulin chain may comprise in order from 5' to 3', a variable region and a constant region. The variable region may comprise three complementarity determining regions (CDRs), with interspersed framework (FR) regions for a structure FR1, CDR1, FR2, CDR2, FR3, CDR3 and FR4. Also within the invention are heavy or light chain variable regions, framework regions and CDRs. An antibody of the invention may comprise a heavy chain constant region that comprises some or all of a CH1 region, hinge, CH2 and CH3 region. An antibody of the invention may comprise a light chain constant region that comprises some or all of a CL region.

An antibody of the invention may have a $K_D$ for its target molecule of $1 \times 10^{-7}$ m or less. In other embodiments, the antibody binds to its target molecule with a $K_D$ of $1 \times 10^{-8}$ M, $1 \times 10^{-9}$ M, $1 \times 10^{-10}$ M, $1 \times 10^{-11}$ M, $1 \times 10^{-12}$ M or less. In certain embodiments, the $K_D$ is 1 pM to 500 pM, between 500 pM to 1 µM, between 1 µM to 100 nM, or between 100 mM to 10 nM.

Antibodies of the invention can be derived from any species of animal, including mammals. Non-limiting exemplary natural antibodies include antibodies derived from human, camelids (e.g., camels and llamas), chickens, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Natural antibodies are the antibodies produced by a host animal. "Genetically altered antibodies" refer to antibodies wherein the amino acid sequence has been varied from that of a native antibody. Because of the relevance of recombinant DNA techniques to this application, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

Other antibodies specifically contemplated are oligoclonal antibodies. As used herein, the phrase "oligoclonal antibodies" refers to a predetermined mixture of distinct monoclonal antibodies. See, e.g., PCT publication WO 95/20401; U.S. Pat. Nos. 5,789,208 and 6,335,163. In one embodiment, oligoclonal antibodies consisting of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule. In view of the assays and epitopes disclosed herein, those skilled in the art can generate or select antibodies or mixtures of antibodies that are applicable for an intended purpose and desired need.

Recombinant antibodies in the invention are also included in the present invention. These recombinant antibodies have the same amino acid sequence as the natural antibodies or have altered amino acid sequences of the natural antibodies in the present application. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, U.S. Pat. No. 6,331, 415; U.S. Pat. No. 7,498,024, and U.S. Pat. No. 7,485,291, which are herein incorporated by reference in their entirety).

Antibodies can be engineered in numerous ways. They can be made as single-chain antibodies (including small modular immunopharmaceuticals or SMIPs™), Fab and F(ab')₂ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548, 640; 5,565,332; 5,225,539; 6,103,889; and 5,260,203.

The genetically altered antibodies should be functionally equivalent to the above-mentioned natural antibodies. In certain embodiments, modified antibodies provide improved stability or/and therapeutic efficacy. Examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of this invention can be modified post-translationally (e.g., acetylation, and/or phosphorylation) or can be modified synthetically (e.g., the attachment of a labeling group).

Antibodies with engineered or variant constant or Fc regions can be useful in modulating effector functions, such as, for example, antigen-dependent cytotoxicity (ADCC) and complement-dependent cytotoxicity (CDC).

In certain embodiments, genetically altered antibodies are chimeric antibodies and humanized antibodies.

A chimeric antibody is an antibody having portions derived from different antibodies. For example, a chimeric antibody may have a variable region and a constant region derived from two different antibodies. The donor antibodies may be from different species. In certain embodiments, the variable region of a chimeric antibody is non-human, e.g., murine, and the constant region is human.

The genetically altered antibodies used in the invention include CDR grafted humanized antibodies. In one embodiment, the humanized antibody comprises heavy and/or light chain CDRs of a non-human donor immunoglobulin and heavy chain and light chain frameworks and constant regions of a human acceptor immunoglobulin. The method of making humanized antibody is disclosed in U.S. Pat. Nos. 5,530,101; 5,585,089; 5,693,761; 5,693,762; and 6,180,370 each of which is incorporated herein by reference in its entirety.

In some embodiments, an antibody of the invention will comprise substantially all of at least one, and typically two, variable domains (such as Fab, Fab', F(ab')2, Fabc, Fv) in which one or more of the CDR regions are synthetic amino acid sequences that specifically bind to the target molecule, and all or substantially all of the framework regions are those of a human immunoglobulin consensus sequence. The framework regions can also be those of a native human immunoglobulin sequence. Other CDR regions in the antibody can be selected to have human immunoglobulin consensus sequences for such CDRs or the sequence of a native human antibody. The antibody optimally also will comprise at least a portion of an immunoglobulin constant region (Fc) of a human immunoglobulin. Ordinarily, the antibody will contain both the light chain as well as at least the variable domain of a heavy chain. The antibody also may include the CH1, hinge, CH2, CH3, and CH4 regions of the heavy chain.

Methods for identifying the CDR regions of an antibody by analyzing the amino acid sequence of the antibody are well known (see, e.g., Wu, T. T. and Kabat, E. A. (1970) J. Exp. Med. 132: 211-250; Martin et al., Methods Enzymol. 203:121-53 (1991); Morea et al., Biophys Chem. 68(1-3): 9-16 (October 1997); Morea et al., J Mol. Biol. 275(2):269-94 (January 1998); Chothia et al., Nature 342(6252):877-83 (December 1989); Ponomarenko and Bourne, BMC Structural Biology 7:64 (2007).

As one non-limiting example, the following method can be used to identify the CDRs of an antibody.

For the CDR-L1, the CDR-L1 is approximately 10-17 amino acid residues in length. Generally, the start is at approximately residue 24 (the residue before the 24$^{th}$ residue is typically a cysteine. The CDR-L1 ends on the residue before a tryptophan residue. Typically, the sequence containing the tryptophan is either Trp-Tyr-Gln, Trp-Leu-Gln Trp-Phe-Gln, or Trp-Tyr-Leu, where the last residue within the CDR-L1 domain is the residue before the TRP in all of these sequences.

For the CDR-L2, the CDR-L2 is typically seven residues in length. Generally, the start of the CDR-L2 is approximately sixteen residues after the end of CDR-L1 and typically begins on the on the residue after the sequences of Ile-Tyr, Val-Tyr, Ile-Lys, or Ile-Phe.

For the CDR-L3, the CDR-L3 is typically 7-11 amino acid residues in length. Generally, the domain starts approximately 33 residues after the end of the CDR-L2 domain. The residue before the start of the domain is often a cysteine and the domain ends on the residue before Phe in the sequence Phe-Gly-XXX-Gly (where XXX is the three letter code of any single amino acid).

For the CDR-H1, the CDR-H1 domain is typically 10-12 amino acid residues in length and often starts on approximately residue 26. The domain typically starts four or five residues after a cysteine residue, and typically ends on the residue before a Trp (the Trp is often found in one of the following sequences: Trp-Val, Trp-Ile, or Trp-Ala. For the CDR-1-12, the CDR-H2 domain is typically 16 to 19 residues in length and typically starts 15 residues after the final residue of the CDR-H1 domain. The domain typically ends on the amino acid residue before the sequence Lys/Arg-Leu/Ile/Val/Phe/Thr/Ala-Thr/Ser/Ile/Ala (which includes, for example, the sequences Lys-Leu-Thr and Arg-Ala-Ala).

For the CDR-H3, the CDR-H3 domain is typically 3-25 amino acids in length and typically starts 33 amino acid residues after the final residues of the CDR-H2 domain (which is frequently two amino acid residues after a cysteine residue, e.g., a cysteine in the sequence Cys-Ala-Arg). The domain ends on the amino acid immediately before the Trp in the sequence Trp-Gly-XXX-Gly (where XXX is the three letter code of any single amino acid).

In one embodiment of the application, the antibody fragments are truncated chains (truncated at the carboxyl end). In certain embodiments, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dAb fragments (consisting of a VH domain); isolated CDR regions; (Fab')$_2$ fragments, bivalent fragments (comprising two Fab fragments linked by a disulphide bridge at the hinge region). The truncated chains can be produced by conventional biochemical techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce (Fab')$_2$ fragments. Single chain antibodies may be produced by joining VL- and VH-coding regions with a DNA that encodes a peptide linker connecting the VL and VH protein fragments.

"Fv" usually refers to the minimum antibody fragment that contains a complete antigen-recognition and -binding site. This region consists of a dimer of one heavy- and one light-chain variable domain (i.e., a VL domain and a VH domain) in tight, non-covalent association. It is in this configuration that the three CDRs of each variable domain interact to define an antigen-binding site on the surface of the $V_H$-$V_L$ dimer. Collectively, the CDRs confer antigen-binding specificity to the antibody. However, even a single variable domain (or half of an Fv comprising three CDRs specific for an antigen) has the ability to recognize and bind antigen, although likely at a lower affinity than the entire binding site. "Single-chain Fv" or "scFv" antibody fragments comprise the $V_H$ and $V_L$ domains of an antibody, wherein these domains are present in a single polypeptide chain. In certain embodiments, the Fv polypeptide further comprises a polypeptide linker between the $V_H$ and $V_L$ domains that enables the scFv to form the desired structure for antigen binding. For a review of scFv see Pluckthun in The Pharmacology of Monoclonal Antibodies, vol. 113, Rosenburg and Moore, eds. (Springer-Verlag: New York, 1994), pp. 269-315.

Papain digestion of an intact antibody produces two identical antigen-binding fragments, called "Fab" fragments, each with a single antigen-binding site, and a residual "Fc" fragment, whose name reflects its ability to crystallize readily. The Fab fragment contains the entire light chain (i.e., the constant domain (CL) and variable domain (VL) of the light chain) together with the first constant domain (CH1) and variable region (VH) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments that have hinge cysteines between them. For example, pepsin treatment of an antibody yields an $F(ab')_2$ fragment that has two antigen-combining sites and is still capable of cross-linking antigen. In other words, an $F(ab')_2$ fragment comprises two disulfide linked Fab fragments. Other chemical couplings of antibody fragments are also known. Thus, in certain embodiments, the antibodies of the invention may comprise 1, 2, 3, 4, 5, 6, or more CDRs that recognize or specifically bind to the E746-A750 deletion or that recognize or specifically bind to the L858R point mutation in EGFR. In some embodiments, the antibody of the invention that specifically binds to the EGFR E746-A750 deletion comprises a comprises at least one complementary determining region (CDR), wherein the CDR comprises a sequence selected from the group consisting of SEQ ID NO: 9, SEQ ID NO: 10, SEQ ID NO: 11, SEQ ID NO: 0.16, SEQ ID NO 17, and SEQ ID NO: 18. In some embodiments, the antibody of the invention that specifically binds to the EGFR L858R mutation com comprises at least one complementary determining region (CDR), wherein the CDR comprises an amino acid sequence selected from the group consisting of SEQ ID NO: 23, SEQ ID NO: 24, SEQ ID NO: 25, SEQ ID NO: 30, SEQ ID NO 31, and SEQ ID NO: 32.

Another type of antibody of the invention is an SMIP. SMIPs are a class of single-chain peptides engineered to include an antigen binding domain and effector domain (CH2 and CH3 domains). See, e.g., U.S. Patent Application Publication No. 20050238646. The antigen binding domain may be derived from the variable region or CDRs of an antibody, e.g., an EGFR L858R point mutation-specific antibody of the invention. Alternatively, the antigen is derived from a protein that specifically binds the indicated target (e.g., a non-immunoglobulin molecule that binds to the EGFR L858R mutant molecule).

Bispecific antibodies may be monoclonal, human or humanized antibodies that have binding specificities for at least two different antigens. In the present case, one of the binding specificities is for a target molecule of the invention (e.g., a EGFR L858R mutant or a EGFR E746-A750del mutant), the other one is for any other antigen, such as for example, a cell-surface protein or receptor or receptor sub-unit. Alternatively, a therapeutic agent may be placed on chain (e.g., a heavy chain) of the antibody. The therapeutic agent can be a drug, toxin, enzyme, DNA, radionuclide, etc.

In some embodiments, the antigen-binding fragment can be a diabody. The term "diabody" refers to a small antibody fragment with two antigen-binding sites, which fragment comprises a heavy-chain variable domain ($V_H$) connected to a light-chain variable domain ($V_L$) in the same polypeptide chain ($V_H$-$V_L$). They can be prepared by constructing scFv fragments with short linkers (about 5-10 residues) between the VH and VL domains such that inter-chain but not intra-chain pairing of the V domains is achieved, resulting in a multivalent fragment, i.e., a fragment having two antigen-binding sites. Since the linker is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

Camelid antibodies refer to a unique type of antibodies that are devoid of light chain, initially discovered from animals of the camelid family. The heavy chains of these so-called heavy-chain antibodies bind their antigen by one single domain, the variable domain of the heavy immunoglobulin chain, referred to as VHH. VHHs show homology with the variable domain of heavy chains of the human VHIII family. The VHHs obtained from an immunized camel, dromedary, or llama have a number of advantages, such as effective production in microorganisms such as *Saccharomyces cerevisiae*. In certain embodiments, single chain antibodies, and chimeric, humanized or primatized (CDR-grafted) antibodies, as well as chimeric or CDR-grafted single chain antibodies, comprising portions derived from different species, are also encompassed by the present disclosure as antigen-binding fragments of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., U.S. Pat. Nos. 4,816,567 and 6,331,415; U.S. Pat. No. 4,816,397; European Patent No. 0,120,694; WO 86/01533; European Patent No. 0,194,276 B1; U.S. Pat. No. 5,225,539; and European Patent No. 0,239,400 B1. See also, Newman et al., BioTechnology, 10: 1455-1460 (1992), regarding primatized antibody. See, e.g., Ladner et al., U.S. Pat. No. 4,946,778; and Bird et al., Science, 242: 423-426 (1988)), regarding single chain antibodies.

In addition, functional fragments of antibodies, including fragments of chimeric, humanized, primatized or single chain antibodies, can also be produced. Functional fragments of the subject antibodies retain at least one binding function and/or modulation function of the full-length antibody from which they are derived. Since the immunoglobulin-related genes contain separate functional regions, each having one or more distinct biological activities, the genes of the antibody fragments may be fused to functional regions from other genes (e.g., enzymes, U.S. Pat. No. 5,004,692, which is incorporated by reference in its entirety) to produce fusion proteins or conjugates having novel properties.

Non-immunoglobulin binding polypeptides are also contemplated. For example, CDRs from an antibody disclosed herein may be inserted into a suitable non-immunoglobulin scaffold to create a non-immunoglobulin binding agent. Suitable candidate scaffold structures may be derived from, for example, members of fibronectin type III and cadherin superfamilies.

Also contemplated are other equivalent non-antibody molecules, such as protein binding domains or aptamers, which specifically bind to a target molecule described herein (e.g., an EGFR mutant). See, e.g., Neuberger et al., Nature 312: 604 (1984). Aptamers are oligonucleic acid or peptide molecules that bind a specific target molecule. DNA or RNA aptamers are typically short oligonucleotides, engineered through repeated rounds of selection to bind to a molecular target. Peptide aptamers typically consist of a variable peptide loop attached at both ends to a protein scaffold. This double structural constraint generally increases the binding affinity of the peptide aptamer to levels comparable to an antibody (nanomolar range).

The invention also discloses the use of the antibodies with immunotoxins. Conjugates that are immunotoxins including antibodies have been widely described in the art. The toxins may be coupled to the antibodies by conventional coupling techniques or immunotoxins containing protein toxin portions can be produced as fusion proteins. In certain embodiments, antibody conjugates may comprise stable linkers and may release cytotoxic agents inside cells (see U.S. Pat. Nos. 6,867,007 and 6,884,869). The conjugates of the present application can be used in a corresponding way to obtain such immunotoxins. Illustrative of such immunotoxins are those described by Byers et al., Seminars Cell Biol 2:59-70 (1991) and by Fanger et al., Immunol Today 12:51-54 (1991). Exemplary immunotoxins include radiotherapeutic agents, ribosome-inactivating proteins (RIPs), chemotherapeutic agents, toxic peptides, or toxic proteins.

The specific antibodies disclosed in the invention may be used singly or in combination. The antibodies may also be used in an array format for high throughput uses. An antibody microarray is a collection of immobilized antibodies, typically spotted and fixed on a solid surface (such as glass, plastic and silicon chip).

In certain embodiments, the antibodies disclosed in the invention are especially indicated for diagnostic and therapeutic applications as described herein. Accordingly, the antibodies may be used in therapies, including combination therapies, in the diagnosis and prognosis of disease, as well as in the monitoring of disease progression. The invention, thus, further includes compositions comprising one or more embodiments of an antibody or an antigen binding portion of the invention as described herein. The composition may further comprise a pharmaceutically acceptable carrier. The composition may comprise two or more antibodies or antigen-binding portions, each with specificity for a different target site of the invention or two or more different antibodies or antigen-binding portions all of which are specific for the same site of the invention. A composition of the invention may comprise one or more antibodies or antigen-binding portions of the invention and one or more additional reagents, diagnostic agents or therapeutic agents.

The present application provides for the polynucleotide molecules encoding the antibodies and antibody fragments and their analogs described herein. Because of the degeneracy of the genetic code, a variety of nucleic acid sequences encode each antibody amino acid sequence. The desired nucleic acid sequences can be produced by de novo solid-phase DNA synthesis or by PCR mutagenesis of an earlier prepared variant of the desired polynucleotide. In one embodiment, the codons that are used comprise those that are typical for human or mouse (see, e.g., Nakamura, Y., Nucleic Acids Res. 28: 292 (2000)).

The binding agents of the present invention include the antibodies having the amino acid sequences set forth herein (whether or not including a leader sequence), and binding agent that may comprise at least six contiguous amino acids encompassing the amino acid sequence of one or more CDR domains (either from the heavy chain or the light chain, or both) of the invention, as well as polypeptides that are at least 90% identical, or at least 95% identical, or at least 96%, 97%, 98% or 99% identical to those described above (e.g., 90% identical, or at least 95% identical, or at least 96%, 97%, 98% or 99% identical to SEQ ID NO: 9, SEQ ID NO: 10, SEQ ID NO: 11, SEQ ID NO: 16, SEQ ID NO 17, SEQ ID NO: 18, SEQ ID NO: 23, SEQ ID NO: 24, SEQ ID NO: 25, SEQ ID NO: 30, SEQ ID NO 31 or SEQ ID NO: 32.

By "% identical" (or "% identity") for two polypeptides or two polynucleotides is intended a similarity score produced by comparing the amino acid sequences of the two polypeptides or by comparing the nucleotides sequences of the two polynucleotides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2: 482-489 (1981)) to find the best segment of similarity between two sequences.

In one non-limiting example, a polypeptide having an amino acid sequence that is at least, for example, 95% identical to a reference amino acid sequence of a polypeptide binding agent of the invention is intended that the amino acid sequence of the polypeptide is identical to the reference sequence except that the polypeptide sequence may include up to five amino acid alterations per each 100 amino acids of the reference amino acid sequence. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Similarly, a polynucleotide having a nucleotide sequence at least, for example, 95% "identical" to a reference nucleotide sequence encoding a binding agent of the invention means that the nucleotide sequence of the polynucleotide is identical to the reference sequence except that the polynucleotide sequence may include up to five point mutations per each 100 nucleotides of the reference nucleotide sequence encoding the binding agent or antibody of the invention. For example, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' terminal positions of the reference nucleotide sequence or anywhere between those terminal positions, interspersed either individually among nucleotides in the reference sequence or in one or more contiguous groups within the reference sequence.

When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence or reference nucleotide sequence and that gaps in homology of up to 5% of the total number of amino acid residues (in a polypeptide) or nucleotide residues (in a polynucleotide) in the reference sequence are allowed.

In further aspects, the invention provides a polynucleotide encoding a binding agent that specifically binds to an epidermal growth factor receptor (EGFR) molecule comprising a point mutation substituting leucine with arginine at position 858 or a binding agent that specifically binds an epidermal growth factor receptor (EGFR) molecule comprising a deletion at position E746-A750.

The terms "polynucleotide," "nucleic acid molecule," and "nucleic acid sequence" are used interchangeably herein to refer to polymers of nucleotides of any length, and include, without limitation, DNA, RNA, DNA/RNA hybrids, and modifications thereof. Unless otherwise specified, where the nucleotide sequence is provided, the nucleotides are set forth in a 5' to 3' orientation. Thus, the nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR.sub.2 ("amidate"), P(O)R, P(O)OR', CO or CH.sub.2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The present application also provides the polynucleotide molecules encoding analogs of the binding agents (e.g., antibodies) described herein. Because of the degeneracy of the genetic code, a number of different nucleic acid sequences may encode each antibody amino acid sequence. The desired nucleic acid sequences can be produced by de novo solid-phase DNA synthesis or by PCR mutagenesis of an earlier prepared variant of the desired polynucleotide. In one embodiment, the codons that are used comprise those that are typical for human, rabbit, or mouse (see, e.g., Nakamura, Y., Nucleic Acids Res. 28: 292 (2000)).

In additional, the present invention provides, in part, isolated polynucleotides that encode a binding agent of the invention, nucleotide probes that hybridize to such polynucleotides, and methods, vectors, and host cells for utilizing such polynucleotides to produce recombinant fusion polypeptides. Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were determined using an automated peptide sequencer. As is known in the art for any DNA sequence determined by this automated approach, any nucleotide sequence determined herein may contain some errors. Nucleotide sequences determined by automation are typically at least about 90% identical, and more typically at least about 95% to about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion. Unless otherwise indicated, each nucleotide sequence set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO: 1 or set forth using deoxyribonucleotide abbreviations is intended to indicate an RNA molecule having a sequence in which each deoxyribonucleotide A, G or C of SEQ ID NO: 1 has been replaced by the corresponding ribonucleotide A, G or C, and each deoxyribonucleotide T has been replaced by a ribonucleotide U.

In some embodiments, the invention provides an isolated polynucleotide (or an isolated polynucleotide complementary thereto) comprising a nucleotide sequence at least about 95% identical to a sequence comprising the sequence of SEQ ID NO: 1, SEQ ID NO: 3, SEQ ID NO: 5, or SEQ ID NO: 7. In some embodiments, the invention provides an isolated polynucleotide (or an isolated polynucleotide complementary thereto) comprising a nucleotide sequence at least about 95% identical to nucleotide sequence encoding an antibody (or fragment thereof) comprising the amino acid sequence of SEQ ID NO: 2, SEQ ID NO: 4, SEQ ID NO: 6, SEQ ID NO: 8, SEQ ID NO: 9, SEQ ID NO: 10, SEQ ID NO: 11, SEQ ID NO: 16, SEQ ID NO 17, SEQ ID NO: 18, SEQ ID NO: 23, SEQ ID NO: 24, SEQ ID NO: 25, SEQ ID NO: 30, SEQ ID NO 31, or SEQ ID NO: 32.

Using the information provided herein, such as the nucleotide sequences set forth in SEQ ID NOs: 1, 3, 5, or 7, a nucleic acid molecule of the present invention encoding a polypeptide binding agent (e.g., an antibody) of the invention may be obtained using standard cloning and screening procedures, such as those for cloning cDNAs using mRNA as starting material.

As indicated, the present invention provides, in part, a full-length antibody. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides, in part, nucleotide sequences encoding an intact antibody (e.g., comprising two heavy and two light chains) having the nucleotide sequence set forth in SEQ ID NOs: 1, 3, 5, or 7, with additional nucleic acid residues located 5' to the 5'-terminal residues of SEQ ID NOs: 1, 3, 5, or 7 and encodes the amino acid sequence of an intact antibody chains having the amino acid sequence set forth in SEQ ID NOs: 2, 4, 6, or 8 with additional amino acid residues located N-terminally to the N-terminal residue of SEQ ID NOs. 2, 4, 6, or 8. Likewise, the invention provides nucleotide sequences encoding CDRs, with additional nucleic acid residues located 5' to the 5'-terminal residues of a polynucleotide that encodes a CDR of the invention (e.g., a CDR comprising the amino acid sequence set forth in SEQ ID NO: 9, SEQ ID NO: 10, SEQ ID NO: 11, SEQ ID NO: 16, SEQ ID NO 17, SEQ ID NO: 18, SEQ ID NO: 23, SEQ ID NO: 24, SEQ ID NO: 25, SEQ ID NO: 30, SEQ ID NO 31, or SEQ ID NO: 32).

In some embodiments, the antibody-encoding or binding agent-encoding polynucleotide comprises the nucleotide sequence set forth in SEQ ID NOs: 1, 3, 5, or 7. In some embodiments, the antibody-encoding or binding agent-encoding polynucleotide comprises a nucleotide sequence that encodes a CDR having the amino acid sequence set forth in SEQ ID NO: 9, SEQ ID NO: 10, SEQ ID NO: 11, SEQ ID NO: 16, SEQ ID NO 17, SEQ ID NO: 18, SEQ ID NO: 23, SEQ ID NO: 24, SEQ ID NO: 25, SEQ ID NO: 30, SEQ ID NO 31, or SEQ ID NO: 32. In some embodiments, the polynucleotide encodes a polypeptide having the amino acid sequence set forth in SEQ ID NOs: 2, 4, 6, or 8.

As indicated, polynucleotides of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

Isolated polynucleotides of the invention may be nucleic acid molecules, DNA or RNA, which have been removed from their native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Polynucleotides of the invention include the nucleic acid molecules having the sequences set forth in SEQ ID NOs: 1, 3, 5, and 7, nucleic acid molecules comprising the coding sequence for the antibodies and binding agents of the invention that comprise a sequence different from those described above but which, due to the degeneracy of the genetic code, still encode an antibody or binding agent of the invention. The genetic code is well known in the art, thus, it would be routine for one skilled in the art to generate such degenerate variants.

The invention further provides isolated polynucleotides comprising nucleotide sequences having a sequence complementary to one of the binding agent-encoding or antibody-encoding polynucleotides of the invention. Such isolated molecules, particularly DNA molecules, are useful as probes for gene mapping, by in situ hybridization with chromosomes, and for detecting expression of the antibody in tissue (e.g., human tissue), for instance, by Northern blot analysis.

In some embodiments, the binding agents (e.g., antibodies) of the invention are encoded by at least a portion of the nucleotide sequences set forth herein. As used herein, a "portion" or "fragment" means a sequence fragment comprising a number of contiguous amino acid residues (if a polypeptide fragment (which may also be referred to herein a peptide)) or a sequence fragment comprising a number of nucleotide residues (if a polynucleotide fragment) that is less than the number of such residues in the whole sequence (e.g., a 50 nucleotide sequence is a portion of a 100 nucleotide long sequence). In other words, fragment of an indicated molecule that is smaller than the indicated molecule. For example, the binding agent-encoding polynucleotides and/or the antibody-encoding polynucleotides of the invention may comprise portions of intron sequences that do not encode any amino acids in the resulting binding agent or antibody. A fragment of a polynucleotide may be at least about 15 nucleotides, or at least about 20 nucleotides, or at least about 30 nucleotides, or at least about 40 nucleotides in length, which are useful as diagnostic probes and primers as discussed herein. Of course, larger fragments of about 50-1500 nucleotides in length are also useful according to the present invention, as are fragments corresponding to most, if not all, of the antibody-encoding or binding agent-encoding nucleotide sequence of the cDNAs having sequences set forth herein. By "a fragment at least 20 nucleotides in length", for example, is meant fragments that include 20 or more contiguous nucleotides from the respective nucleotide sequences from which the fragments are derived.

Polynucleotide fragments are useful as nucleotide probes for use diagnostically according to conventional DNA hybridization techniques or for use as primers for amplification of a target sequence by the polymerase chain reaction (PCR), as described, for instance, in Molecular Cloning, A Laboratory Manual, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference. Of course, a polynucleotide which hybridizes only to a poly A sequence or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone). Generation of such DNA fragments is routine to the skilled artisan, and may be accomplished, by way of example, by restriction endonuclease cleavage or shearing by sonication of DNA obtainable from the cDNA clone described herein or synthesized according to the sequence disclosed herein. Alternatively, such fragments can be directly generated synthetically.

In another aspect, the invention provides an isolated polynucleotide (e.g., a nucleotide probe) that hybridizes under stringent conditions to a binding agent-encoding or a antibody-encoding polynucleotide of the invention. The term "stringent conditions" with respect to nucleotide sequence or nucleotide probe hybridization conditions is the "stringency" that occurs within a range from about $T_m$ minus 5° C. (i.e., 5° C. below the melting temperature ($T_m$) of the probe or sequence) to about 20° C. to 25° C. below $T_m$. Typical stringent conditions are: overnight incubation at 42° C. in a solution comprising: 50% formamide, 5×.SSC (750 mM NaCl, 75 mM trisodium citrate), 50 mM sodium phosphate (pH 7.6), 5×Denhardt's solution, 10% dextran sulfate, and 20 micrograms/ml denatured, sheared salmon sperm DNA, followed by washing the filters in 0.1×SSC at about 65° C. As will be understood by those of skill in the art, the stringency of hybridization may be altered in order to identify or detect identical or related polynucleotide sequences.

By a polynucleotide or nucleotide probe that hybridizes to a reference polynucleotide is intended that the polynucleotide or nucleotide probe (e.g., DNA, RNA, or a DNA-RNA hybrid) hybridizes along the entire length of the reference polynucleotide or hybridizes to a portion of the reference polynucleotide that is at least about 15 nucleotides (nt), or to at least about 20 nt, or to at least about 30 nt, or to about 30-70 nt of the reference polynucleotide. These nucleotide probes of the invention are useful as diagnostic probes and primers (e.g. for PCR) as discussed herein.

Of course, polynucleotides hybridizing to a larger portion of the reference polynucleotide, for instance, a portion 50-750 nt in length, or even to the entire length of the reference polynucleotide, are useful as probes according to the present invention, as are polynucleotides corresponding to most, if not all, of the nucleotide sequence of the cDNAs described herein or the nucleotide sequences set forth in SEQ ID NOs: 1, 3, 5, and 7.

As indicated, nucleic acid molecules of the present invention, which encode a binding agent of the invention, may include but are not limited to those encoding the amino acid sequence of the mature intact polypeptide, by itself; fragments thereof; the coding sequence for the mature polypeptide and additional sequences, such as those encoding the leader or secretory sequence, such as a pre-, or pro- or pre-pro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide that facilitates purification of the fused polypeptide. In certain embodiments of this aspect of the invention, the marker amino acid sequence is a hexa-histidine peptide, such as the tag provided in a pQE vector (Qiagen, Inc.), among others, many of which are commercially available. As described in Gentz et al., Proc. Natl. Acad. Sci. USA 86: 821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., Cell 37: 767 (1984). As discussed below, other such fusion proteins include the binding agents and/or antibodies of the invention fused to an Fc domain at the N- or C-terminus.

The present invention further relates to variants of the nucleic acid molecules of the present invention, which encode portions, analogs or derivatives of a binding agent or antibody disclosed herein. Variants may occur naturally, such as a natural allelic variant. By an "allelic variant" is intended one of several alternate forms of a gene occupying a given locus on a chromosome of an organism. See, e.g. Genes II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Some alterations included in the invention are silent substitutions, additions and deletions, which do not alter the properties and activities (e.g. specific binding activity) of the binding agent and/or antibody disclosed herein.

Further embodiments of the invention include isolated polynucleotides comprising a nucleotide sequence at least 90% identical. In some embodiments of the invention the nucleotide is at least 95%, 96%, 97%, 98% or 99% identical, to a binding agent-encoding or antibody-encoding polynucleotide of the invention.

As a practical matter, whether any particular nucleic acid molecule is at least 90%, 95%, 96%, 97%, 98% or 99% identical to, for instance, the nucleotide sequences set forth in SEQ ID NOs: 1, 3, 5, and 7 or to the nucleotide sequence of the cDNA clones encoding the CDRs described herein can be determined conventionally using known computer programs such as the Bestfit program (Wisconsin Sequence Analysis Package, Version 8 for Unix, Genetics Computer Group, University Research Park, 575 Science Drive, Madison, Wis. 53711.

Due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the cDNAs described herein, to the nucleic acid sequences set forth in SEQ ID NOs: 1, 3, 5, or 7 or to nucleic acid sequences encoding the amino acid sequences set forth in SEQ ID NOs: 2, 4, 6, 8, 9, 10, 11, 16, 17, 18, 23, 24, 25, 30, 31, or 32 will encode a polypeptide having specific binding activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide that retains the specific binding activity of the reference binding agent or antibody of the invention. This is because the skilled artisan is fully aware of amino acid substitutions that are either less likely or not likely to significantly effect protein function (e.g., replacing one aliphatic amino acid with a second aliphatic amino acid). For example, guidance concerning how to make phenotypically silent amino acid substitutions is provided in Bowie et al., "Deciphering the Message in Protein Sequences: Tolerance to Amino Acid Substitutions," Science 247: 1306-1310 (1990), which describes two main approaches for studying the tolerance of an amino acid sequence to change. Skilled artisans familiar with such techniques also appreciate which amino acid changes are likely to be permissive at a certain position of the protein. For example, most buried amino acid residues require non-polar side chains, whereas few features of surface side chains are generally conserved. Other such phenotypically silent substitutions are described in Bowie et al., supra., and the references cited therein.

Methods for DNA sequencing that are well known and generally available in the art may be used to practice any polynucleotide embodiments of the invention. The methods may employ such enzymes as the Klenow fragment of DNA polymerase I, SEQUENASE® (US Biochemical Corp, Cleveland, Ohio), Taq polymerase (Invitrogen), thermostable T7 polymerase (Amersham, Chicago, Ill.), or combinations of recombinant polymerases and proofreading exonucleases such as the ELONGASE Amplification System marketed by Gibco BRL (Gaithersburg, Md.). The process may be automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Applied Biosystems).

Polynucleotide sequences encoding a binding agent or antibody of the invention may be extended utilizing a partial nucleotide sequence and employing various methods known in the art to detect upstream sequences such as promoters and regulatory elements. For example, one method that may be employed, "restriction-site" PCR, uses universal primers to retrieve unknown sequence adjacent to a known locus (Sarkar, G., PCR Methods Applic. 2: 318-322 (1993)). In particular, genomic DNA is first amplified in the presence of primer to linker sequence and a primer specific to the known region. Exemplary primers are those described in Example 4 herein. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia et al., Nucleic Acids Res. 16: 8186 (1988)). The primers may be designed using OLIGO 4.06 Primer Analysis software (National Biosciences Inc., Plymouth, Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom et al., PCR Methods Applic. 1: 111-119 (1991)). In this method, multiple restriction enzyme digestions and ligations may also be used to place an engineered double-stranded sequence into an unknown portion of the DNA molecule before performing PCR. Another method which may be used to retrieve unknown sequences is that described in Parker et al., Nucleic Acids Res. 19: 3055-3060 (1991)). Additionally, one may use PCR, nested primers, and PROMOTERFINDER®libraries to walk in genomic DNA (Clontech, Palo Alto, Calif.). This process avoids the need to screen libraries and is useful in finding intron/exon junctions.

When screening for full-length cDNAs, libraries that have been size-selected to include larger cDNAs may be used or random-primed libraries, which contain more sequences that contain the 5' regions of genes. A randomly primed library is useful for situations in which an oligo d(T) library does not yield a full-length cDNA. Genomic libraries may be useful for extension of sequence into the 5' and 3' non-transcribed regulatory regions.

Capillary electrophoresis systems, which are commercially available, may be used to analyze the size or confirm the nucleotide sequence of sequencing or PCR products. In particular, capillary sequencing may employ flowable polymers for electrophoretic separation, four different fluorescent dyes (one for each nucleotide) that are laser activated, and detection of the emitted wavelengths by a charge coupled device camera. Output/light intensity may be converted to electrical signal using appropriate software (e.g., GENOTYPER™ and SEQUENCE NAVIGATOR™, Applied Biosystems) and the entire process from loading of samples to computer analysis and electronic data display may be computer controlled. Capillary electrophoresis is useful for the sequencing of small pieces of DNA that might be present in limited amounts in a particular sample.

The present invention also provides recombinant vectors (e.g., an expression vectors) that comprise an isolated polynucleotide of the present invention, host cells into which is introduced the recombinant vectors (i.e., such that the host cells comprise the polynucleotide and/or comprise a vector comprising the polynucleotide), and the production of recombinant binding agent polypeptides (e.g., antibodies) or fragments thereof by recombinant techniques.

As used herein, a "vector" is any construct capable of delivering one or more polynucleotide(s) of interest to a host cell when the vector is introduced to the host cell. An "expression vector" is capable of delivering and expressing the one or more polynucleotide(s) of interest as encoded polypeptide in a host cell introduced with the expression vector. Thus, in an expression vector, the polynucleotide of interest is positioned for expression in the vector by being operably linked with regulatory elements such as a promoter, enhancer, polyA tail, etc., either within the vector or in the genome of the host cell at or near or flanking the integration site of the polynucleotide of interest such that the polynucleotide of interest will be translated in the host cell introduced with the expression vector. By "introduced" is meant that a vector is inserted into the host cell by any means including, without limitation, electroporation, fusion with a vector-containing liposomes, chemical transfection (e.g., DEAE-dextran), transformation, transvection, and infection and/or transduction (e.g., with recombinant virus). Thus, non-limiting examples of vectors include viral vectors (which can be used to generate recombinant virus), naked DNA or RNA, plasmids, cosmids, phage vectors, and DNA or RNA expression vectors associated with cationic condensing agents.

In some embodiments, the polynucleotide of the invention (e.g., encoding a EGFR mutant-specific binding agent) may be introduced using a viral expression system (e.g., vaccinia or other pox virus, retrovirus, or adenovirus), which may involve the use of a non-pathogenic (defective), replication competent virus, or may use a replication defective virus. In the latter case, viral propagation generally will occur only in complementing virus packaging cells. Suitable systems are disclosed, for example, in Fisher-Hoch et al., 1989, Proc. Natl. Acad. Sci. USA 86:317-321; Flexner et al., 1989, Ann. N.Y. Acad. Sci. 569:86-103; Flexner et al., 1990, Vaccine 8:17-21; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., 1991, Science 252:431-434; Kolls et al., 1994, Proc. Natl. Acad. Sci. USA 91:215-219; Kass-Eisler et al., 1993, Proc. Natl. Acad. Sci. USA 90:11498-11502; Guzman et al., 1993, Circulation 88:2838-2848; and Guzman et al., 1993, Cir. Res. 73:1202-1207. Techniques for incorporating DNA into such expression systems are well known to those of ordinary skill in the art. The DNA may also be "naked," as described, for example, in Ulmer et al., 1993, Science 259:1745-1749, and reviewed by Cohen, 1993, Science 259:1691-1692. The uptake of naked DNA may be increased by coating the DNA onto biodegradable beads, which are efficiently transported into the cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells. The invention may be practiced with vectors comprising cis-acting control regions to the polynucleotide of interest. Appropriate trans-acting factors may be supplied by the host, supplied by a complementing vector or supplied by the vector itself upon introduction into the host. In certain embodiments in this regard, the vectors provide for specific expression, which may be inducible and/or cell type-specific (e.g., those inducible by environmental factors that are easy to manipulate, such as temperature and nutrient additives).

The DNA insert comprising an antibody-encoding or binding agent-encoding polynucleotide of the invention should be operatively linked to an appropriate promoter, such as the phage lambda PL promoter, the E. coli lac, trp and tac promoters, the SV40 early and late promoters and promoters of retroviral LTRs, to name a few. Other suitable promoters are known to the skilled artisan. The expression constructs will further contain sites for transcription initiation, termination and, in the transcribed region, a ribosome binding site for translation. The coding portion of the mature transcripts expressed by the constructs may include a translation initiating at the beginning and a termination codon (UAA, UGA or UAG) appropriately positioned at the end of the polypeptide to be translated.

As indicated, the expression vectors may include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Non-limiting vectors for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Non-limiting eukaryotic vectors include pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Non-limiting bacterial promoters suitable for use in the present invention include the E. coli lad and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In the yeast, Saccharomyces cerevisiae, a number of vectors containing constitutive or inducible promoters such as alpha factor, alcohol oxidase, and PGH may be used. For reviews, see Ausubel et al. (1989) Current Protocols in Molecular Biology, John Wiley & Sons, New York, N.Y., and Grant et al., Methods Enzymol. 153: 516-544 (1997).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

Transcription of DNA encoding a binding agent or antibody of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at basepairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide (e.g., binding agent or antibody) may be expressed in a modified form, such as a fusion protein (e.g., a GST-fusion), and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

In one non-limiting example, a binding agent or antibody of the invention may comprise a heterologous region from an immunoglobulin that is useful to solubilize proteins. For example, EP-A-0 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5- has been fused with Fc portions for the purpose of high-throughput screening assays to identify antagonists of ML-5. See Bennett et al., Journal of Molecular Recognition 8: 52-58 (1995) and Johanson et al., The Journal of Biological Chemistry 270(16): 9459-9471 (1995).

The binding agents and antibodies can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In some embodiments, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Accordingly, in another embodiment, the invention provides a method for producing a recombinant binding agent or antibody by culturing a recombinant host cell (as described above) under conditions suitable for the expression of the fusion polypeptide and recovering the polypeptide. Culture conditions suitable for the growth of host cells and the expression of recombinant polypeptides from such cells are well known to those of skill in the art. See, e.g., Current Protocols in Molecular Biology, Ausubel F M et al., eds., Volume 2, Chapter 16, Wiley Interscience.

The invention also provides binding agent, particularly antibodies, that specifically bind to an epitope on a target molecule. Likewise, the invention provides epitopes useful for identifying the binding agents that specifically bind to a target molecule comprising the epitope. For example, as described herein, an epitope comprising the sequence (in a N' terminus to C-terminus order), threonine-serine-proline, is particularly useful identifying an antibody that will specifically bind to an epidermal growth factor receptor (EGFR) molecule comprising a deletion at position E746-A750.

Epitope mapping can be done using standard methods. For example, phage display is an in vitro selection technique in which a peptide is genetically fused to a coat protein of a bacteriophage resulting in display of a fused protein on the exterior of the virion. Biopanning of these virions by incubating the pool of phage displayed variants with a specific antibody of interest, which has been immobilized on a plate. The unbound phage is then washed away and the specifically bound phage is then eluted. The eluted phage is then amplified in E. coli and the process is repeated, resulting in enrichment of the phage pool in favor of the tightest binding sequences. An advantage of this technology is that it allows for the screening of greater than $10^9$ sequences in an unbiased way. Phage display is especially useful if the immunogen is unknown or a large protein fragment.

One of the limitations to phage display includes cross contamination between phage particles. Cross contamination between phage particles may enrich for sequences that do not specifically bind the antibody. Additionally, sequences that are not found in nature will be present in the phage displayed peptide library. These sequences may not resemble the immunizing peptide at all and may bind tightly to the antibody of interest. Retrieving sequences that do not resemble the immunizing peptide can be very confounding and it is difficult to decipher whether these peptides are contamination or unnatural peptides with high binding affinity to the antibody of interest.

The binding agents of the present invention may be employed in various methods. For example, the binding agents of the invention may be used in any known assay method, such competitive binding assays, direct and indirect sandwich assays, and immunoprecipitation assays. Zola, Monoclonal Antibodies: A Manual of Techniques, pp. 147-158 (CRC Press, Inc. 1987). For use in in vitro assays, the binding agents may be detectably labeled (e.g., with a fluorophore such as FITC or phycoerythrin or with an enzyme substrate, such as a substrate for horse radish peroxidase) for easy detection. As discussed below, the binding agents of the invention may be used for in vivo diagnostic assays, such as in vivo imaging. In some embodiments, the antibody is labeled with a radionucleotide (such as $^3H$, $^{111}In$, $^{14}C$, $^{32}P$, or $^{123}I$) so that the cells or tissue of interest can be localized using immunoscintiography. Methods of conjugating labels to a binding agent (such as an antibody) are known in the art. In other embodiments of the invention, binding agents of the invention need not be labeled, and the presence thereof can be detected using a labeled antibody, which binds to the binding agent of the invention. The antibody may also be used as staining reagent in pathology, following techniques well known in the art.

The invention also provides immortalized cell lines that produce an antibody of the invention. For example, hybridoma clones, constructed as described above, that produce monoclonal antibodies to the targeted sties disclosed herein are also provided. Similarly, the invention includes recombinant cells producing an antibody of the invention, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., Antibody Engineering Protocols, 1995, Humana Press, Sudhir Paul editor.).

In another aspect, the invention provides a method for making specific antibodies.

Polyclonal antibodies of the invention may be produced according to standard techniques by immunizing a suitable animal (e.g., rabbit, goat, etc.), collecting immune serum from the animal, and separating the polyclonal antibodies from the immune serum, in accordance with known procedures and screening and isolating a polyclonal antibody specific for the site of interest as further described below. Methods for immunizing non-human animals such as mice, rats, sheep, goats, pigs, cattle and horses are well known in the art. See, e.g., Harlow and Lane, Antibodies: A Laboratory Manual, New York: Cold Spring Harbor Press, 1990.

The immunogen may be the full length protein or a peptide comprising the site of interest. In some embodiments the immunogen is a peptide of from 7 to 20 amino acids in length, such as about 8 to 17 amino acids in length. Peptide antigens suitable for producing antibodies of the invention may be designed, constructed and employed in accordance with well-known techniques. See, e.g., Antibodies: A Laboratory Manual, Chapter 5, p. 75-76, Harlow & Lane Eds., Cold Spring Harbor Laboratory (1988); Czernik, Methods In Enzymology, 201: 264-283 (1991); Merrifield, J. Am. Chem. Soc. 85: 21-49 (1962)).

In some embodiments the immunogen is administered with an adjuvant. Suitable adjuvants will be well known to those of skill in the art. Exemplary adjuvants include complete or incomplete Freund's adjuvant, RIBI (muramyl dipeptides) or ISCOM (immunostimulating complexes).

When the above-described methods are used for producing polyclonal antibodies, following immunization, the polyclonal antibodies which secreted into the bloodstream can be recovered using known techniques. Purified forms of these antibodies can, of course, be readily prepared by standard purification techniques, such as for example, affinity chromatography with Protein A, anti-immunoglobulin, or the antigen itself. In any case, in order to monitor the success of immunization, the antibody levels with respect to the antigen in serum will be monitored using standard techniques such as ELISA, RIA and the like.

Monoclonal antibodies of the invention may be produced by any of a number of means that are well-known in the art. In some embodiments, antibody-producing B cells are isolated from an animal immunized with a peptide antigen as described above. The B cells may be from the spleen, lymph nodes or peripheral blood. Individual B cells are isolated and screened as described below to identify cells producing an antibody of interest. Identified cells are then cultured to produce a monoclonal antibody of the invention.

Alternatively, a monoclonal antibody of the invention may be produced using standard hybridoma technology, in a hybridoma cell line according to the well-known technique of Kohler and Milstein. See Nature 265: 495-97 (1975); Kohler and Milstein, Eur. J. Immunol. 6: 511 (1976); see also, Current Protocols in Molecular Biology, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by any of a number of standard means. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Typically the antibody producing cell and the immortalized cell (such as but not limited to myeloma cells) with which it is fused are from the same species. Rabbit fusion hybridomas, for example, may be produced as described in U.S. Pat. No. 5,675,063, C. Knight, issued Oct. 7, 1997. The immortalized antibody producing cells, such as hybridoma cells, are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

The invention also encompasses antibody-producing cells and cell lines, such as hybridomas, as described above.

Polyclonal or monoclonal antibodies may also be obtained through in vitro immunization. For example, phage display techniques can be used to provide libraries containing a repertoire of antibodies with varying affinities for a particular antigen. Techniques for the identification of high affinity human antibodies from such libraries are described by Griffiths et al., (1994) EMBO J., 13:3245-3260; Nissim et al., ibid, pp. 692-698 and by Griffiths et al., ibid, 12:725-734, which are incorporated by reference. The antibodies may be produced recombinantly using methods well known in the art for example, according to the methods disclosed in U.S. Pat. No. 4,349,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.)

Once a desired antibody is identified, polynucleotides encoding the antibody, such as heavy, light chains or both (or single chains in the case of a single chain antibody) or portions thereof such as those encoding the variable region, may be cloned and isolated from antibody-producing cells using means that are well known in the art. For example, the antigen combining site of the monoclonal antibody can be cloned by PCR and single-chain antibodies produced as phage-displayed recombinant antibodies or soluble antibodies in *E. coli* (see, e.g., Antibody Engineering Protocols, 1995, Humana Press, Sudhir Paul editor.)

Accordingly, in a further aspect, the invention provides such polynucleotides encoding the heavy chain, the light chain, a variable region, a framework region or a CDR of an antibody of the invention. In some embodiments, the nucleic acids are operably linked to expression control sequences. The invention, thus, also provides vectors and expression control sequences useful for the recombinant expression of an antibody or antigen-binding portion thereof of the invention. Those of skill in the art will be able to choose vectors and expression systems that are suitable for the host cell in which the antibody or antigen-binding portion is to be expressed.

Monoclonal antibodies of the invention may be produced recombinantly by expressing the encoding nucleic acids in a suitable host cell under suitable conditions. Accordingly, the invention further provides host cells comprising the nucleic acids and vectors described above.

Monoclonal Fab fragments may also be produced in *Escherichia coli* by recombinant techniques known to those skilled in the art. See, e.g., W. Huse, Science 246: 1275-81 (1989); Mullinax et al., Proc. Nat'l Acad. Sci. 87: 8095 (1990).

If monoclonal antibodies of a single desired isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., Proc. Nat'l. Acad. Sci., 82: 8653 (1985); Spira et al., J. Immunol. Methods, 74: 307 (1984)). Alternatively, the isotype of a monoclonal antibody with desirable propertied can be changed using antibody engineering techniques that are well-known in the art.

Antibodies of the invention, whether polyclonal or monoclonal, may be screened for epitope specificity according to standard techniques. See, e.g., Czernik et al., Methods in Enzymology, 201: 264-283 (1991). Peptide competition assays may be carried out to confirm lack of reactivity with other epitopes. The antibodies may also be tested by Western blotting against cell preparations containing the parent signaling protein, e.g., cell lines over-expressing the parent protein, to confirm reactivity with the desired epitope/target.

In an exemplary embodiment, phage display libraries containing more than $10^{10}$ phage clones are used for high-throughput production of monoclonal antibodies and, for validation and quality control, high-throughput immunohistochemistry is utilized to screen the efficacy of these antibodies. Western blots, protein microarrays and flow cytometry can also be used in high-throughput screening of site-specific polyclonal or monoclonal antibodies of the present invention. See, e.g., Blow N., Nature, 447: 741-743 (2007).

Antibodies of the invention may exhibit some limited cross-reactivity to related epitopes in non-target proteins. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-target proteins is readily characterized by Western blotting alongside markers of known molecular weight.

In certain cases, polyclonal antisera may exhibit some undesirable general cross-reactivity which may be removed by further purification of antisera, e.g., over a phosphotyramine column.

Antibodies may be further characterized via immunohistochemical (IHC) staining using normal and diseased tissues. IHC may be carried out according to well-known techniques. See, e.g., Antibodies: A Laboratory Manual, Chapter 10, Harlow & Lane Eds., Cold Spring Harbor Laboratory (1988). Briefly, paraffin-embedded tissue (e.g., tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies may be further characterized by flow cytometry carried out according to standard methods. See Chow et al., Cytometry (Communications in Clinical Cytometry) 46: 72-78 (2001). Briefly and by way of example, the following protocol for cytometric analysis may be employed: samples may be centrifuged on Ficoll gradients to remove lysed erythrocytes and cell debris. Adhering cells may be scrapped off plates and washed with PBS. Cells may then be fixed with 2% paraformaldehyde for 10 minutes at 37° C. followed by permeabilization in 90% methanol for 30 minutes on ice. Cells may then be stained with the primary antibody of the invention (, washed and labeled with a fluorescent-labeled secondary antibody. Additional fluorochrome-conjugated marker antibodies (e.g., CD45, CD34) may also be added at this time to aid in the subsequent identification of specific hematopoietic cell types. The cells would then be analyzed on a flow cytometer (e.g. a Beckman Coulter FC500) according to the specific protocols of the instrument used.

Binding agents of the invention may also be advantageously conjugated to fluorescent dyes (e.g. Alexa488, PE) for use in multi-parametric analyses along with other signal transduction (phospho-CrkL, phospho-Erk 1/2) and/or cell marker (CD34) antibodies. Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Antibody variable domains with the desired binding specificities (antibody-antigen combining sites) can be fused to immunoglobulin constant domain sequences. In certain embodiments, the fusion is with an immunoglobulin heavy-chain constant domain, including at least part of the hinge, CH2, and CH3 regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, for example, Suresh et al., Methods in Enzymology, 121:210 (1986); WO 96/27011; Brennan et al., Science 229:81 (1985); Shalaby et al., J. Exp. Med. 175:217-225 (1992); Kostelny et al., J. Immunol. 148(5):1547-1553 (1992); Hollinger et al., Proc. Natl. Acad. Sci. USA 90:6444-6448 (1993); Gruber et al., J. Immunol. 152:5368 (1994); and Tutt et al., J. Immunol. 147:60 (1991). Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. A strategy for making bispecific antibody fragments by the use of single-chain Fv (scFv) dimers has also been reported. See Gruber et al., J. Immunol., 152:5368 (1994). Alternatively, the antibodies can be "linear antibodies" as described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

To produce the chimeric antibodies, the portions derived from two different species (e.g., human constant region and murine variable or binding region) can be joined together chemically by conventional techniques or can be prepared as single contiguous proteins using genetic engineering techniques. The DNA molecules encoding the proteins of both the light chain and heavy chain portions of the chimeric antibody can be expressed as contiguous proteins. The method of making chimeric antibodies is disclosed in U.S. Pat. No. 5,677,427; U.S. Pat. No. 6,120,767; and U.S. Pat. No. 6,329,508, each of which is incorporated by reference in its entirety.

Fully human antibodies may be produced by a variety of techniques. One example is trioma methodology. The basic approach and an exemplary cell fusion partner, SPAZ-4, for use in this approach have been described by Oestberg et al., Hybridoma 2:361-367 (1983); Oestberg, U.S. Pat. No. 4,634,664; and Engleman et al., U.S. Pat. No. 4,634,666 (each of which is incorporated by reference in its entirety).

Human antibodies can also be produced from non-human transgenic animals having transgenes encoding at least a segment of the human immunoglobulin locus. The production and properties of animals having these properties are described in detail by, see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety.

Various recombinant antibody library technologies may also be utilized to produce fully human antibodies. For example, one approach is to screen a DNA library from human B cells according to the general protocol outlined by Huse et al., Science 246:1275-1281 (1989). The protocol described by Huse is rendered more efficient in combination with phage-display technology. See, e.g., Dower et al., WO 91/17271 and McCafferty et al., WO 92/01047; U.S. Pat. No. 5,969,108, (each of which is incorporated by reference in its entirety).

Eukaryotic ribosome can also be used as means to display a library of antibodies and isolate the binding human antibodies by screening against the target antigen, as described in Coia G, et al., J. Immunol. Methods 1: 254 (1-2):191-7 (2001); Hanes J. et al., Nat. Biotechnol. 18(12):1287-92 (2000); Proc. Natl. Acad. Sci. U.S.A. 95(24):14130-5 (1998); Proc. Natl. Acad. Sci. U.S.A. 94(10):4937-42 (1997), each which is incorporated by reference in its entirety.

The yeast system is also suitable for screening mammalian cell-surface or secreted proteins, such as antibodies. Antibody libraries may be displayed on the surface of yeast cells for the purpose of obtaining the human antibodies against a target antigen. This approach is described by Yeung, et al., Biotechnol. Prog. 18(2):212-20 (2002); Boeder, E. T., et al., Nat. Biotechnol. 15(6):553-7 (1997), each of which is herein incorporated by reference in its entirety. Alternatively, human antibody libraries may be expressed intracellularly and screened via the yeast two-hybrid system (WO0200729A2, which is incorporated by reference in its entirety).

Recombinant DNA techniques can be used to produce the recombinant specific antibodies described herein, as well as the chimeric or humanized antibodies, or any other genetically-altered antibodies and the fragments or conjugate thereof in any expression systems including both prokaryotic and eukaryotic expression systems, such as bacteria, yeast, insect cells, plant cells, mammalian cells (for example, NS0 cells).

Once produced, the whole antibodies, their dimers, individual light and heavy chains, or other immunoglobulin forms of the present application can be purified according to standard procedures of the art, including ammonium sulfate precipitation, affinity columns, column chromatography, gel electrophoresis and the like (see, generally, Scopes, R., Protein Purification (Springer-Verlag, N.Y., 1982)). Once purified, partially or to homogeneity as desired, the polypeptides may then be used therapeutically (including extracorporeally) or in developing and performing assay procedures, immunofluorescent staining, and the like. (See, generally, Immunological Methods, Vols. I and II (Lefkovits and Pernis, eds., Academic Press, NY, 1979 and 1981).

In another aspect, the invention provides methods for identifying a cancer that will respond favorably to a EGFR-targeted therapy. The methods comprise comprising (a) contacting a biological sample from the cancer with the binding agent that specifically binds to either to an epidermal growth factor receptor (EGFR) molecule comprising a deletion at position E746-A750 or to an EGFR molecule comprising a L858R point mutation to obtain an amount of binding and (b) comparing the result of step (a) with an amount of binding obtained by contacting a biological sample from a healthy individual with the binding agent, wherein a change in the amount of binding from the cancer as compared to the amount of binding from the healthy individual indicates the cancer will respond favorably to the EGFR-targeted therapy.

By "EGFR-targeted therapy" is meant any intervention, whether physical (e.g., surgery), or pharmaceutical (e.g., a compound that inhibits EGFR expression and/or activity) that that targets the EGFR molecule (or mutant thereof, such as the L858R mutant or the E746-A750del mutant) and is given as treatment to a patient (e.g., a human patient) suffering from a cancer or is suspected to be susceptible to a cancer characterized by aberrant expression of EGFR.

As used herein, by "aberrant expression of EGFR" in an individual or in a tissue is meant the overexpression or underexpression of wild-type EGFR, and/or expression of a mutant form of the molecule in a tissue as compared to that same tissue in a non-diseased individual. For example, expression in a tissue of an EGFR mutant (e.g., a EGFR L L858R mutant or the E746-A750del mutant) is aberrant expression of EGFR in that tissue. Similarly, an individual is said to aberrantly express EGFR if that individual expresses an EGFR molecule in a tissue where, in healthy individuals, EGFR is not expressed or is expressed in a different quantity in that same tissue type.

In some embodiments, the cancer is from a human patient. In some embodiments, the cancer is a non-small-cell lung cancer (NSCLC). In some embodiments, the cancer is an adenocarcinoma or a squamous cell carcinoma. In some embodiments, the cancer is of a tissue type selected from the group consisting of lung cancer, colon cancer, breast cancer, cervical cancer, pancreatic cancer, prostate cancer, stomach cancer, and esophageal cancer.

In various embodiments, the biological sample from the cancer and the biological sample from the healthy individual are of the same tissue type. Of course, the biological sample from the cancer will be, of course, cancerous (either malignant or benign), but the biological sample from the healthy individual may be of the same tissue type as that of the cancer. For example, where the cancer is an NSCLC, the biological sample from the healthy individual may be a lung tissue sample. Similarly, if the cancer is a adenocarcinoma from the pancreas, the biological sample from the healthy individual may be a pancreas tissue sample.

By "respond favorably" is meant that following treatment with a therapy that targets a molecule (e.g., an EGFR mutant-targeted therapy), a cancer (which may be benign or malignant) decreases in size (e.g., if a solid tumor), decreases in the number of neoplastic cells (e.g., if a non-solid tumor such as leukemia), does not increase in size (e.g., if a solid tumor), or does not increase in the number of neoplastic cells (e.g., if a non-solid tumor). The number of cancer cells can be counted in a blood sample using, for example, a hemacytometer. For solid tumors, size can be determined using calipers or, if the tumor is excised, by weighing the tumor on a scale.

As used herein, the term "biological sample" or "tissue sample" is used in its broadest sense, and means any biological sample suspected of containing a molecule of interest (e.g., an EGFR molecule or mutant thereof), and may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells, blood, urine, marrow, or a tissue, and the like.

Biological samples useful in the practice of the methods of the invention may be obtained from any mammal in which a cancer characterized by the presence of a molecule of interest is or might be present or developing. As used herein, the phrase "characterized by" with respect to a cancer and indicated molecule (e.g., aberrantly expressed EGFR, e.g., overexpressed EGFR or expression of an EGFR mutant) is meant a cancer in which the indicated molecule is aberrantly expressed, as compared to a cancerous or non-cancerous biological sample of the same tissue type in which the indicated molecule is not aberrantly expressed. The presence of the aberrantly expressed EGFR may drive (i.e., stimulate or be the causative agent of), in whole or in part, the growth and survival of such cancer.

Any biological sample comprising cells (or extracts of cells) from a mammalian cancer is suitable for use in the methods of the invention. In one embodiment, the biological sample comprises cells obtained from a tumor biopsy. The biopsy may be obtained, according to standard clinical techniques, from primary tumors occurring in an organ of a mammal, or by secondary tumors that have metastasized in other tissues. In another embodiment, the biological sample comprises cells obtained from a fine needle aspirate taken from a tumor, and techniques for obtaining such aspirates are well known in the art (see Cristallini et al., Acta Cytol. 36(3): 416-22 (1992))

Cellular extracts of the foregoing biological samples may be prepared, either crude or partially (or entirely) purified, in accordance with standard techniques, and used in the methods of the invention. Alternatively, biological samples comprising whole cells may be utilized in assay formats such as immunohistochemistry (IHC), flow cytometry (FC), and immunofluorescence (IF). Such whole-cell assays are advantageous in that they minimize manipulation of the tumor cell sample and thus reduce the risks of altering the in vivo signaling/activation state of the cells and/or introducing artifact signals. Whole cell assays are also advantageous because they characterize expression and signaling only in tumor cells, rather than a mixture of tumor and normal cells.

As used herein, an "individual," also referred to herein as a "subject," or "patient" is a vertebrate animal, such a mammal (e.g., a human. Mammals include, without limitation, to, farm animals (such as cows, pigs, and chicken), pets (such as cats, parrots, turtles, lizards, dogs, and horses), primates (such as chimpanzees and gorillas), zoo animals (such as mice and rats. The patient may or may not be afflicted with a condition (e.g., cancer) and/or may or may not presently show symptoms. In some embodiments, the subject has cancer. In some embodiments, the subject has a tumor or has had a tumor removed. It is understood that even if a tumor has been removed from a subject, tumor cells may nevertheless, in some instances, remain in the subject. For instance, although a tumor from one site may have been removed, the tumor may have metastasized and spread to other locations in the body. Also, although a tumor may have been removed from a subject, a portion of the tumor or some tumor cells may have been inadvertently or unavoidably left behind in the subject due to limitations in the surgical procedure or the like. In some embodiments, the subject is at risk of developing a tumor (or cancer). In some embodiments, the subject is undergoing or has undergone additional treatment (e.g., chemotherapy, surgery, hormone therapy, radiation, or additional immunotherapy).

Although present methods are primarily concerned with the treatment of human subjects, the disclosed methods may also be used for the treatment of other mammalian subjects such as dogs and cats for veterinary purposes.

In some embodiments, the methods for identifying a cancer that will respond favorably to an EGFR-targeted therapy may be carried out prior to preliminary blood evaluation or surgical surveillance procedures. Such a diagnostic assay may be employed to identify patients having EGFR expressed in a tissue where, in a non-diseased individual, there is normally no EGFR expressed. The aberrant EGFR-expressing patient may have cancer or be at risk for developing cancer, and is identified as a patient who is likely to respond favorably to EGFR-directed therapy.

The methods are applicable, for example, where biological samples are taken from a subject has not been previously diagnosed as having cancer, and/or has yet undergone treatment for cancer, and the method is employed to help diagnose the disease, or monitor the possible progression of the condition. For example, the methods are applicable where a subject patient has been previously diagnosed as having cancer, and possibly has already undergone treatment for the disease, and the method is employed to monitor the progression of the disease involving aberrant expression of EGFR.

The method of the invention may also be used to assess the risk of the subject patient from developing cancer (e.g., a patient with a familial history of cancer but who has yet to become symptomatic).

In another aspect, the invention provides a method of treating a patient having or suspected of having a cancer characterized by aberrant expression of EGFR, wherein the method comprising administering to the patient an effective amount of a binding agent that specifically binds to either to an epidermal growth factor receptor (EGFR) molecule comprising a deletion at position E746-A750 or to an EGFR molecule comprising a L858R point mutation, a polynucleotide encoding such a binding agent, a vector comprising such a polynucleotide, and/or compositions comprising the binding agent, polynucleotide, or vector. In some embodiments, the cancer is characterized by aberrant EGFR expression.

By "treating" is meant halting, retarding, or inhibiting progression of a cancer or preventing development of cancer in a patient. In some embodiments, the cancer is a cancer characterized by characterized by the presence of a molecule to which the administered binding agent specifically binds.

In some embodiments, the subject has a cancer aberrantly expressing the EGFR molecule (e.g., over- or under-expresses wt EGFR or expresses an EGFR mutant molecule such as the EGFR L858R mutant or the EGFR E746-A750 deletion mutant described herein) or has had such a tumor removed and/or a biopsy taken of such a tumor. In some embodiments, regression of the tumor, reduction in metastases, and/or reduction in tumor size or reduction in tumor cell count is induced by administration of the effective amount of a binding agent (or composition comprising the same) and/or a binding agent-encoding polynucleotide (or composition comprising the same).

As used herein, by an "effective amount" is an amount or dosage sufficient to effect beneficial or desired results including halting, slowing, halting, retarding, or inhibiting progression of a cancer in a patient or preventing development of cancer in a patient. An effective amount will vary depending upon, e.g., an age and a body weight of a subject to which the a binding agent, binding agent-encoding polynucleotide, vector comprising the polynucleotide and/or compositions thereof is to be administered, a severity of symptoms and a route of administration, and thus administration is determined on an individual basis. In general, the daily adult dosage for oral administration is about 0.1 to 1000 mg, given as a single dose or in divided doses. For continuous intravenous administration, the compositions can be administered in the range of 0.01 ug/kg/min to 1.0 ug/kg/min, desirably 0.025 ug/kg/min to 0.1 ug/kg/min.

Thus, in further aspects, the invention also provides a composition comprising a binding agent specifically binds to an epidermal growth factor receptor (EGFR) molecule comprising a point mutation substituting leucine with arginine at position 858, a binding agent that specifically binds to an epidermal growth factor receptor (EGFR) molecule comprising a deletion at position E746-A750, or both binding agents. In some embodiments, the composition further comprises a pharmaceutically acceptable carrier.

The invention also provides a composition comprising a polynucleotide encoding a binding agent specifically binds to an epidermal growth factor receptor (EGFR) molecule comprising a point mutation substituting leucine with arginine at position 858, a polynucleotide encoding a binding agent that specifically binds to an epidermal growth factor receptor (EGFR) molecule comprising a deletion at position E746-A750, or both polynucleotides or vectors containing the same. In some embodiments, the composition further comprises a pharmaceutically acceptable carrier.

An effective amount of a binding agent of the invention (e.g., an antibody), binding agent-encoding polynucleotide, vector containing such a polynucleotide, or compositions thereof can be administered in one or more administrations. By way of example, an effective amount of a binding agent, such as an EGFR L858R mutant-specific antibody or an EGFR E746-A750del-specific antibody, is an amount sufficient to ameliorate, stop, stabilize, reverse, slow and/or delay progression of a condition (e.g., a cancer characterized by aberrant EGFR expression) in a patient or is an amount sufficient to ameliorate, stop, stabilize, reverse, slow and/or delay growth of a cell (e.g., a biopsied cancer cell) in vitro. As is understood in the art, an effective amount of, for example, an EGFR L858R mutant-specific antibody or an EGFR E746-A750del-specific antibody may vary, depending on, inter alia, patient history as well as other factors such as the type (and/or dosage) of EGFR L858R mutant-specific antibody or EGFR E746-A750del-specific antibody used.

Effective amounts and schedules for administering the binding agents, binding agent-encoding polynucleotides, and/or compositions of the invention may be determined empirically, and making such determinations is within the skill in the art. Those skilled in the art will understand that the dosage that must be administered will vary depending on, for example, the mammal that will receive the binding agents, binding agent-encoding polynucleotides, and/or compositions of the invention, the route of administration, the particular type of binding agents, binding agent-encoding polynucleotides, and/or compositions of the invention used and other drugs being administered to the mammal. Where the patient is administered an antibody and/or a composition comprising an antibody, guidance in selecting appropriate doses for antibody is found in the literature on therapeutic uses of antibodies, e.g., Handbook of Monoclonal Antibodies, Ferrone et al., eds., Noges Publications, Park Ridge, N.J., 1985, ch. 22 and pp. 303-357; Smith et al., Antibodies in Human Diagnosis and Therapy, Haber et al., eds., Raven Press, New York, 1977, pp. 365-389.

A typical daily dosage of an effective amount of a binding agent used alone might range from about 1 ug/kg to up to 100 mg/kg of body weight or more per day, depending on the factors mentioned above. Generally, any of the following doses may be used: a dose of at least about 50 mg/kg body weight; at least about 10 mg/kg body weight; at least about 3 mg/kg body weight; at least about 1 mg/kg body weight; at least about 750 ug/kg body weight; at least about 500 ug/kg body weight; at least about 250 ug/kg body weight; at least about 100 ug/kg body weight; at least about 50 ug/kg body weight; at least about 10 ug/kg body weight; at least about 1 ug/kg body weight, or more, is administered. In some embodiments, a dose of a binding agent (e.g., antibody) provided herein is between about 0.01 mg/kg and about 50 mg/kg, between about 0.05 mg/kg and about 40 mg/kg, between about 0.1 mg and about 30 mg/kg, between about 0.1 mg and about 20 mg/kg, between about 0.5 mg and about 15 mg, or between about 1 mg and 10 mg. In some embodiments, the dose is between about 1 mg and 5 mg. In some alternative embodiments, the dose is between about 5 mg and 10 mg.

In some embodiments, the methods described herein further comprise the step of treating the subject with an additional form of therapy, and/or the compositions described herein further comprise additional agents directed toward additional therapy. In some embodiments, the additional form of therapy is an additional anti-cancer therapy (e.g., the composition may include an anti-cancer agent). In some embodiments the methods described herein further comprise the step of treating the subject with chemotherapy, radiation, surgery, hormone therapy, and/or additional immunotherapy. In some embodiments, the radiation is external beam radiation or teletherapy. In some alternative embodiments, the radiation is administered as internal therapy or brachytherapy. In some embodiments, the additional form of therapy comprises administration of one or more therapeutic agents, such as inhibitors of kinases. In some embodiments, the therapeutic agent is a therapeutic antibody, such as Avastin™, which is an anti-VEGF antibody, Herceptin™ (Trastuzumab) (Genentech, Calif.), which is an anti-HER2 antibody, Zenapax™ (daclizumab) (Roche Pharmaceuticals, Switzerland), which is an anti-CD25 antibody, and Rituxan™ (IDEC Pharm./Genentech, Roche/Zettyaku), which is an anti-CD20 antibody.

In some embodiments, the additional therapeutic agent is an angiogenesis inhibitor.

In some embodiments, the additional therapeutic agent is a cytotoxic compound. In some embodiments, the binding agents of the invention may also be used to target cancer cells for effector-mediated cell death. For example, the binding agents (e.g., antibodies) of the invention may directly kill the cancer cells through complement-mediated or antibody-dependent cellular cytotoxicity. The binding agents (e.g., antibodies) disclosed herein may also be administered as a fusion molecule joined to a cytotoxic moiety to directly kill cancer cells. The fusion can be achieved chemically or genetically (e.g., via expression as a single, fused molecule). As those skilled in the art will appreciate, for small molecules, chemical fusion is used, while for biological compounds, either chemical or genetic fusion can be used.

Non-limiting examples of cytotoxic compounds include therapeutic drugs, radiotherapeutic agents, ribosome-inactivating proteins (RIPs), chemotherapeutic agents, toxic peptides, toxic proteins, and mixtures thereof. Exemplary chemotherapeutic agents that may be attached to a binding agent or included in a composition of the invention include taxol, doxorubicin, docetaxel, prednisone, cisplatin, mitomycin, progesterone, tamoxifen, verapamil, podophyllotoxin, procarbazine, mechlorethamine, cyclophosphamide, camptothecin, ifosfamide, melphalan, chlorambucil, bisulfan, nitrosurea, dactinomycin, daunorubicin, bleomycin, plicomycin, etoposide (VP16), transplatinum, 5-fluorouracil, vincristin, vinblastin, or methotrexate.

In some embodiments, the addition therapeutic agent is an antinflammatory agent.

The cytotoxic drugs can be intracellularly acting cytotoxic drugs, such as short-range radiation emitters, including, for example, short-range, high-energy $\alpha$-emitters. Enzymatically active toxins and fragments thereof, including ribosome-inactivating proteins, are exemplified by saporin, luffin, momordins, ricin, trichosanthin, gelonin, abrin, etc. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Alternatively, the binding agent can be coupled to high energy radiation emitters, for example, a radioisotope, such as $^{131}$I, a $\gamma$-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", Monoclonal Antibodies for Cancer Detection and Therapy, Baldwin et al. (eds.), pp. 303-316 (Academic Press 1985), which is hereby incorporated by reference. Other suitable radioisotopes include $\alpha$-emitters, such as $^{212}$Bi, $^{213}$Bi, and $^{211}$At, and $\beta$-emitters, such as $^{186}$Re and $^{90}$Y.

The methods described herein (including therapeutic methods) and the compositions described herein can be administered by a single direct injection at a single time point or multiple time points to a single or multiple sites. Administration can also be nearly simultaneous to multiple sites. Frequency of administration may be determined and adjusted over the course of therapy, and is base on accomplishing desired results. In some cases, sustained continuous release formulations of binding agents (including antibodies), polynucleotides, and pharmaceutical compositions of the invention may be appropriate. Various formulations and devices for achieving sustained release are known in the art.

The binding agent (e.g., an antibody), binding agent-encoding polynucleotide, and/or vector containing such a polynucleotide or compositions containing any of these may be administered to the patient in a carrier, for example, a pharmaceutically-acceptable carrier. Thus, in further aspects, the invention provides a composition (e.g., a pharmaceutical composition) comprising a pharmaceutically acceptable carrier and (a) a binding agent of the invention, (b) a binding agent-encoding polynucleotide of the invention and/or (c) a vector comprising a binding agent-encoding polynucleotide.

As used herein, "pharmaceutically acceptable carrier" or "pharmaceutically acceptable excipient" includes any material which, when combined with an active ingredient, allows the ingredient to retain biological activity and is non-reactive with the subject's immune system and non-toxic to the subject when delivered. Examples include, but are not limited to, any of the standard pharmaceutical carriers such as a phosphate buffered saline solution, water, emulsions such as oil/water emulsion, and various types of wetting agents. Non-limiting examples of diluents for aerosol or parenteral administration are phosphate buffered saline, normal (0.9%) saline, Ringer's solution and dextrose solution. The pH of the solution may be from about 5 to about 8, or from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

While any suitable carrier known to those of ordinary skill in the art may be employed in the pharmaceutical compositions of this invention, the type of carrier will vary depending on the mode of administration. Numerous delivery techniques for the pharmaceutical compositions of the invention (i.e., containing a binding agent or a binding agent-encoding polynucleotide) are well known in the art, such as those described by Rolland, 1998, Crit. Rev. Therap. Drug Carrier Systems 15:143-198, and references cited therein.

Composition comprising a binding agent and/or a binding agent-encoding polynucleotide of the present invention may be formulated for any appropriate manner of administration, including for example, systemic, topical, oral, nasal, intravenous, intracranial, intraperitoneal, subcutaneous or intramuscular administration, or by other methods, such as infusion, which ensure its delivery to the bloodstream in an effective form. The composition may also be administered by isolated perfusion techniques, such as isolated tissue perfusion, to exert local therapeutic effects. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. In some embodiments, for oral administration, the formulation of the compositions is resistant to decomposition in the digestive tract, for example, as microcapsules encapsulating the binding agent (or binding agent-encoding polynucleotide or vector comprising such a polynucleotide) within liposomes. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Compositions of the invention may also comprise buffers (e.g., neutral buffered saline or phosphate buffered saline), carbohydrates (e.g., glucose, mannose, sucrose or dextran), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate.

In some embodiments, the binding agent and/or binding agent-encoding polynucleotide also may be entrapped in microcapsules prepared, for example, by coacervation techniques or by interfacial polymerization (for example, hydroxymethylcellulose or gelatin-microcapsules and poly (methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000. To increase the serum half life of the binding agent (e.g., an antibody), one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, and IgG4) that is responsible for increasing the in vivo serum half-life of the IgG molecule.

The binding agents (and/or binding agent-encoding polynucleotides) disclosed herein may also be formulated as liposomes. Liposomes containing the binding agents (and/or binding agent-encoding polynucleotides) are prepared by methods known in the art, such as described in Epstein et al., 1985, Proc. Natl. Acad. Sci. USA 82:3688; Hwang et al., 1980, Proc. Natl. Acad. Sci. USA 77:4030; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. In addition, where the binding agent is an antibody, antibodies (including antigen binding domain fragments such as Fab' fragments) can be conjugated to the liposomes as described in Martin et al., 1982, J. Biol. Chem. 257:286-288, via a disulfide interchange reaction. Administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions comprising a polynucleotide encoding a binding agent (e.g., an antibody) of the invention can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. (USA) (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 ug to about 2 mg, about 5 ug to about 500 ug, and about 20 ug to about 100 ug of DNA can also be used during a gene therapy protocol. The therapeutic polynucleotides and polypeptides of the present invention can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740; 4,777,127; GB Patent No. 2,200,651; and EP 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0 524 968. Additional approaches are described in Philip, Mol. Cell. Biol. (1994) 14:2411, and in Woffendin, Proc. Natl. Acad. Sci. (1994) 91:1581.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated.

The compositions of the invention include bulk drug compositions useful in the manufacture of non-pharmaceutical compositions (e.g., impure or non-sterile compositions) and pharmaceutical compositions (i.e., compositions that are suitable for administration to a subject or patient) which can be used in the preparation of unit dosage forms.

In yet another aspect, the invention provides kits for the detection of E746-A750 deletion or L858R point mutations in EGFR in a biological sample. The kit includes a binding agent that specifically binds to the E746-A750 deletion in EGFR and/or a binding agent that specifically binds to the L858R point mutations in EGFR; and b) instructions for detecting E746-A750 deletion or L858R point mutations in EGFR in a sample.

Antibodies and peptides of the invention may also be used within a kit for detecting the E746-A750 deletion or L858R point mutation in EGFR. Such a kit may further comprise a packaged combination of reagents in predetermined amounts with instructions for performing the diagnostic assay. Where the antibody is labeled with an enzyme, the kit will include substrates and co-factors required by the enzyme. In addition, other additives may be included such as stabilizers, buffers and the like. The relative amounts of the various reagents may be varied widely to provide for concentrations in solution of the reagents that substantially optimize the sensitivity of the assay. Particularly, the reagents may be provided as dry powders, usually lyophilized, including excipients that, on dissolution, will provide a reagent solution having the appropriate concentration.

In particular embodiments, the binding agents (e.g. antibodies) of the present application are attached to labeling moieties, such as a detectable marker. One or more detectable labels can be attached to the antibodies. Exemplary labeling moieties include radiopaque dyes, radiocontrast agents, fluorescent molecules, spin-labeled molecules, enzymes, or other labeling moieties of diagnostic value, particularly in radiologic or magnetic resonance imaging techniques.

A radiolabeled antibody in accordance with this disclosure can be used for in vitro diagnostic tests. The specific activity of an antibody, binding portion thereof, probe, or ligand, depends upon the half-life, the isotopic purity of the radioactive label, and how the label is incorporated into the biological agent. In immunoassay tests, the higher the specific activity, in general, the better the sensitivity. Radioisotopes useful as labels, e.g., for use in diagnostics, include iodine ($^{131}$I or $^{125}$I), indium ($^{111}$In), technetium ($^{99}$Tc), phosphorus ($^{32}$P), carbon ($^{14}$C), and tritium ($^{3}$H), or one of the therapeutic isotopes listed above.

Fluorophore and chromophore labeled biological agents can be prepared from standard moieties known in the art. Since antibodies and other proteins absorb light having wavelengths up to about 310 nm, the fluorescent moieties may be selected to have substantial absorption at wavelengths above 310 nm, such as for example, above 400 nm. A variety of suitable fluorescers and chromophores are described by Stryer, Science, 162:526 (1968) and Brand et al., Annual Review of Biochemistry, 41:843-868 (1972), which are hereby incorporated by reference. The antibodies can be labeled with fluorescent chromophore groups by conventional procedures such as those disclosed in U.S. Pat. Nos. 3,940,475, 4,289,747, and 4,376,110, which are hereby incorporated by reference.

The control may be parallel samples providing a basis for comparison, for example, biological samples drawn from a healthy subject, or biological samples drawn from healthy tissues of the same subject. Alternatively, the control may be a predetermined reference or threshold amount. If the subject is being treated with a therapeutic agent, and the progress of the treatment is monitored by the change in expression of a target of the invention, a control may be derived from biological samples drawn from the subject prior to, or during the course of the treatment.

In certain embodiments, binding agent conjugates for diagnostic use in the present application are intended for use in vitro, where the binding agent (e.g., an antibody) is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. In certain embodiments, secondary binding ligands are biotin and avidin or streptavidin compounds.

Binding agents (e.g., antibodies) of the invention may also be optimized for use in a flow cytometry (FC) assay to determine the rylation status of a target in subjects before, during, and after treatment with a therapeutic agent rein. For example, bone marrow cells or peripheral blood cells from patients may be analyzed by flow cytometry as well as for markers identifying various hematopoietic cell types. In this manner, activation status of the malignant cells may be specifically characterized. Flow cytometry may be carried out according to standard methods. See, e.g., Chow et al., Cytometry (Communications in Clinical Cytometry) 46: 72-78 (2001).

Alternatively, antibodies of the invention may be used in immunohistochemical (IHC) staining to detect differences in signal transduction or protein activity using normal and diseased tissues. IHC may be carried out according to well-known techniques. See, e.g., Antibodies: A Laboratory Manual, supra.

Peptides and antibodies of the invention may be also be optimized for use in other clinically-suitable applications, for example bead-based multiplex-type assays, such as IGEN, Luminex™ and/or Bioplex™ assay formats, or otherwise optimized for antibody arrays formats, such as reversed-phase array applications (see, e.g. Paweletz et al., Oncogene 20(16): 1981-89 (2001)). Accordingly, in another embodiment, the invention provides a method for the multiplex detection of the targets in a biological sample, the method comprising utilizing two or more binding agents of the invention.

In another aspect, the present application concerns immunoassays for binding, purifying, quantifying and otherwise generally detecting the target molecule. Thus, In various embodiments, the amount of binding is determined using an assay method including, without limitation, Western blotting, immunofluorescence, ELISA, IHC, flow cytometry, immunoprecipitation, autoradiography, scintillation counting, and chromatography.

Assays may be homogeneous assays or heterogeneous assays. In a homogeneous assay the immunological reaction usually involves an antibody of the invention, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be used include free radicals, radioisotopes, fluorescent dyes, enzymes, bacteriophages, coenzymes, and so forth. In a heterogeneous assay approach, the reagents are usually the specimen, an antibody of the invention, and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal using means for producing such signal. The signal is related to the presence of the analyte in the specimen. Means for producing a detectable signal include the use of radioactive labels, fluorescent labels, enzyme labels, and so forth.

Antibodies disclosed herein may be conjugated to a solid support suitable for a diagnostic assay (e.g., beads, plates, slides or wells formed from materials such as latex or polystyrene) in accordance with known techniques, such as precipitation. In certain embodiments, immunoassays are the various types of enzyme linked immunoabsorbent assays (ELISAs) and radioimmunoassays (RIA) known in the art. Immunohistochemical detection using tissue sections is also particularly useful. However, it will be readily appreciated that detection is not limited to such techniques, and Western blotting, dot and slot blotting, FACS analyses, and the like may also be used. The steps of various useful immunoassays have been described in the scientific literature, such as, e.g., Nakamura et al., in Enzyme Immunoassays: Heterogeneous and Homogeneous Systems, Chapter 27 (1987), incorporated herein by reference. In general, the detection of immunocomplex formation is well known in the art and may be achieved through the application of numerous approaches. These methods are based upon the detection of radioactive, fluorescent, biological or enzymatic tags. Of course, one may find additional advantages through the use of a secondary binding ligand such as a second antibody or a biotin/avidin ligand binding arrangement, as is known in the art. The antibody used in the detection may itself be conjugated to a detectable label, wherein one would then simply detect this label. The amount of the primary immune complexes in the composition would, thereby, be determined.

Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are washed extensively to remove any non-specifically bound labeled secondary antibodies or ligands, and the remaining label in the secondary immune complex is detected.

An enzyme linked immunoabsorbent assay (ELISA) is a type of binding assay. In one type of ELISA, antibodies disclosed herein are immobilized onto a selected surface exhibiting protein affinity, such as a well in a polystyrene microtiter plate. Then, a suspected neoplastic tissue sample is added to the wells. After binding and washing to remove non-specifically bound immune complexes, the bound target signaling protein may be detected.

In another type of ELISA, the neoplastic tissue samples are immobilized onto the well surface and then contacted with the site-specific antibodies disclosed herein. After binding and washing to remove non-specifically bound immune complexes, the bound antibodies are detected.

Irrespective of the format used, ELISAs have certain features in common, such as coating, incubating or binding, washing to remove non-specifically bound species, and detecting the bound immune complexes.

The radioimmunoassay (RIA) is an analytical technique which depends on the competition (affinity) of an antigen for antigen-binding sites on antibody molecules. Standard curves are constructed from data gathered from a series of samples each containing the same known concentration of labeled antigen, and various, but known, concentrations of unlabeled antigen. Antigens are labeled with a radioactive isotope tracer. The mixture is incubated in contact with an antibody. Then the free antigen is separated from the antibody and the antigen bound thereto. Then, by use of a suitable detector, such as a gamma or beta radiation detector, the percent of either the bound or free labeled antigen or both is determined. This procedure is repeated for a number of samples containing various known concentrations of unlabeled antigens and the results are plotted as a standard graph. The percent of bound tracer antigens is plotted as a function of the antigen concentration. Typically, as the total antigen concentration increases the relative amount of the tracer antigen bound to the antibody decreases. After the standard graph is prepared, it is thereafter used to determine the concentration of antigen in samples undergoing analysis.

In an analysis, the sample in which the concentration of antigen is to be determined is mixed with a known amount of tracer antigen. Tracer antigen is the same antigen known to be in the sample but which has been labeled with a suitable radioactive isotope. The sample with tracer is then incubated in contact with the antibody. Then it can be counted in a suitable detector which counts the free antigen remaining in the sample. The antigen bound to the antibody or immunoabsorbent may also be similarly counted. Then, from the standard curve, the concentration of antigen in the original sample is determined.

The following Examples are provided only to further illustrate the invention, and are not intended to limit its scope, except as provided in the claims appended hereto. The invention encompasses modifications and variations of the methods taught herein which would be obvious to one of ordinary skill in the art.

EXAMPLES

Example 1

Generation of RmAb

New Zealand Rabbits were immunized with synthetic peptides matching the EGFR sequence with E746-A750del or L858R mutations. For the EGFR E746-A750del, the amino acid sequence of the immunogen used was CKIP-VAIKTSPKANKE (SEQ ID NO: 53). For the EGFR L858R mutation, the amino acid of the immunogen used was CKITDFGRAKLLGAE (SEQ ID NO: 54). Note that for both of these immunogens, the N' terminal cysteine residue is not included in the sequence of EGFR—rather, this is a convenient docking point for the carrier, Keyhole limpet hemocyanin (KLH). Thus, the immunogenic portion of the immunogen was really KIPVAIKTSPKANKE (SEQ ID NO: 55) for the EGFR E746-A750del and KITDF-GRAKLLGAE (SEQ ID NO: 56) for the EGFR L858R. Positive immunoreactive rabbits were identified by Western blotting and preliminary IHC screening, and chosen for rabbit monoclonal preparation. Supernatants from newly generated clones were screened by ELISA for reactivity with the immunogen peptide.

Supernatants thus identified by ELISA having specificity for EGFR with E746-A750del or specificity for the EGFR L858R point mutation were next tested by Western blotting analysis of cell extracts made from cells known to harbor the EGFR with E746-A750del or the EGFR L858R point mutation. A panel of six human cancer cell lines expressing either wild type EGFR (wtEGFR) with/without amplification, or EGFR mutation E746-A750del or L858R were used. The H3255 cell line (EGFR amplification with L858R point mutation was provided by Dr. Lewis Cantley (Harvard Medical School, Boston, Mass.). The H1975 cell line (EGFR L858R point mutation) and the H1650 cell line (EGFR E746-A750del) were purchased from the American Type Culture Collection, Manassas, Va. ('ATCC')). The following cell lines, HCC827 (EGFR amplification with E746-A750del), Kyse450 (human esophageal squamous cell carcinoma cell line with wtEGFR with amplification) and Kyse70 (human esophageal squamous cell carcinoma cell line with wtEGFR without amplification) were obtained from the Deutsche Sammlung von Mikroorganismen and Zellkulturen GmbH in Braunschweig, Germany ('DSMZ').

For the Western blotting analysis, cultured cells were washed twice with cold 1×PBS and then lysed in 1× cell lysis buffer (20 mM Tris-HCL, pH 7.5, 150 mM NaCl, 1 mM Na2EDTA, 1 mM EGTA, 1% triton, 2.5 mM sodium pyrophosphate, 1 mM beta glycerophosphate, 1 mM Na3VO4, 1 ug/ml leupeptin) supplemented with Complete, Mini, EDTA-free protease inhibitor cocktail (Roche). Lysates were sonicated and centrifuged at 14000 rpm for 5 min. The protein concentration was measured using Coomassie protein assay reagent (Pierce Chemical Co., Rockford, Ill.). Equal amounts of total protein were resolved by 8% pre-cast Tris-Glycine gels (Invitrogen). Protein were blotted to nitrocellulose membranes and incubated overnight at 4° C. with the RmAb following standard methods protocols (see, e.g., Ausubel et al., supra). Specific binding was detected by HRP-conjugated species-specific secondary antibody and visualized by using LumiGLO development and exposed to x-ray film.

As shown in FIG. 1, while E746-A750del (dEGFR) RmAb only detects EGFR (E746-A750del) in HCC827 and H1650 cells, L858R RmAb detects EGFR (L858R) in H3255 and H1975 cells. These two mutation-specific antibodies do not react with EGFR in two human esophageal squamous cell carcinoma cell lines (Kyse450 and Kyse70) that contain wild type sequence for exon 19 (where the E746-A750 deletion occurs) and exon 21 (where the L858R point mutation occurs of EGFR. As expected, a control EGFR RmAb (clone 86) reacted with EGFR in all cases (see FIG. 1).

After hybridoma clones were selected, additional analysis was performed on the antibodies produced by the hybridoma including immunohistochemistry of cellular extracts made from the above-listed cells. Eventually, the clones were tested for the ability of the antibodies they produced to specifically bind their targets in such applications as flow cytometry and immunofluorescence. Clones that produced antibodies with the specificity sought were deposited with the ATCC on Apr. 10, 2009. The E746-A750del (dEGFR) RmAb-producing clone (clone 6B6F8B10) and EGFR (L858R)-producing clone (clone 43B2E11E5B2) were assigned ATCC No. PTA-9151 and ATCC No. PTA-9152, respectively.

Example 2

Immunocytochemistry

Next, fluorescence immunocytochemistry analysis was performed using the L858R, dEGFR, and control EGFR antibodies on slides of H3255, H1975, H1650, and HCC827 cell lines.

For fluorescence immunocytochemistry on cells, cell lines were grown in 8-well chamber slides (BD, Franklin Lakes, N.J.) to approximately 70% confluency. Cells were fixed with 4% formaldehyde (Polysciences, Warrington, Pa.) in PBS for 15 minutes at room temperature, rinsed in PBS (3×10 min), and then blocked in 5% normal goat serum (Sigma-Aldrich, St. Louis, Mo.) in PBS containing 0.3% Triton X-100 (Mallinckrodt Baker, Phillipsburg, N.J.) for one hour at room temperature. The blocking solution was aspirated from the chambers and cells were incubated overnight at 4° C. in primary antibodies diluted in PBS with 0.3% Triton and 1% BSA (American Bioanalytical, Natick, Mass.). Slides were rinsed in PBS (3×10 min) and then incubated for one hour at room temperature in AlexaFluor®488 conjugated goat anti-rabbit IgG secondary antibody (Invitrogen, Carlsbad, Calif.) diluted in PBS with 0.3% Triton and 1% BSA. Slides were rinsed in PBS as before, chambers were removed from the slides and they were cover-slipped with Prolong Gold antifade mounting medium (Invitrogen). Cells were imaged on a Nikon C1 confocal microscope.

Cell pellets of Kyse70 and Kyse450 cells were used as controls for both immunoflourescence and immunohistochemistry (IHC) analysis. (Note: Kyse70, and Kyse450 were paraffin-embedded for IHC analysis—see Example 3 and FIG. 3 below.)

Figure 2:
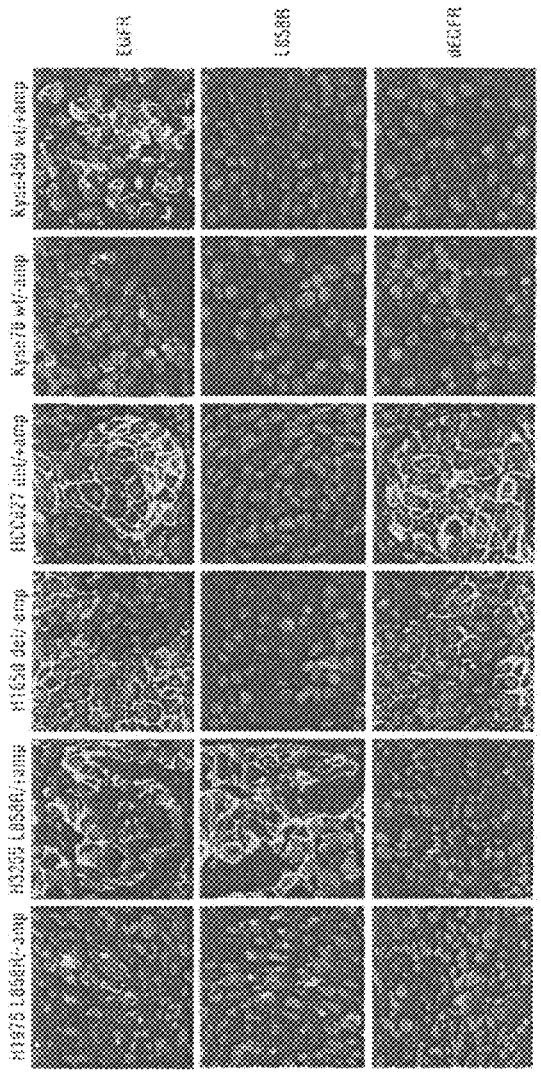
FIG. 2 depicts reactivity of the antibodies of the invention by immunofluorescent immunocytochemistry for EGFR and mutants thereof in the indicated cell lines. The control EGFR-specific antibody (top panel) stains (i.e., binds to) all six cell lines, regardless of their EGFR mutational status. The EGFR L858R-specific antibody stains only the cancer cells with the L858R point mutation in their EGFR molecule. Similarly, the dEGFR-specific antibody stains only the cancer cells with the deletion in Exon 19 (i.e., E746-A750) in their EGFR molecule.

As shown in FIG. 2, the wtEGFR-specific antibody stained all six cell lines regardless of their EGFR mutational status (top row). The L858R-specific antibody stained (i.e., specifically bound to) only the cancer cells with L858R point mutation (i.e., the H1975 and H3255 cells) (see FIG. 2, middle row). The dEGFR-specific antibody (i.e., the E746-A750del-specific antibody) stained only the cancer cells with E746_A750 mutant EGFR (i.e., the H1650 and HCC827 cells) (FIG. 2, bottom row).

Thus, the L858R-specific antibody was specific for its mutant EGFR (i.e., specifically bound to the EGFR mutant containing the L858R point mutation), and did not bind to either wildtype EGFR or the EGFR mutant containing the E746-A750 deletion. Similarly, the dEGFR-specific antibody was specific for its mutant EGFR (i.e., specifically bound to the EGFR mutant containing the E746-A750 deletion, and did not bind to either wildtype EGFR or the EGFR mutant containing the L858R point mutation.

Example 3

Immunohistochemistry on Xenografts

To test the specificity of binding of the rabbit monoclonal antibodies described in Example 1, xenografts were prepared of human cancer cells in nude mice.

For xenografts, H3255, H1975, H1650, and HCC827 cells were inoculated subcutaneously (s.c.) in the right thigh of nude (nu/nu) mice ($5 \times 10^6$ to $2 \times 10^7$ cells per mouse) and grown until a tumor diameter of about 10 mm was reached.

For immunofluorescence analysis, all analyses were performed on formalin-fixed, paraffin-embedded blocks. Serial 4-um-thick tissue sections were cut from TMAs for immunohistochemistry study. The slides were baked at 55° C. overnight, then deparaffinized in xylene and rehydrated through a graded series of ethanol concentrations. Antigen retrieval (microwave boiling for 10 minutes in 1 mM EDTA) was performed. Intrinsic peroxidase activity was blocked by 3% hydrogen peroxide for 10 min. 5% goat serum (Sigma) solution was used for blocking nonspecific antibody binding, and the optimally diluted primary antibodies were applied to cover the specimen. Slides were incubated at 4° C. overnight. After three washes in TBS-T for 5 minutes each, slides were incubated for 30 min with labeled polymer-HRP anti-rabbit secondary antibody at room temperature. Following three additional washes in TBS-T, slides were visualized using substrate-chromagen (Envision™+ kit, commercially available from Dako). Sections were scanned at low magnification. Intensity of the staining as well as percentage of positive cells was recorded. Stain intensity was scored from 0 to 3+, based on the, staining intensity and percentage of positive cells were recorded.

The staining intensity score was established as follows: 0 if tumor cells had complete absence of staining or faint staining intensity in less than 10%; 1+ if more than 10% of tumor cells had faint staining; 2+ if tumor cells had moderate staining; 3+ if tumor cells had strong staining. Tumors with 1+, 2+, and 3+ expression were interpreted as positive for dEGFR or L858R EGFR antibodies expression, and tumors with no expression (0 score) were interpreted as negative. The distribution of staining, membrane or cytoplasm, was also recorded and assessed at high magnification. Table 1 provides a summary of the staining scoring system.

TABLE 1

Scores of the Images

Mutant Antibodies (L858R and dEGFR)

| Positive | Negative |
| --- | --- |
| Moderate to strong cytoplasm and membrane staining in no more than 10% of tumor cells. | No staining or a faint/barely perceptible cytoplasm staining in less than 10% of tumor cells. |

Control EGFR and Pan-Keratin Antibodies

| Score | 1 | 2 | 3 |
| --- | --- | --- | --- |
| Intensity of staining | Weak staining | Moderate staining | Strong staining |

Figure 3:
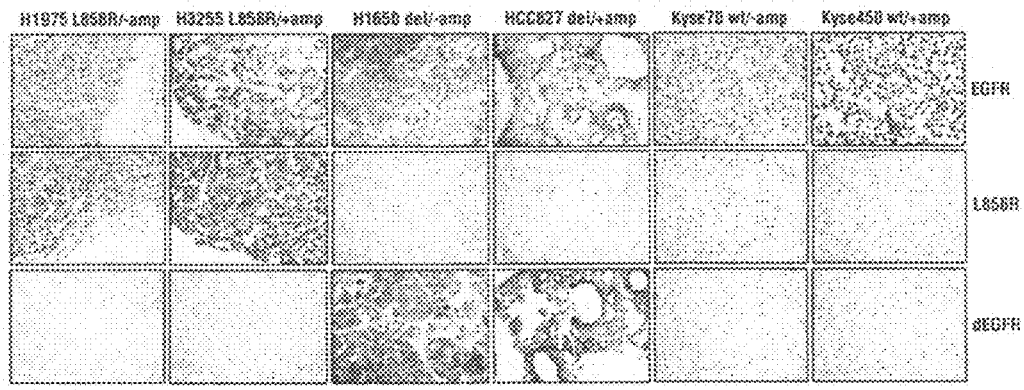
FIG. 3 depicts reactivity of the antibodies of the invention by immunohistochemistry for EGFR and mutants thereof in sections taken from nude mice implanted with the indicated cell lines as xenografts. The control EGFR-specific antibody (top panel) stains (i.e., binds to) all six cell lines, regardless of their EGFR mutational status. The EGFR L858R-specific antibody stains only the cancer cells with the L858R point mutation in their EGFR molecule. Similarly, the dEGFR-specific antibody stains only the cancer cells with the deletion in Exon 19 (i.e., E746-A750) in their EGFR molecule.

FIG. 3 provides the photographs of IHC staining of non-limiting, representative samples of H1975 (unamplified L858R mutation), H3255 (amplified L858R mutation), H1650 (unamplified E746-A750del mutation), HCC827 (amplified E746-A750del mutation), Kyse750 (unamplified wildtype EGFR), and Kyse 450 (amplified wildtype EGFR) xenografts using wildtype EGFR-specific antibody (top row), the EGFR L858R-specific antibody (middle row) and the EGFR dEGFR (i.e., the E746-A750del, which is also sometimes referred to a the del722-726, because)-specific antibody. Note that the EGFR E746-A750del mutation is sometimes referred to herein and in the scientific literature as the EGFR del722-726 (i.e., deletion of residues 722-726) because the numbering of the amino acid begins on the EGFR mutant that includes the signal sequence in the EGFR E746-A750del and does not include the signal sequence in the EGFR del722-726.

As shown in FIG. 3, paraffin-embedded xenografts demonstrated appropriate staining with control and mutation-specific antibodies. All cells were labeled (i.e., stained or bound) with the wtEGFR control antibody (FIG. 3, top row). The signal was localized to the plasma membrane and cytoplasm, as expected with a constitutively active EGF receptor. The fluorescence intensity was proportional to the presumptive EGFR expression level—cells with amplified expression (+amp) had brighter signal than those lower expression levels (−amp). Staining with mutation-specific antibodies was only seen in cancer cells and not in normal tissue, and its localization correlated with control EGFR antibody staining. The L858R-antibody only labeled (i.e., bound to) L858R-positive cells (H3255 and H1975, middle row) with higher intensity in H3255 xenograft where the high L858R EGFR expression is due to EGFR gene amplification. No binding of the L858R-specific antibody was seen in wild-type EGFR-expressing (Kyse450 and Kyse70) or deletion mutant (HCC827 and H1650) cells with the L858R-specific antibody. The deletion-specific antibody (i.e., the dEGFR-specific antibody) labeled only the cells expressing the EGFR deletion (HCC827 and H1650) and the intensity was higher in HCC827 cells bearing EGFR amplification (compare the middle two panels on the bottom row of FIG. 3). Wild type EGFR-expressing cells (i.e., Kyse450 and Kyse70) and L858R mutant (H3255 and H1975) cells were not labeled by the E746-A750 deletion-specific antibody (FIG. 3, bottom row).

Note that weak staining was observed with L858R-specific antibody in the HCC827 xenograft in areas of the tissue expressing high levels of EGFR. This is likely the result of cross-reactivity of 43B2 antibody with high levels of wild type EGFR. Similarly, weak staining (i.e., binding) of the EGFR E746-A750-specific (6B6F8B10) antibody was observed in H3255 and H1975 xenografts, which could be attributed to background staining due to the use of a suboptimal working concentration of this antibody.

Example 4

Immunohistochemistry (IHC) of Pre-Typed Human Tissues

The two EGFR mutation-specific antibodies described herein (i.e., the EGFR E746-A750-specific and the EGFR L858R-specific antibodies) were used in immunohistochemistry on EGFR genotyped NSCLC patient samples. These patients samples thus had known EGFR mutational status by DNA sequencing prior to being subjected to IHC analysis.

For these studies, all analyses were performed on formalin-fixed, paraffin blocks. Human samples of NSCLC paraffin blocks were provided by the pathological department of Second Xiangya Hospital, Central South University (Changsha, Hunan, P.R. China). These tissues were examined with hematoxyline and eosin to confirm histopathological diagnosis and selected as adequate specimens for further analysis. Immunohistochemistry by wild type EGFR antibody was used to screen for EGFR positive samples (++/+++ and +++/+++) for molecular studies.

For sequencing, hematoxylin and eosin-stained sections of formalin-fixed paraffin-embedded tissue were reviewed to identify regions of tissue comprising at least 50% tumor cells. Cases where tumor cells comprising less than 50% of the tissue, or where the amount of tumor tissue was limited, were excluded for unselected screen. Genomic DNA was isolated using the FormaPure kit (Agencourt Bioscience, Beverly, Mass.) according to the manufacturer's instructions. Exon sequences for EGFR (kinase domain) were amplified with specific primers by a nested polymerase chain reaction (nested PCR). Molecular types of the samples were pre-selected by DNA sequencing for exon 19 and exon 21 of EGFR.

Figure 4:
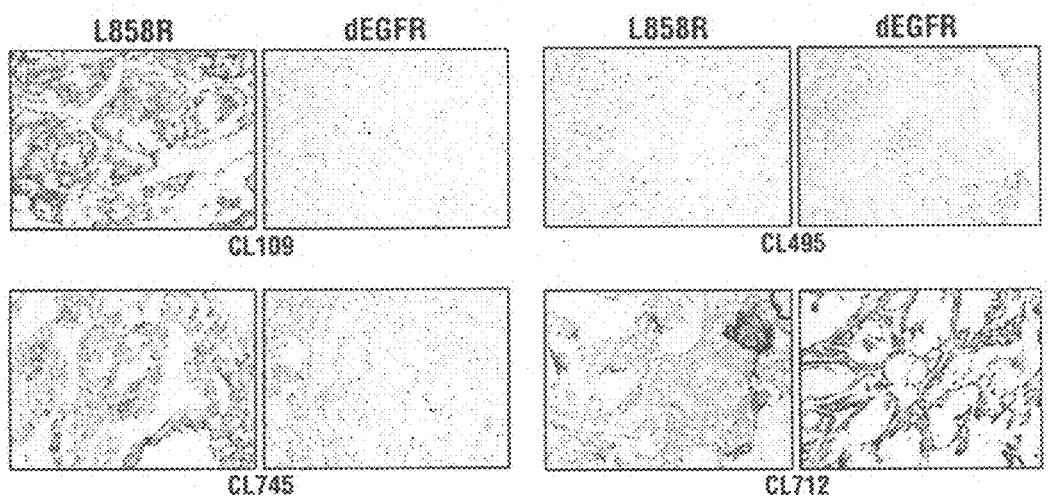
FIG. 4 depicts reactivity of the antibodies of the invention by immunohistochemistry analysis of four representative, non-limiting, pre-typed NSCLC samples (i.e., samples whose DNA had been sequenced prior to IHC analysis). Samples from patients CL109 and CL745, which by DNA sequencing were known to harbor the EGFR L858R point mutation, stained positive with the L858R-specific antibody, but negative for staining with the dEGFR-specific antibody. The samples from patients CL495 and CL712, which by DNA sequencing were known to harbor the E746-A750 deletion, stained positive with the dEGFR-specific antibody, but negative for staining with the L858R-specific antibody.

The immunohistochemical staining of four representative, non-limiting molecular pre-typed NSCLC samples with wtEGFR, E746-A750del and L858R mutant EGFR antibodies is showed in FIG. 4. This same IHC analysis was performed on additional molecular pre-typed NSCLC paraffin samples, and the IHC results of staining (i.e., binding)

by the EGFR mutant-specific antibodies of the invention (i.e., EGFR L858R (43B2E11E5B2) Rabbit mAb and the EGFR del722-726 (D6B6F8B10) Rabbit mAb) of these samples were scored using the scoring system set forth above in Table 1. As a control, staining with a pan-Kerain-specific antibody (Cell Signaling Technology, Danvers, Mass.) was employed, since keratin is exists on all epithelial cells, including lung cells. The genes of these samples were sequenced prior to IHC analysis. Table 2 provides the results of the scoring of the IHC results in comparison to the gene sequencing results obtained prior to IHC analysis, where the "Failed" category indicates that the DNA from the sample was too degraded for sequence to be obtained.

TABLE 2

| IHC (scored as described in Table 1) | | | Gene Sequencing | | | |
|---|---|---|---|---|---|---|
| | | | L858R | dEGFR | wt | Failed |
| Pan-Keratin 2-3 (+) | wtEGFR 2-3 (+) | L858R (+) | 24 | | 2 | 2 |
| | | dEGFR (+) | | 20 | 2 | 1 |
| | | L858R (−) | | | 35 | 4 |
| | | dEGFR (−) | | | | |
| | wtEGFR (−)-(+) | L858R (+) | | | | |
| | | dEGFR (+) | | | | |
| | | L858R (−) | | | 15 | 1 |
| | | dEGFR (−) | | | | |
| Pan-Keratin (−)-(+) | wtEGFR (−)-(+) | L858R (−) | 5 | 4 | 27 | 9 |
| | | dEGFR (−) | | | | |

As shown in Table 2, 5% of the samples which were IHC (+) were unable to be screened by sequencing (i.e., they were "Failed"). Thus, IHC may detect mutant tumors where the DNA of the sample is degraded or damaged to such a degree that DNA sequencing is impossible, resulting in a "Failed" result. 6.7% of the samples were IHC (+) but were wild-type according to the sequence analysis. Real time PCR may help confirm the presence of an EGFR mutation (i.e., a L858R or a del722-726 mutation) in these samples. Finally, 15% of the samples were IHC (−) and sequence (+). This finding may result from low expression level of the EGFR mutant, or from poor tissue sample quality. In these samples, the staining with the control pan-keratin antibody was weak, which means the quality of these tissue samples was not good for IHC.

Thus, a 100% correlation between IHC data and EGFR mutational status data was observed among these tumor samples.

Since the interpretation of the immunohistochemistry results depends on the intensity of staining at individual cancer cells, some tumor samples carrying the mutations with low percentage of cancer cells can be detected by IHC with mutant EGFR antibodies, but will be missed by direct sequencing. In addition, this assay enables us to examine paraffin blocks from small biopsy samples, which are difficult to extract enough high quality DNA for sequencing. Thus, this immunohistochemistry assay with the two EGFR mutant-specific antibodies described herein is a simple, rapid, sensitive, and reliable assay identify the specific EGFR mutations in NSCLC. When a wtEGFR-specific antibody is included, this immunohistochemistry assay can also measure total EGFR protein level.

Thus, IHC-positive tumors by both wtEGFR and mutant EGFR antibodies show stronger EGFR protein expression in all the xenograft and NSCLC samples, whereas IHC-negative by mutant EGFR antibodies, but positive by wtEGFR antibody, show EGFR overexpression without E746-A750del and L858R point mutation. Screening for such mutant EGFR proteins in cancer (e.g., lung cancers, such as NSCLC, or other cancers, particularly adenocarcinomas) by the immunohistochemistry may identify patients who will have response to therapeutic drugs, for example Gefitinib and Erlotinib.

Example 5

Unselected Tumors

To determine whether the antibodies of the invention could be used when the genotype of a patient's sample was not available, IHC was next performed on NSCLC tumors that had not been previously subjected to DNA sequence analysis. In other words, these tumor samples had an unknown genotype.

For these studies, paraffin embedded tumor specimens from 340 patients with primary NSCLC were screened for the presence of the EGFR deletion and the EGFR L858R point mutation by IHC with a panel of four antibodies. These 340 patients were known to have NSCLC, but the sequence of their EGFR gene had not been determined. The panel of antibodies included the two EGFR mutation-specific antibodies, a control wildtype EGFR-specific antibody, and a pan-cytokeratin-specific antibody to verify the tissue quality of the paraffin blocks. (Keratin, which is present in all epithelial cells including the NSCLC lung cancer cells, is bound by the pan-cytokeratin-specific antibody.)

Figure 5:
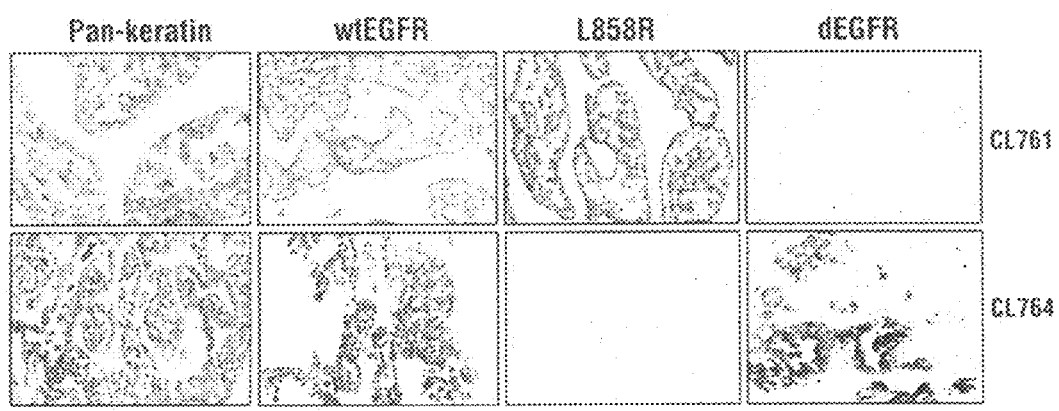
FIG. 5 depicts reactivity of the antibodies of the invention by immunohistochemistry of two representative, non-limiting, NSCLC samples of unknown genotype (i.e., samples whose DNA had not been sequenced prior to IHC analysis). The tumor sample from patient CL761 showed positive staining for Pan-cytokeratin-specific antibody, control wildtype EGFR-specific antibody, and L858R-specific antibody, but negative with the dEGFR (i.e., the E746-A750del)-specific antibody. In contrast, the tumor sample from patient CL764 stained positive for Pan-cytokeratin-specific antibody (positive control), control wildtype EGFR-specific antibody, and dEGFR-specific antibody, but negative with the L858R-specific antibody.

The IHC results of two representative NLSCS tumors from two patients, CL761 and CL764, are shown in FIG. 5. As shown in FIG. 5, the tumor sample from patient CL761 showed positive staining for Pan-cytokeratin-specific, control wtEGFR-specific, and L858R-specific antibodies, but was negative for staining with the dEGFR-specific antibody. In contrast, the tumor sample from patient CL764 stained positive for Pan-cytokeratin, control EGFR, and dEGFR antibody, but was negative with the L858R antibody.

Following the finding of these results by IHC analysis, DNA sequence analysis of these two patient's tumor samples confirmed the presence of the L858R mutation in patient CL761's tumor and the E746-A750 deletion in patient CL764's tumors.

IHC was performed on a total of 340 NSCLC samples from patients of unknown genotype (i.e., samples for which DNA analysis had not previously identified a mutation in the EGFR gene) and scored using the scoring criteria set forth in Table 1. These 340 NSCLC samples were categorized into the sub-types of pathology diagnoses for NSCLC, namely adenocarcinoma (AC), squamous cell carcinoma (SCC), and large cell carcinoma (LCC).

The results of these IHC analyses are provided in Table 3.

TABLE 3

IHC staining on molecular unknown tumor samples of NSCLC
340 NSCLC tumor samples were stained with L858R and dEGFR
antibodies

| Path Diag. | No. | L858R (+) | dEGFR (+) |
|---|---|---|---|
| AC | 217 | 28 | 23 |
| SCC | 112 | 0 | 1 (SCC?) |
| LCC | 11 | 0 | 0 |
| Total | 340 | 28 | 24 |

As shown in Table 3, 24 cases (7.1%) were scored positive with E746-A750 deletion antibody and 28 cases (8.2%) were scored positive with L858R antibody. Interestingly, as shown in Table 3, the sub-type of NSCLC that had the highest number of either EGFR L858R or dEGFR (i.e., E746-A750) mutation were the adenocarcinoma cells. Although the adenocarcinomas in Table 3 (and Table 4 below) were NSCLCs, adenocarcinoma also occurs in cancers including, without limitation, colon cancer, breast cancer, cervical cancer, pancreatic cancer (e.g., most pancreatic cancers are ductal adenocarcinomas), prostate cancer, stomach cancer, and esophageal cancer.

low quality DNA obtained from formalin-fixed paraffin-embedded tissues (FFPET) (Jaremko et al., Hum Mutat 25: 232-238, 2005). Table 5 shows the MS sequencing results from these nine tumor samples that showed a mismatch between IHC staining and direct DNA sequencing.

TABLE 5

EGFR Mutant Status from IHC, direct DNA sequencing, and MS sequencing

| | Exon 19 Deletion (E746-A750) | | | L858R Mutation | | | |
|---|---|---|---|---|---|---|---|
| No. | IHC | Direct Sequencing | MS Sequencing | No. | IHC | Direct Sequencing | MS Sequencing |
| CL182 | WT | Del | WT | CL182 | L858R | T847A | Failed |
| CL193 | WT | WT | WT | CL193 | WT | L858R | WT |
| CL472 | WT | Failed | WT | CL472 | L858R | WT | Failed |
| CL508 | Del | WT | Del | CL508 | WT | Failed | WT |
| CL720 | Del | WT | Del | CL720 | WT | L858R | WT |
| CL736 | WT | Del (L746-750) | Del | CL736 | WT | WT | WT |
| CL742 | WT | Del | WT | CL742 | WT | WT | WT |
| CL761 | WT | WT | WT | CL761 | L858R | WT | Failed |
| CL781 | WT | WT | Del | CL781 | WT | L858R | WT |

Additionally, 52 patients (15.3%) were positive with both EGFR mutation-specific antibodies. Moderate to strong staining with the control wtEGFR-specific antibody was observed in 84.6% of the mutant-EGFR positive cases, confirming the results provided above that a wildtype EGFR-specific antibody is inadequate in detecting tumor samples bearing an EGFR mutation.

To confirm the IHC results, direct DNA sequence analysis of the EGFR gene (exon 19 and 21) was performed on tumor specimens from 244 patients, including all adenocarcinoma samples and a small number of the squamous and large cell carcinoma samples. These results are provided below in Table 4. Note that the "Failed" category indicates that the DNA from these samples was too damaged or degraded to obtain adequate sequencing.

TABLE 4

Direct DNA sequencing results of Tumors Samples

| | | | | | Failed | |
|---|---|---|---|---|---|---|
| Pathology | No. | L858R(+) | dEGFR (+) | Wt | L858R | dEGFR |
| AC | 217 | 29 | 23 | 143 | 25 | 22 |
| SCC | 19 | 0 | 1 | 17 | 1 | 1 |
| LCC | 8 | 0 | 0 | 7 | 1 | 1 |
| Total | 244 | 29 | 24 | 167 | 27 | 24 |

As noted, 51 of the 244 patient tumor samples had DNA that was too degraded to be sequenced.

As shown in Table 4, all of the EGFR L858R mutations were found in adenocarcinomas, and 23 out of 24 EGFR E746-A750del mutations were found in adenocarcinomas. Thus, the IHC assay described herein is extremely useful for detecting an NSCLC (or another tumor type) that falls into an adenocarcinoma subtype.

In addition, all samples positive with the control EGFR antibody but showing a discrepancy between IHC and direct DNA sequencing results (nine total samples) were genotyped on the Sequenom mass spectrometry (MS)-based system. This technology has been reported to have higher accuracy than direct DNA sequencing in the genotyping of A correlation was made of the results shown in Table 5 between the different analysis methods used (i.e., IHC staining, direct DNA sequencing, and MS sequencing), and the results are provided below in Table 6.

TABLE 6

Correlction of MS sequencing to detect EGFR mutation with IHC and direct DNA sequencing

| Correlative No. | Exon 19 del | L858R | % Correlation |
|---|---|---|---|
| IHC/MS sequencing | 7/9 | 6/6 (3MS sequencing failed) | 87 |
| Direct sequencing/MS sequencing | 4/9 | 2/6 (3 MS sequencing failed) | 40 |

As shown in Table 6, a higher correlation between the Sequenom and IHC results was found than was found between direct DNA sequencing and IHC. This finding suggests that EGFR mutation-specific IHC might be more accurate than EGFR direct DNA sequencing.

Overall, the detection of these two EGFR mutations by IHC was confirmed in 47 of 52 cases by either direct DNA sequencing or Sequenom analysis. Overall, the sensitivity of the IHC assay using mutation specific antibodies was found to be 92%, with a specificity of 99%. DNA sequence analysis identified an additional 5 cases containing EGFR mutations that were negative for IHC by EGFR mutant-specific antibodies. However, these samples were negative for IHC by either control EGFR or pan-cytokeratin staining, suggesting that the quality of these samples was too poor for IHC. This suggests that PCR amplification and DNA sequencing may improve mutation detection for cases involving poorly preserved tissue.

Example 6

Sequence Analysis

Using the methods described above, the cDNA and amino acid sequences for the Heavy chain of the EGFR E746-A750del (6B6F8B10 (sometimes referred to as the D6B6F8B10 clone or just the 6B6 clone) rabbit monoclonal antibody were determined and are provided in SEQ ID NO:1 and SEQ ID NO:2, respectively. The cDNA and amino acid sequences for the Light chain of the EGFR E746-A750del (clone 6B6F8B10) rabbit monoclonal antibody are provided in SEQ ID NO:3 and SEQ ID NO:4, respectively. The cDNA and amino acid sequences for the Heavy chain of the EGFR L858R (clone 43B2E11E5B2) rabbit monoclonal antibody are provided in SEQ ID NO:5 and SEQ ID NO:6, respectively. The cDNA and amino acid sequences for the Light chain of the EGFR L858R (43B2E11E5B2) rabbit monoclonal antibody are provided in SEQ ID NO:7 and SEQ ID NO:8, respectively.

The Complementarity Determining Regions (CDRs) and Frame Work Regions (FWRs), as defined by Kabat rules, were determined from the sequence of the full length Heavy and Light chains using the method of Wu and Kabat (Wu, T. T. and Kabat, E. A. (1970) J. Exp. Med., 132, 211-250) for the EGFR del722-726 (6B6F8B10) and EGFR L858R (43B2E11E5B2) rabbit monoclonal antibodies.

The regions for the EGFR E746-A750del (6B6F8B10) Rabbit mAb were determined to have the following amino acid sequences:
Heavy Chain Complementarity Determining Regions (CDRs) and Frame Work Regions (FWRs):

```
                                         (SEQ ID NO: 9)
    CDR1: FSFSNNDWMC (SEQ ID NO: 10)
    CDR2: CIYGGSSIGTNYAGWAKG (SEQ ID NO: 11)
    CDR3: DLANL (SEQ ID NO: 12)
    FWR1: HCQSLEESGGGLVKPGASLTLTCTASG (SEQ ID NO: 13)
    FWR2: WVRQAPGKGLEWIA (SEQ ID NO: 14)
    FWR3: RFTISRTSSTTVALQMTSLTVADTATYFCTR (SEQ ID NO: 15)
    FWR4: WGPGTLVSVSS
```

The entire heavy chain variable region has the sequence:
HCQSLEESGGGLVKPGASLTLTCTASGFSFSNNDWMCWVRQAPGKGLE WIACIYGGSSIGTNYAGWAKGRFTISRTSSTTVALQMTSLTVADTATYFCT RDLANLWGPGTLVSVSS (SEQ ID NO: 81)

Light Chain Complementarity Determining Regions (CDRs) and Frame Work Regions (FWRs): as defined by Kabat rules

```
                                         (SEQ ID NO: 16)
    CDR1: QSSQSVYSDWLS (SEQ ID NO: 17)
    CDR2: EASKLAS (SEQ ID NO: 18)
    CDR3: LASYDCTRADCLA (SEQ ID NO: 19)
    FWR1: AQVLTQTPSSVSAAVGGTVTINC (SEQ ID NO: 20)
    FWR2: WYQQKGGQPPRQLIY (SEQ ID NO: 21)
    FWR3: GVPSRFSGSGSGTQFTLTINDVQCDDAATYYC (SEQ ID NO: 22)
    FWR4: FGGGTEVVVR
```

The entire light chain variable region has the sequence:
AQVLTQTPSSVSAAVGGTVTINCQSSQSVYSD-WLSWYQQKGGQPPRQLI YEASKLASGVPSRF-SGSGSGTQFTLTINDVQCDDAATYYCLASYDCTRAD CLAFGGGTEVVVR (SEQ ID NO: 82)

The regions for the 3197 EGFR L858R (43B2E11E5B2) Rabbit mAb were determined to have the following amino acid sequences:
3197 EGFR L858R (43B2E11E5B2) Rabbit mAb
Heavy Chain Complementarity Determining Regions (CDRs) and Frame Work Regions (FWRs): as Defined by Kabat Rules

```
                                         (SEQ ID NO: 23)
    CDR1: FSLNTYGVS (SEQ ID NO: 24)
    CDR2: YIFTDGQTYYASWAKG (SEQ ID NO: 25)
    CDR3: VDI (SEQ ID NO: 26)
    FWR1: QCQSVEESGGRLVTPGTPLTLTCTVSG (SEQ ID NO: 27)
    FWR2: WVRQAPGKGLEWIG (SEQ ID NO: 28)
    FWR3: RFTISKTSSTTVDLKITSPTTEDTATYFCAS (SEQ ID NO: 29)
    FWR4: WGPGTPVTVSS
```

The entire heavy chain variable region has the sequence:
QCQSVEESGGRLVTPGTPLTLTCTVSGFSLN-TYGVSWVRQAPGKGLEWIG YIFTDGQTYYASWAK-GRFTISKTSSTTVDLKITSPTTEDTATYFCASVDIW GPGTPVTVSS (SEQ ID NO: 83)

Light Chain Complementarity Determining Regions (CDRs) and Frame Work Regions (FWRs): as Defined by Kabat Rules

```
                                         (SEQ ID NO: 30)
    CDR1: QSSPSVYSNYLS (SEQ ID NO: 31)
    CDR2: DASHLAS (SEQ ID NO: 32)
    CDR3: LGSYDCSSVDCHA (SEQ ID NO: 33)
    FWR1: AQVLTQTPSPVSAAVGSTVTIKC (SEQ ID NO: 34)
    FWR2: WYQQKSGQPPKQLIY (SEQ ID NO: 35)
    FWR3: GVPSRFSGSGSGTQFTLTISGVQCDDAATYYC (SEQ ID NO: 36)
    FWR4: FGGGTEVVVK
```

The entire light chain variable region has the sequence:
AQVLTQTPSPVSAAVGSTVTIKCQSSPSVYSNYLSWY-QQKSGQPPKQLIY DASHLASGVPSRFSGSGS-

GTQFTLTISGVQCDDAATYYCLGSYDCSSVDC HAF-GGGTEVVVK (SEQ ID NO: 84)

Heavy and light chain V-D-J and V-J assignments were additionally identified. The heavy and light chain V-D-J and V-J assignments for the EGFR E746-A750del (6B6F8B10) rabbit monoclonal antibody were identified to be as follows.

Heavy chain V-D-J assignment:

V-region is VH1a3:
(SEQ ID NO: 37)
HCQSLEESGGGLVKPGASLTLTCTASGFSFSNNDWMCWVRQAPGKGLEWI

CIYGGSSIGTNYAGWAKGRFTISRTSSTTVALQMTSLTVADTATYFCTR

D-region is too short to identify:
(SEQ ID NO: 38)
DLA

J-region is JH4:
(SEQ ID NO: 39)
NLWGPGTLVSVSS

Light chain V-J assignment:

V-region is:
(SEQ ID NO: 40)
MDMRAPTQLLGLLLLWLPGATFAQVLTQTPSSVSAAVGGTVTINCQSSQS

VYSDWLSWYQQKGGQPPRQLIYEASKLASGVPSRFSGSGSGTQFTLTIND

VQCDDAATYYCLASYDCTRADCL

J-region is JK2:
(SEQ ID NO: 41)
AFGGGTEVVVR

The heavy and light chain V-D-J and V-J assignments for the EGFR L858R (43B2E11E5B2) rabbit monoclonal antibody were determined to be as follows:

Heavy chain V-D-J assignment:

V-gene is VH1a1:
(SEQ ID NO: 42)
QCQSVEESGGRLVTPGTPLTLTCTVSGFSLNTYGVSWVRQAPGKGLEWIG

YIFTDGQTYYASWAKGRFTISKTSSTTVDLKITSPTTEDTATYFCAS

D-gene is too short to identify:
(SEQ ID NO: 43)
VDI

J-region is JH4:
(SEQ ID NO: 44)
WGPGTPVTVSS

Light chain V-J assignment:

V-region:
(SEQ ID NO: 45)
MDMRAPTQLLGLLLLWLPGATFAQVLTQTPSPVSAAVGSTVTIKCQSSPS

VYSNYLSWYQQKSGQPPKQLIYDASHLASGVPSRFSGSGSGTQFTLTISG

VQCDDAATYYCLGSYDCSSVDCH

J-region is JK2:
(SEQ ID NO: 46)
AFGGGTEVVVK

Example 7

Epitope Mapping by Phase Display

An ELISA plate was coated with 100 ug/ml of antibody in 0.1M NaHCO$_3$ (pH 8.6). Samples of 100 ul of diluted mAb were added to each well and incubated overnight at 4° C. with gentle agitation. The plate was washed, incubated with blocking buffer (5 mg/l BSA, 0.02% NaN$_3$ in 0.1 M NaHCO$_3$ (pH 8.6) at 4° C. for 1 hour and then washed rapidly six times with TBST. The phage displayed libraries; Ph.D.-7 and Ph.D-12 were purchased from New England BioLabs (Ipswich, Mass.). The libraries were diluted to $2 \times 10^{11}$ with 100 ul of TBST, added to the plate and incubated for 60 minutes at room temperature with gentle agitation. The plate was then washed 10 times with TBST. Bound phage was eluted with 100 ul of 0.2 M glycine-HCl (pH 2.2), 1 mg/ml BSA for 10 minutes. The eluate was neutralized with 15 ul of 1 M Tris-HCl (pH 9.1). Eluted phage was amplified in ER2738 culture at 37° C. for 4.5 hours with vigorous shaking. Amplified phage was centrifuged for 10 minutes at 10,000 rpm at 4° C. and then 80% of the supernatant was transferred to a fresh tube along with ⅙ volume of PEG/NaCl[20% (w/v) PEG-8000, 2.5 M NaCl] was added to precipitate the phage at 4° C. overnight. Phage was isolated by centrifugation for 20 min at 10,000 g at 4° C. to pellet residual cells. The supernatant was transferred to a fresh microcentrifuge tube and reprecipitated with ⅙ vol. PEG/NaCl on ice for 60 min. Phage was isolated by centrifugation at 4° C. for 10 minutes and resuspended in 200 ul of TBS, 0.02% NaN$_3$. Isolated phage was centrifuged for 1 min to pellet any remaining insoluble matter. The supernatant was transferred to a fresh tube and amplified phage was titrated on LB medium plates containing IPTG and X-gal. The protocol for second and third-round biopanning was identical to the first.

The immunogens used for the EGFR L858R and EGFR deletion monoclonal antibodies were short peptides, 15 and 16 amino acids long, respectively (see Example 1). These peptides are conjugated to keyhole limpet hemocyanin (KLH) which is a complex, high-molecular weight protein widely used as a carrier protein in antibody production because of its excellent immunogenicity it confers to attached antigens. These immunogens strongly bind to their respective monoclonal antibodies. To determine the core epitope of 5-6 amino acids, two different phage display libraries available from New England Biolabs (Ipswich, Mass.) were utilized. The PhD7 library is the best characterized and encodes most if not all of the possible 7 residue sequences. With this library fewer clones are pulled out but they will be the ones with strong binding affinities compared to the other library PhD12. PhD12 encodes 12-residue sequences and will pull down more clones that may have multiple weak binding contacts.

The EGFR E749-A750del rabbit mAb when screened against both the PhD7 and PhD12 suggested that the "TSP" (Table 7) is a potentially important area within the immunogen.

The "TSP" site is directly adjacent to the deletion site. These experiments may be validated with peptide ELISAs.

TABLE 7

Epitope mapping of EGFR E746-A750 Del Rabbit mAb
EGFR E746-A750del (6B6 clone (i.e., the 6B6F8B10) Rabbit mAb
Immunogen: CKIPVAIKTSPKANKE

| Clone Frequency | Amino Acid Sequence |
|---|---|
| PhD 12 | |
| 2/9 | HKMHSHPRLTSP |
| 1/9 | HTSYYTNTDWGR |
| 1/9 | WPHQVHKHIURQ |
| 1/9 | HWGHHSKSHP.R |
| 2/9 | HWGNHSKSHPQR |
| 1/9 | HRGHHSQSQTHR |
| 1/9 | HLKHHPPYKDAT |
| PhD 7 | |
| 1/11 | GPTADTN |
| 1/11 | SAFYQLN |
| 1/11 | RPSTSPL |
| 1/11 | QLFTSAS |
| 1/11 | MPNRNRS |
| 1/11 | GDGPLRR |
| 1/11 | KHPTYRQ |
| 1/11 | MPNRNRS |
| 1/11 | KLHQMRT |
| 1/11 | KVSRTGR |
| 1/11 | VPRAIYH |

Phage display using the EGFR L858R rabbit mAb identified a clear consensus sequence of "TDXGR" using the PhD12 library. These data are summarized in Table 8. These data may be verified with peptide ELISAs.

TABLE 8

Epitope mapping of EGFR L858R Rabbit mAb
EGFR L858R (43B2 (i.e., the 43B2E11E5B2))
Rabbit mAb
Immunogen: CTDFGRAKL
PhD 12

| Clone Frequency | Amino Acid Sequence |
|---|---|
| 5/9 | MEIITDLGRPML |
| 1/9 | AKSSTDFGRAQV |
| 1/9 | YPPAPLGRTTDF |
| 1/9 | KRQIPSPPQWDP |
| 1/9 | TFHNKLLLHDWR |

Table 9 provides a summary of the consensus sequences for the two EGFR mutant-specific antibodies.

TABLE 9

Summary of epitope sequences

| | Amino Acid Sequence |
|---|---|
| EGFR L858R | |
| Immunogen | CKITDFGRAKLLGAE |
| Central Epitope | TDXGR |
| EGFR (E746-A750 DEL) | |
| Immunogen | CKIPVAIKTSPKANKE |
| Central Epitope | TSP |

To validate the consensus sequences obtained via phage display libraries (Table 9), alanine scanning may be performed by mutating residues within the antigen to alanine and analyzing which changes are important for binding. Both of the EGFR mutant antibodies were immunized with short peptides sequences ranging from 15-16 amino acids. For these antibodies, epitope mapping may performed with peptide ELISAs with mutated versions of these immunogens.

What is claimed is:

1. A purified antibody that specifically binds an epidermal growth factor receptor (EGFR) comprising a deletion at position E746-A750, wherein said antibody comprises a heavy chain variable region having CDRs 1, 2, and 3 comprising the amino acid sequences set forth in SEQ ID NOs: 9, 10, and 11 respectively, and a light chain variable region having CDRs 1, 2, and 3 comprising the amino acid sequences set forth in SEQ ID NOs: 16, 17, and 18 respectively.

2. A purified antibody that specifically binds an epidermal growth factor receptor (EGFR) comprising a deletion at position E746-A750, wherein said antibody comprises a heavy chain variable region comprising the amino acid sequence of SEQ ID NO: 81.

3. The antibody of claim 2, wherein the antibody comprises a light chain variable region comprising the amino acid sequence of SEQ ID NO: 82.

4. A purified antibody that specifically binds an epidermal growth factor receptor (EGFR) comprising a deletion at position E746-A750, wherein said antibody comprises a light chain variable region comprising the amino acid sequence of SEQ ID NO: 82.

5. A purified antibody that specifically binds an epidermal growth factor receptor (EGFR) comprising a deletion at position E746-A750, wherein the heavy chain of the antibody comprises SEQ ID NO: 2 and the light chain of the antibody comprises SEQ ID NO: 4.

* * * * *